United States Patent
Kikuchi et al.

(10) Patent No.: US 7,547,680 B2
(45) Date of Patent: Jun. 16, 2009

(54) BENZIMIDAZOLE DERIVATIVES AND MEDICAL USES THEREOF

(75) Inventors: Norihiko Kikuchi, Nagano (JP); Yoshinori Nonaka, Nagano (JP); Kazuya Tatani, Nagano (JP); Masahiro Hiratochi, Nagano (JP); Yu Kuramochi, Nagano (JP); Masayuki Isaji, Nagano (JP); Kazuo Shimizu, Nagano (JP); Takashi Miyagi, Nagano (JP)

(73) Assignee: Kissei Pharmaceuticals, Co., Ltd., Nagano (JP)

( * ) Notice: Subject to any disclaimer, the term of this patent is extended or adjusted under 35 U.S.C. 154(b) by 294 days.

(21) Appl. No.: 11/473,957

(22) Filed: Jun. 23, 2006

(65) Prior Publication Data

US 2008/0038242 A1    Feb. 14, 2008

(30) Foreign Application Priority Data

Dec. 16, 2004 (WO) .................. PCT/JP2004/019290

(51) Int. Cl.
*A01N 43/04* (2006.01)
*A61K 31/70* (2006.01)

(52) U.S. Cl. .......................... 514/43; 514/42
(58) Field of Classification Search ........................ None
See application file for complete search history.

(56) References Cited

U.S. PATENT DOCUMENTS 6,307,043 B1 * 10/2001 Chamberlain et al. ...... 536/28.9

FOREIGN PATENT DOCUMENTS

WO    WO 97/25337    7/1997

OTHER PUBLICATIONS

N. Zollner, "Purine and pyrimidine metabolism", Proc.Nutr.Soc., vol. 41, (1982), pp. 329 to 342.

Mabel W.L. Ritzel, et al., "Molecular Identification and Characterization of Novel Human and Mouse Concentrative Na+ -Nucleoside Contransporter Proteins (hCNT3 and mCNT3) Broadly Selective for Purine and Pyrimidine Nucleosides (System cib)", J. Biol. Chem., vol. 276, (2001), pp. 2914 to 2927.

* cited by examiner

*Primary Examiner*—Patrick T Lewis
(74) *Attorney, Agent, or Firm*—Frenkel & Associates, P.C.

(57) ABSTRACT

The present invention provides benzimidazole derivatives represented by the following formula (I) or pharmaceutically acceptable salts thereof, or prodrugs thereof, which exert an inhibitory activity on sodium-dependent nucleoside transporter 2 and are useful for a disease associated with an abnormality of plasma uric acid level. The compounds of the present invention are useful for the prevention or treatment of gout, hyperuricemia, urinary lithiasis, hyperuricemic nephropathy or the like.

In the formula, n is 1 or 2; $R^1$ and $R^2$ are H, a halogen atom, cyano group, optionally substituted alkyl group, optionally substituted aryl group or the like; $R^3$ is H, a halogen atom, optionally substituted alkyl group or the like; $R^4$ and $R^5$ are H, a halogen atom, OH or the like; and $R^6$ and $R^X$ are H or OH: $R^Y$ is F or OH.

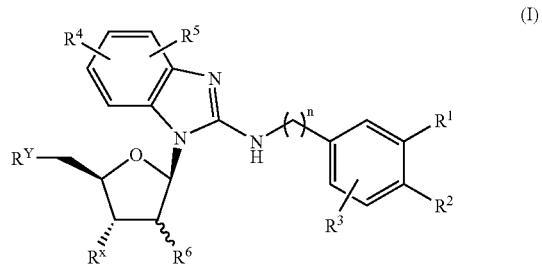

(I)

14 Claims, 1 Drawing Sheet

BENZIMIDAZOLE DERIVATIVES AND MEDICAL USES THEREOF

TECHNICAL FIELD

The present invention relates to benzimidazole derivatives which are useful as medicaments.

More particularly, the present invention relates to benzimidazole derivatives or pharmaceutically acceptable salts thereof, or prodrugs thereof which exhibit an inhibitory activity in sodium-dependent nucleoside transporter 2 (hereinafter referred to as CNT2) and are useful as agents for the prevention or treatment of a disease associated with an abnormality of plasma uric acid level.

BACKGROUND

Uric acid is the end product of purine bodies in human. The upper limit of normal uric acid concentration solved in plasma is 7.0 mg/dL independently from sex and age, and the condition with higher concentration is clinically defined as hyperuricemia. Hyperuricemia affects mostly in adult men and is considered to result from combination of a genetic factors involved in metabolism of purine bodies and secondary factors such as consumption of a high-energy food, nucleic acid rich food or the like. Conditions of persistent hyperuricemic increase a risk of developing arthritis following to urate crystal deposition in intra- or peri-joints. The condition with such developed arthritis is called gout, and the arthritis is called gouty attack. Hyperuricemia is classified broadly into types consisting of a uric acid overproduction-type wherein the uric acid production increases, a uric acid underexcretion-type wherein the uric acid excretion in urine decreases, and a mixed type of them (for example, see Guideline for the management of hyperuricemia and gout, Version 1, 2002 (hereinafter referred to as the Management guideline), pp. 12-22; and Diagnosis and Treatment, Vol. 90, No. 2, pp. 186-191, 2002).

In the prevention or treatment of hyperuricemia or gout, the basis is to control the plasma uric acid level under a certain level to prevent the incidence of gouty arthritis, and the incidence of the gouty arthritis is considered the lowest in the case to control plasma uric acid level within the range from 4.4 to 6.6 mg/dL. So far, for the treatment of hyperuricemia or gout, allopurinol of a uric acid synthesis inhibitor or probenecid, bucolome, benzbromarone of uricosuric drugs or the like have been used for the improvement of the plasma uric acid level. In addition, in the treatment of gouty attacks, an agent for the pain attack such as colchicine, a nonsteroidal anti-inflammatory agent such as indometacin, naproxen, fenbufen, pranoprofen, oxaprozin, and an adrenocortical steroid are used (for example, see the above Management guideline, pp. 23-45).

Allopurinol of a uric acid synthesis inhibitor has side effects such as poisoning syndrome (hypersensitivity angiitis), Stevens-Johnson syndrome, exfoliative dermatitis, aplastic anemia, hepatic insufficiency or the like. In addition, a uricosuric drug has a restriction not to be used for a patient with renal failure, and probenecid, bucolome and benzbromarone have side effects such as gastrointestinal disorder, urinary lithiasis, especially, benzbromarone sometimes causes fulminant hepatic failure in a patient with idiosyncrasy (for example, see the above Management guideline, pp. 32-33).

It has been desired to develop a new preventative or therapeutic drug having few side effects which can solve such problems of these existing drugs, especially with a different mechanism compared with existing drugs from the viewpoint of broadening the choices of treatment methods.

Since hyperuricemia is brought on by life style such as overeating, food preference for high purine, high fat or high protein, habitual drinking, insufficient exercise or the like and highly correlated with obesity, hypertension, abnormality in the metabolism of sugar or lipid or the like, life style guidance plays an important role as non-drug therapy in order to correct the life style. In particular, dietary therapy to avoid excessive intake of purine has a major rule. However, it is difficult to continue such diet therapy and improvement of the life style, and they often fail.

An agent to regulate the digestion and absorption of purine which is different from existing agents such as a uric acid synthesis inhibitor or a uricosuric drug has been suggested for use as a part of or instead of dietary therapy (for example, see the Japanese patent publication no. 2001-163788). The invention described in the patent publication relates to a drug to regulate the digestion and absorption of purine including chitosan for human, and the dosage is within the range of 2 to 2000 mg/kg/day which is rather high. In addition, it is used in the form of drink or food, and thus mainly used as an supplement in the dietary therapy. Moreover, an agent and food for the improvement of hyperuricemia including chitosan or dietary fiber as an active ingredient other than the invention described in the above patent publication have been developed (for example, see the Japanese patent no. 2632577). Although the effects of chitosan or dietary fiber described in these gazettes are not clear, it is suspected that purine binds to or is trapped by a polymer, chitosan or dietary fiber, and so the production of uric acid decreases.

On the digestion and absorption pathway of nucleic acid in human, nucleic acids are released in the intestine from a nucleic acid and nucleoproteins ingested, and these nucleic acids are broken down into mononucleotides by ribonucleases, deoxyribonucleases and polynucleotidases. Furthermore, it is considered that the pathway wherein mononucleotide is degraded into nucleoside by nucleotidases and phosphatase and then the nucleosides are absorbed is the main pathway. In the pathway, it is considered that the absorbed purine nucleoside is changed to uric acid (for example, see Harper's Biochemistry, translation of the original edition 25, p. 417, 2001). As other pathways, it can be suspected that purine nucleoside is broken down to form purine base and then absorbed, or purine base contained in food is directly absorbed. However, these pathways have not been yet unexplained in detail.

Membrane proteins called nucleoside transporter relate to the nucleoside uptake in the intestine. As such transporters, there are Equilibrative transporters which have transport process of nucleoside into the cell by the concentration gradient of nucleoside (hereinafter referred to as ENT) and sodium-dependent nucleoside transporters which are driven by the concentration gradient of ion between in and out of the cell (hereinafter referred to as CNT) in mammalian cells (for example, see Membrane Transporters as Drug Targets, pp. 318-321, 1999). As human nucleoside transporters, two types of ENT, Type 1 (hereinafter referred to as ENT1) and Type 2 (hereinafter referred to as ENT2), have been identified and cloned so far (for example, see NATURE MEDICINE, Vol. 3, No. 1, pp. 89-93, 1997; and The Journal of Biological Chemistry, Vol. 273, No. 9, pp. 5288-5293, 1998). In addition, three types of CNT, Type 1 (hereinafter referred to as CNT1), Type 2 (hereinafter referred to as CNT2) and Type 3 (hereinafter referred to as CNT3) have been identified and cloned (for example, see American Journal of Physiology Cell Physiology, Vol. 272, pp. C707-C714, 1997; American Journal of Physiology Renal Physiology, Vol. 273, pp. F1058-F1065, 1997; The Journal of Biological Chemistry, Vol. 276, No. 4, pp. 2914-2927, 2001).

The distribution and characteristics of these transporters have been confirmed to some extent. Regarding ENTs, both ENT1 and ENT2 exist broadly in human normal tissues and transport both purine and pyrimidine nucleosides. In terms of function, their sensitivities to the inhibition by nitrobenzylthioinosine (hereinafter referred to as NBMPR) are different, that is, ENT1 is markedly inhibited by a low concentration of NBMPR ($IC_{50}$<5 nM), while ENT2 is hardly inhibited by NBMPR, but is inhibited only by a high concentration of NBMPR ($IC_{50}$>1 μM) (for example, see Membrane Transporters as Drug Targets, pp. 316-318, 1999).

On the other hand, regarding CNTs, CNT1 transports pyrimidine nucleoside and adenosine, and the messenger RNA (hereinafter referred to as mRNA) has been confirmed to exist in the jejunum and kidney in rats. CNT2 transports purine nucleoside and uridine, and various kinds of mRNA have been confirmed to exist in organs including the heart, liver, skeletal muscles, kidney, intestines or the like in human. CNT3 has been recently cloned and transports both purine and pyrimidine nucleosides, and the mRNA has been confirmed to exist in the bone marrow, pancreas, intestines and mammary gland in human. In addition, in terms of function, it has been confirmed that all of these CNTs are not influenced by NBMPR (for example, see The Journal of Biological Chemistry, Vol. 276, No. 4, pp. 2914-2927, 2001; and Membrane Transporters as Drug Targets, pp. 327-332, 1999).

In addition, in the previous studies on transport mechanism in the intestines, it is shown that nucleoside is taken up through CNT from mucosal side and transported through ENT from serosal side (for example, see Gastrointestinal transport, molecular physiology, pp. 334-337, 2001). However, the contribution of nucleoside transporters in the human intestines, especially in the human small intestine has been not clarified in detail.

On the other hand, in the gazettes of Japanese patent publication no. 2001-163788 and Japanese patent no. 2632577, it has been reported that plasma uric acid level is lowered by inhibiting purine absorption. Additionally, it was confirmed that plasma uric acid level is lowered by restriction on eating dietary sources of purine in human, and that uric acid synthesized from purine nucleosides absorbed in the intestine reflects plasma uric acid concentration (for example, see Proceedings of the Nutrition Society, Vol. 41, pp. 329-342, 1982) Therefore, plasma uric acid level can be controlled by effective inhibition of the purine nucleoside absorption through the intestines.

Some compounds including dipyridamole have been reported so far as an inhibitor of a nucleoside transporter (for example, see Japanese patent publication no. H6-247942, Japanese patent publication no. Tokuhyo 2002-504134, and Japanese patent publication no. Tokuhyo 2001-517226). All of these inhibitors are ENT inhibitors, and mainly used as a drug for the cardioprotection, treatment of pain, enhancement of antitumor drug or the like. On the other hand, there has not been any report on a CNT inhibitor so far. Moreover, it has not ever been reported or suggested that a compound having an inhibitory activity on CNT2 can inhibit the purine nucleoside absorption through the intestines effectively, and is useful as a drug for a disease associated with an abnormality of plasma uric acid level.

In addition, it was reported that as a glycosylated benzimidazole derivative, a benzimidazole derivative glycosylated with L-ribose is useful for the prevention or treatment of virus infection such as herpes virus or coronary restenosis. However, any benzimidazole derivative glycosylated with D-ribose has not been reported. Furthermore, it has not ever been reported or suggested that a glycosylated benzimidazole derivative is useful for the prevention or treatment of a disease associated with an abnormality of plasma uric acid level such as gout, hyperuricemia or the like (see International publication no. WO97/25337 pamphlet, U.S. Pat. No. 6,204,249 gazette, U.S. Pat. No. 6,617,315 gazette or the like).

DISCLOSURE OF THE INVENTION

The present inventors have studied earnestly on the nucleoside absorption in the human intestines. As a result, it was found that CNT2 is the most distributed in the human intestines, especially upper small intestines and that a phenylalkylaminobenzimidazole derivative which is glycosylated with D-ribose or the like at its 1-position and also may have a substituent at its 2-position has an inhibitory activity on CNT2, and the purine nucleoside absorption in the body is inhibited by inhibiting CNT2. Thus, CNT2 is deeply involved in the purine nucleoside absorption, and since plasma uric acid level can be lowered by inhibiting CNT2, the above benzimidazole derivative having an inhibitory activity on CNT2 can be a novel drug for the prevention or treatment for a disease associated with an abnormality of plasma uric acid level by a mechanism completely different from that of the currently existing drugs, thereby forming the basis of the present invention.

The present inventors practiced cDNA cloning of human CNTs, firstly analyzed the distribution pattern of CNTs in human tissues and confirmed that CNT2 is expressed abundantly in the human small intestines. In addition, they analyzed the distribution pattern at each portion of digestive tract, and confirmed that CNT1 is expressed mostly in jejunum and ileum of the lower small intestines, and CNT2 is expressed mostly in the duodenum of the upper small intestines and next in the jejunum.

The present inventors further studied to find a compound having an inhibitory activity on CNT2, and finally confirmed that a benzimidazole derivative represented by the following general formula (I) has a strongly inhibitory activity on the uptake of adenosine in an experiment by using COS 7 cells transfected with a human CNT2 gene. In addition, in a purine tolerance test in rats, such a compound inhibits the increase of plasma uric acid level. Therefore, it was found that since a benzimidazole derivative represented by the following general formula (I) or a pharmaceutically acceptable salt thereof, or a prodrug thereof exerts an excellent inhibitory activity on CNT2 and inhibits the increase of plasma uric acid level markedly, the same is useful as a drug for the prevention or treatment of a disease associated with an abnormality of plasma uric acid level.

That is, the present invention relates to:

[1] a benzimidazole derivative represented by the general formula:

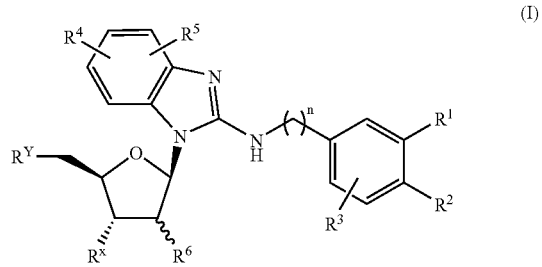

(I)

wherein n represents 1 or 2;

$R^1$ and $R^2$ independently represents a hydrogen atom, a halogen atom, a cyano group, any of the following substituents (A) to (C) which may have the same or different 1 to 3 groups selected from a substituent group α, any of the following substituents (D) to (G) which may have the same or different 1 to 3 groups selected from substituent groups α and β, or any of the following substituents (H) to (M);

$R^3$ represents a hydrogen atom, a halogen atom, any of the following substituents (A) to (C) which may have the same or different 1 to 3 groups selected from a substituent group α, or any of the following substituents (H) to (M);
(A) a $C_{1-6}$ alkyl group;
(B) a $C_{2-6}$ alkenyl group;
(C) a $C_{2-6}$ alkynyl group;
(D) a $C_{3-8}$ cycloalkyl group;
(E) a 3 to 10-membered cyclic heterocycloalkyl group;
(F) a $C_{6-10}$ aryl group;
(G) a 5 to 10-membered cyclic heteroaryl group;
(H) $OR^7$;
(I) $SR^8$;
(J) $NR^9R^{10}$;
(K) $COOR^{11}$;
(L) $CONR^{12}R^{13}$;
(M) $NHCOR^{14}$ (in the groups $R^7$ to $R^{14}$ independently represent a hydrogen atom, or any of the following substituents (N) to (P) which may have the same or different 1 to 3 groups selected from a substituent group α, or any of the following substituents (Q) to (V) which may have the same or different 1 to 3 groups selected from substituent groups α and β
(N) a $C_{1-6}$ alkyl group;
(O) a $C_{2-6}$ alkenyl group;
(P) a $C_{2-6}$ alkynyl group;
(Q) a $C_{3-8}$ cycloalkyl group;
(R) a 3 to 10-membered cyclic heterocycloalkyl group;
(S) a quaternary salt of a 3 to 10-membered cyclic nitrogen-containing heterocycloalkyl group;
(T) a $C_{6-10}$ aryl group;
(U) a 5 to 10-membered cyclic heteroaryl group;
(V) a quaternary salt of a 5 to 10-membered cyclic nitrogen-containing heteroaryl group)

$R^4$ and $R^5$ independently represent a hydrogen atom, a halogen atom, a hydroxy group, a $C_{1-6}$ alkyl group or $C_{1-6}$ alkoxy group;
$R^6$ and $R^X$ independently represent a hydrogen atom or a hydroxy group;
$R^Y$ represents a fluorine atom or a hydroxy group, and with the proviso that at least one of $R^1$, $R^2$ and $R^3$ does not represent a group selected from a hydrogen atom, a halogen atom, a hydroxy group, a $C_{1-6}$ alkoxy group, $NH_2$ and COOH

[Substituent Group α]
(a) a halogen atom;
(b) a cyano group;

any of the following substituents (c) to (h) which may have the same or different 1 to 3 groups selected from a substituent group γ, or any of the following substituents (i) to (v)
(c) a $C_{3-8}$ cycloalkyl group;
(d) a 3 to 10-membered cyclic heterocycloalkyl group;
(e) a quaternary salt of a 3 to 10-membered cyclic nitrogen-containing heterocycloalkyl group;
(f) a $C_{6-10}$ aryl group;
(g) a 5 to 10-membered cyclic heteroaryl group;
(h) a quaternary salt of a 5 to 10-membered cyclic nitrogen-containing heteroaryl group;
(i) $OR^{15}$;
(j) $SR^{16}$;
(k) $NR^{17}R^{18}$;
(l) $N^+R^DR^ER^F$;
(m) $COOR^{19}$;
(o) $NHCOR^{20}$;
(p) $NHC(=NH)-NH_2$;
(q) $C(=NH)-NH_2$ (which is bound to a nitrogen atom of a nitrogen-containing heterocycloalkyl group);
(r) $NR^{21}CONR^{22}R^{23}$;
(s) $NR^GSO_2R^H$;
(t) $SO_2R^I$ ($R^I$ represents a $C_{1-6}$ alkyl group, a $C_{2-6}$ alkenylene group or a hydroxy($C_{1-6}$ alkyl) group);
(u) $CONR^{24}R^{25}$;
(v) $SO_2NR^{26}R^{27}$ (in the groups $R^{D-F}$ independently represent any of the following substituents (y1) to (y11) which may have the same or different 1 to 3 groups selected from a substituent group γ; $R^{15}$, $R^{16}$, $R^{19-21}$ and $R^{G-H}$ independently represent a hydrogen atom, or any of the following substituents (y1) to (y11) which may have the same or different 1 to 3 groups selected from a substituent group γ; $R^{17}$, $R^{18}$ and $R^{22}$ to $R^{27}$ independently represent a hydrogen atom, or any of the following substituents (y1) to (y11) which may have the same or different 1 to 3 groups selected from a substituent group γ; or $R^{17}$ and $R^{18}$, $R^{22}$ and $R^{23}$, $R^{24}$ and $R^{25}$, and $R^{26}$ and $R^{27}$ independently may bind together with the neighboring nitrogen atom to form a 3 to 8-membered aliphatic cyclic amino group
(y1) a $C_{1-6}$ alkyl group;
(y2) a $C_{2-6}$ alkenyl group;
(y3) a $C_{2-6}$ alkynyl group;
(y4) a $C_{3-8}$ cycloalkyl group;
(y5) a 3 to 10-membered cyclic heterocycloalkyl group;
(y6) a $C_{6-10}$ aryl group;
(y7) a 5 to 10-membered cyclic heteroaryl group;
(y8) a $C_{3-8}$ cycloalkyl-$C_{1-6}$ alkyl group;
(y9) a 3 to 10-membered cyclic heterocycloalkyl-$C_{1-6}$ alkyl group;
(y10) a $C_{6-10}$ aryl-$C_{1-6}$ alkyl group;
(y11) a 5 to 10-membered cyclic heteroaryl-$C_{1-6}$ alkyl group)

[Substituent Group β]

any of the following substituents (z1) to (z3) which may have the same or different 1 to 3 groups selected from a substituent group γ:
(z1) a $C_{1-6}$ alkyl group;
(z2) a $C_{2-6}$ alkenyl group;
(z3) a $C_{2-6}$ alkynyl group

[Substituent Group γ]
(1) a halogen atom;
(2) a nitro group;
(3) a cyano group;
(4) $OR^{28}$;
(5) $SR^{29}$;
(6) $NR^{30}R^J$ ($R^{30}$ and $R^J$ independently represent a hydrogen atom, a $C_{1-6}$ alkyl group, a $C_{2-6}$ alkenyl group, a hydroxyl($C_{1-6}$ alkyl) group, a $C_{6-10}$ aryl-$C_{1-6}$ alkyl group or a $C_{6-10}$ aryl group);
(7) $N^+R^KR^LR^M$ ($R^{K-M}$ independently represent a $C_{1-6}$ alkyl group, a $C_{2-6}$ alkenyl group, a hydroxyl($C_{1-6}$ alkyl) group, a $C_{6-10}$ aryl-$C_{1-6}$ alkyl group or a $C_{6-10}$ aryl group);
(8) $COR^{31}$;
(9) $COOR^{32}$;
(10) $OCOR^{33}$;
(11) $NHCOR^{34}$;
(12) $NHC(=NH)-NH_2$;
(13) $C(=NH)-NH_2$ (which is bound to a nitrogen atom of a heterocycloalkyl group)
(14) $NR^{35}CONR^{36}R^{37}$;

(15) $NR^NCOOR^O$;
(16) $CONR^{38}R^{39}$;
(17) $SO_2NR^{40}R^{41}$;
(18) a hydroxyl($C_{2-6}$ alkyl) group;
(19) a 5 to 10-membered cyclic nitrogen-containing heteroaryl group (in the groups $R^{28}$, $R^{29}$, $R^{31-35}$, $R^N$ and $R^O$ independently represent a hydrogen atom, a $C_{1-6}$ alkyl group or a $C_{6-10}$ aryl-$C_{1-6}$ alkyl group; $R^{36}$ to $R^{41}$ independently represent a hydrogen atom, or a $C_{1-6}$ alkyl group, or $R^{36}$ and $R^{37}$, $R^{38}$ and $R^{39}$, and $R^{40}$ and $R^{41}$ independently may bind together with the neighboring nitrogen atom to form a 3 to 8-membered aliphatic cyclic amino group), or a pharmaceutically acceptable salt thereof, or a prodrug thereof;

[2] a benzimidazole derivative as defined in the above [1] wherein n represents 1, or a pharmaceutically acceptable salt thereof, or a prodrug thereof;

[3] a benzimidazole derivative as defined in the above [1] or [2] wherein $R^Y$ represents a hydroxy group, or a pharmaceutically acceptable salt thereof, or a prodrug thereof;

[4] a benzimidazole derivative as claimed in any one of claims [1] to [3] wherein $R^1$ and $R^3$ independently represent a hydrogen atom, a halogen atom, any of the substituents (A) to (C) which may have the same or different 1 to 3 groups selected from the substituent group α, or any of the substituents (H) to (M), $R^2$ independently represents a hydrogen atom, a halogen atom, a cyano group, any of the substituents (A) to (C) which may have the same or different 1 to 3 groups selected from the substituent group α, any of the substituents (D) to (G) which may have the same or different 1 to 3 groups selected from the substituent groups α and β, or any of the substituents (H) to (M), or a pharmaceutically acceptable salt thereof, or a prodrug thereof;

[5] a benzimidazole derivative as defined in any one of the above [1] to [4] wherein the substituent:

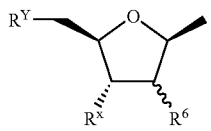

represents a D-ribosyl group, or a pharmaceutically acceptable salt thereof, or a prodrug thereof;

[6] a benzimidazole derivative (Ia) as defined in the above [1] wherein n represents 1 and both of $R^X$ and $R^Y$ represent a hydroxy group, or a pharmaceutically acceptable salt thereof, or a prodrug thereof:

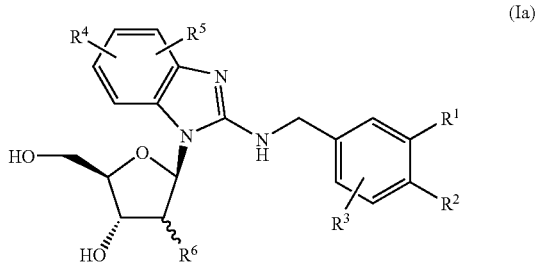

(Ia)

wherein $R^1$ to $R^6$ have the same meanings as defined above;

[7] a benzimidazole derivative as defined in the above [6] wherein $R^1$ represents $OR^7$ (with the proviso that $R^7$ represents a $C_{1-6}$ alkyl group which has a hydroxy group, $NR^{17}R^{18}$ or $N^+R^DR^ER^F$ ($R^{17}$, $R^{18}$ and $R^{D-F}$ have the same meanings as defined in the above [1]) or a hydroxy group; $R^2$ represents $OR^7$ (with the proviso that $R^7$ represents a $C_{1-6}$ alkyl group which has a hydroxy group, $NR^{17}R^{18}$ or $N^+R^DR^ER^F$ ($R^{17}$, $R^{18}$ and $R^{D-F}$ have the same meanings as defined in the above [1]), a hydroxy group, or a $C_{6-10}$ aryl group which may have a hydroxy group or $OR^{15}$ ($R^{15}$ has the same meaning as defined in the above [1]), $R^3$, $R^4$ and $R^5$ represent a hydrogen atom, or a pharmaceutically acceptable salt thereof, or a prodrug thereof;

[8] a pharmaceutical composition comprising as an active ingredient a benzimidazole derivative as defined in any one of the above [1] to [7], or a pharmaceutically acceptable salt thereof, or a prodrug thereof;

[9] a pharmaceutical composition as defined in the above [8] for the prevention or treatment of a disease associated with an abnormality of plasma uric acid level;

[10] a pharmaceutical composition as defined in the above [9] wherein the disease associated with an abnormality of plasma uric acid level is a disease selected from gout, hyperuricemia, urinary lithiasis, hyperuricemic nephropathy and acute uric acid nephropathy;

[11] a pharmaceutical composition as defined in the above [9] wherein the disease associated with an abnormality of plasma uric acid level is gout;

[12] a pharmaceutical composition as defined in the above [9] wherein the disease associated with an abnormality of plasma uric acid level is hyperuricemia;

[13] a pharmaceutical composition as defined in any one of the above [8] to [12] comprising in combination as an active ingredient at least one agent selected from a group consisting of colchicine, a nonsteroidal anti-inflammatory agent, an adrenocortical steroid, a uric acid synthesis inhibitor, a uricosuric drug, a urinary alkalinizer and a uric acid oxidase;

[14] a pharmaceutical composition as defined in the above [13] wherein the nonsteroidal anti-inflammatory agent is indometacin, naproxen, fenbufen, pranoprofen, oxaprozin, ketoprofen, etoricoxib or tenoxicam; the uric acid synthesis inhibitor is allopurinol, oxypurinol, febuxostat or Y-700; the uricosuric drug is probenecid, bucolome or benzbromarone; the urinary alkalinizer is sodium hydrogen carbonate, potassium citrate or sodium citrate; the uric acid oxidase is rasburicase, uricase PEG-20, a recombinant uric acid oxidase (uricase); and the like.

In the compounds represented by the above general formula (I) of the present invention, the term "$C_{1-6}$ alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "$C_{2-6}$ alkenyl group" means a straight-chained or branched alkenyl group having 2 to 6 carbon atoms such as a vinyl group, an allyl group, a 1-propenyl group, an isopropenyl group, a 1-butenyl group, a 2-butenyl group, a 2-methylallyl group or the like; the term "$C_{2-6}$ alkynyl group" means a straight-chained or branched alkynyl group having 2 to 6 carbon atoms such as an ethynyl group, a 2-propynyl group or the like; the term "halogen atom" means a fluorine atom, a chlorine atom, a bromine atom or an iodine atom; and the term "hydroxy($C_{1-6}$ alkyl) group" means the above $C_{1-6}$ alkyl group substituted by a hydroxy group.

The term "$C_{1-6}$ alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like, preferably a straight-chained alkoxy group such as a propoxy group, a butoxy group or the like.

The term "$C_{3-8}$ cycloalkyl group" or "$C_{3-8}$ cycloalkyl" means a cyclopropyl group, a cyclobutyl group, a cyclopentyl group, a cyclohexyl group, a cycloheptyl group or a cyclooctyl group, preferably a cyclopentyl group, a cyclohexyl group or the like, The term "$C_{6-10}$ aryl group" or "$C_{6-10}$ aryl" means an aromacyclic hydrocarbon group having 6 or 10 carbon atoms such as a phenyl group, a naphthyl group or the like, preferably a phenyl group or the like (for example, examples of a $C_{6-10}$ aryl-$C_{1-6}$ alkyl group include a benzyl group, a phenylethyl group, a naphthylmethyl group, a naphthylethyl group or the like, preferably a benzyl group.

The term "3 to 10-membered cyclic heterocycloalkyl group" or "3 to 10-membered cyclic heterocycloalkyl" means a 3 to 10-membered monocyclic, polycyclic or bridged (for example, a 1-azabicyclo[2,2,2]octyl group, a 1,4-diazabicyclo[2,2,2]-octo-1-yl group or the like) heterocycloalkyl group having 1 or 2 hetero atoms selected from an oxygen atom, a sulfur atom or a nitrogen atom in the ring, which may have 1 or 2 oxo group such as an aziridinyl group, an azetidinyl group, a morpholino group, a 2-morpholinyl group, a thiomorpholinyl group, a pyrrolidino group, a piperidino group, a 4-piperidinyl group, a 1-piperazinyl group, a 2-oxopyrrolidin-1-yl group or the like or the above heterocycloalkyl group fused with a benzene ring (for example, a 1,3-dioxoisoindolin-2-yl group or the like), preferably a morpholino group, a 4-piperidinyl group, a 1-piperidinyl group, a 1-piperadinyl group, a 1-pyrrolidinyl group, a 1,3-dioxoisoindolin-2-yl group or the like.

The term "3 to 10-membered cyclic nitrogen-containing heterocycloalkyl group" means the above 3 to 10-membered cyclic heterocycloalkyl group containing at least one nitrogen atom in the ring.

The term "3 to 8-membered aliphatic cyclic amino group" means a 3 to 8-membered cyclic amino group which may contain any hetero atom other than the nitrogen atom at the binding position selected from an oxygen atom, a sulfur atom and nitrogen atom in the ring, such as an aziridinyl group, an azetidinyl group, a morpholino group, a thiomorpholinyl group, a pyrrolidinyl group, a piperadinyl group, a 2-oxopyrrolidin-1-yl group or the like, preferably a 4-piperidinyl group, a 1-piperidinyl group, a 1-piperadinyl group, a 1-pyrrolidinyl group or the like.

The term "5 to 10-membered cyclic heteroaryl group" or "5 to 10-membered cyclic heteroaryl" means a 5 or 6-membered cyclic aromatic heterocyclic group containing any 1 to 4 hetero atoms selected from an oxygen atom, a sulfur atom and a nitrogen atom in the ring, which is derived from thiazole, oxazole, isothiazole, isooxazole, pyridine, pyrimidine, pyrazine, pyridazine, pyrrole, furan, thiophene, imidazole, pyrazole, oxadiazole, thiadiazole, triazole, tetrazole, furazan or the like or a 5 or 6-membered cyclic aromatic heterocyclic group containing any 1 to 4 hetero atoms selected from an oxygen atom, a sulfur atom and a nitrogen atom in the ring, fused with a 6-membered ring, which is derived from indole, isoindole, benzofuran, isobenzofuran, benzothiophene, benzooxazole, benzothiazole, benzoisooxazole, benzoisothiazole, indazole, benzoimidazole, quinoline, isoquinoline, phthalazine, quinoxaline, quinazoline, sinoline, indolizine, naphthyridine, pteridine or the like.

The term "5 to 10-membered cyclic nitrogen-containing heteroaryl group" means the above 5 to 10-membered cyclic heteroaryl group containing at least one nitrogen atom in the ring, for example, preferably a group derived from pyridine, imidazole or the like.

As quaternary salts, a quaternary ammonium salt, a pyridinium salt, a piperadinium salt and the like can be illustrated. In addition, as anion ligands of the same, a fluoride, a chloride, a bromide, an iodide, a hydroxide, an acetate, a methanesulfonate, a trifluoromethanesulfonate, a p-toluenesulfonate, a sulfate, a tetrafluoroborate, a chlorochromate and the like can be illustrated, and an iodide, a hydroxide, an acetate, a methanesulfonate, a sulfate and the like are preferable.

In compounds represented by the above general formula (I) of the present invention, the above $R^1$, $R^2$ and $R^3$ preferably represent $OR^7$ and $R^7$ represents a substituent (N) having (i) or (k) selected from the above substituent group α, the substituent (N) represents more preferably an alkyl group having 3 or 4-carbon atoms. $R^3$, $R^4$ and $R^5$ preferably represent a hydrogen atom.

The representative manufacture methods of the compounds represented by the above general formula (I) of the present invention are illustrated by way of the following examples. However, they are not limited thereto.

Of compounds represented by the above general formula (I) of the present invention, a compound wherein n is 1 and $R^X$ and $R^Y$ represent a hydroxy group (Ia) can be prepared, for example, according to the following methods 1 to 3, other methods described in literatures or similar methods to the same or the like (for example, International publication No. WO97/25337 pamphlet, U.S. Pat. No. 6,204,249 gazette and U.S. Pat. No. 6,617,315 gazette). When a protective group is needed, any suitable introduction and elimination procedures can be optionally combined in the usual way.

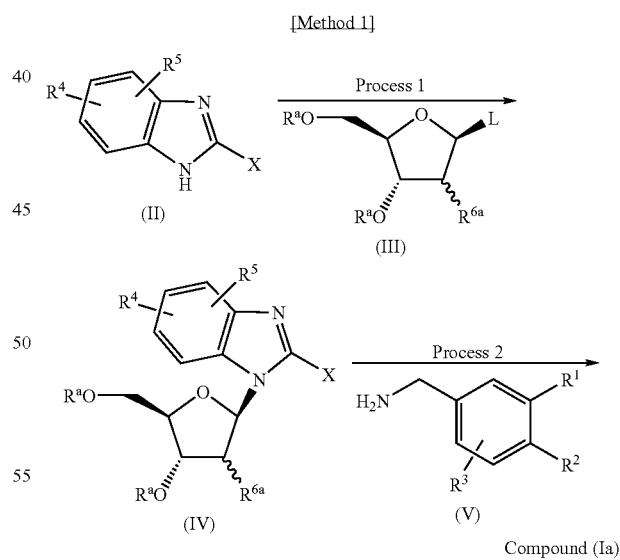

[Method 1]

Compound (Ia)

In the formula, $R^a$ independently represents a hydroxy-protective group, $R^{6a}$ represents a hydrogen atom or a hydroxy group having a protective group, L represents a leaving group such as a halogen atom, an acetoxy group or the like, X represents a leaving group such as a halogen atom, a toluenesulfonyloxy group or the like, $R^1$ to $R^5$ have the same meanings as defined above.

Process 1

1) In a case that the substituent L of a sugar donor represented by the above general formula (III) is a halogen atom such as a bromine atom, a compound represented by the above general formula (IV) can be prepared by subjecting a benzimidazole derivative represented by the above general formula (II) to glycosidation in the presence of a base such as sodium hydride, potassium carbonate or the like in an inert solvent, or 2) in a case that the substituent L of a sugar donor represented by the above general formula (III) is a leaving group such as an acetoxy group, a compound represented by the above general formula (IV) can be prepared by subjecting a benzimidazole derivative represented by the above general formula (II) to glycosidation in the presence of a Lewis acid such as trimethylsilyl trifluoromethanesulfonate, tin (IV) chloride, trifluoroborate or the like in an inert solvent after pretreatment using a silylating agent such as N,O-bis(trimethylsilyl)acetamide, trimethylsilyl chloride, hexamethyldisilazane or the like. As an inert solvent used in the glycosidation reaction, for example, N,N-dimethylacetamide, N,N-dimethylformamide, N-methylpyrrolidinone, dimethylsulfoxide, acetonitrile, 1,2-dichloroethane, tetrahydrofuran, a mixed solvent thereof or the like can be illustrated. The reaction temperature is usually from 0° C. to reflux temperature, and the reaction time is usually from 30 minutes to 1 day, varying based on a used starting material, solvent and reaction temperature.

Process 2

A compound represented by the above general formula (Ia) of the present invention can be prepared by subjecting a compound represented by the above general formula (IV) to condensation with a compound represented by the above general formula (V) in the presence or absence of a base such as sodium hydride, potassium carbonate, triethylamine, diisopropylethylamine or the like in an inert solvent, and optionally by removing a protective group of the sugar moiety or the like according to a method used in general organic synthesis such as alkaline hydrogenation or the like. As an inert solvent used in the condensation reaction, for example, toluene, tetrahydrofuran, dichloromethane, N,N-dimethylformamide, ethanol, isobutanol, water, a mixed solvent thereof or the like can be illustrated. The reaction temperature is usually from room temperature to reflux temperature, and the reaction time is usually from 1 hour to 3 days, varying based on a used starting material, solvent and reaction temperature.

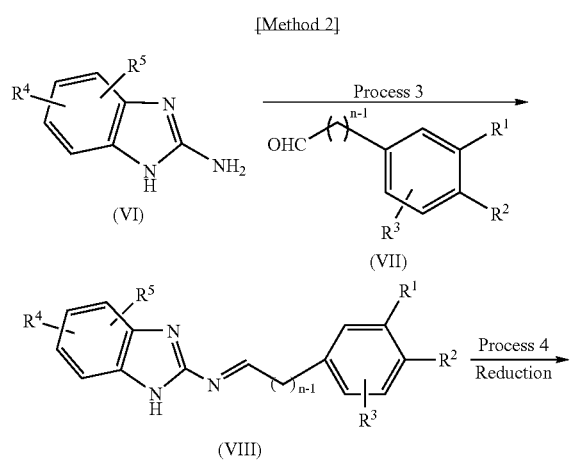

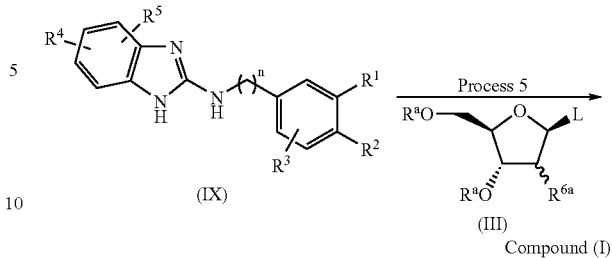

In the formula, L, $R^a$, $R^{6a}$, $R^1$ to $R^5$ and n have the same meanings as defined above.

Process 3

A compound represented by the above general formula (VIII) can be prepared by subjecting a 2-aminobenzimidazole derivative represented by the above general formula (VI) to condensation with an aldehyde compound represented by the above general formula (VII) in the presence or absence of a base such as sodium acetate, sodium carbonate, sodium ethoxide or the like or an acid such as acetic acid, methanesulfonic acid or the like in an inert solvent. As an inert solvent used in the condensation reaction, for example, toluene, tetrahydrofuran, dichloromethane, N,N-dimethylformamide, ethanol, water, a mixed solvent thereof or the like can be illustrated. The reaction temperature is usually from room temperature to reflux temperature, and the reaction time is usually from 10 minutes to 1 day, varying based on a used starting material, solvent and reaction temperature.

Process 4

A benzimidazole derivative represented by the above general formula (IX) can be prepared by reducing a compound represented by the above general formula (VIII) using a reducing agent such as lithium aluminum hydride, sodium borohydride or the like in an inert solvent. As an inert solvent used in the reduction reaction, for example, toluene, tetrahydrofuran, dichloromethane, a mixed solvent thereof or the like can be illustrated. The reaction temperature is usually from −78° C. to reflux temperature, and the reaction time is usually from 30 minutes to 1 day, varying based on a used starting material, solvent and reaction temperature.

Process 5

1) In a case that the substituent L of a sugar donor represented by the above general formula (III) is a halogen atom such as a bromine atom, a compound represented by the above general formula (I) of the present invention can be prepared by subjecting a benzimidazole derivative represented by the above general formula (IX) to glycosidation in the presence of a base such as sodium hydride, potassium carbonate or the like in an inert solvent, or 2) in a case that the substituent L of a sugar donor represented by the above general formula (III) is a leaving group such as an acetoxy group, a compound represented by the above general formula (I) of the present invention can be prepared by subjecting a benzimidazole derivative represented by the above general formula (IX) to glycosidation in the presence of a Lewis acid such as trimethylsilyl trifluoromethanesulfonate, tin (IV) chloride, trifluoroborate or the like in an inert solvent after pretreatment using a silylating agent such as N,O-bis(trimethylsilyl)acetamide, trimethylsilyl chloride, hexamethyldisilazane or the like, and optionally by removing a protective group of the sugar moiety or the like according to a method used in general organic synthesis such as alkaline hydrogenation or the like. As an inert solvent used in the glycosidation reaction, for example, N,N-dimethylacetamide, N,N-dimethylformamide, N-methylpyrrolidinone, dimethylsulfoxide, acetonitrile, 1,2-dichloroethane, tetrahydrofuran, a mixed solvent thereof or the like can be illustrated. The reaction temperature is usually from 0° C. to reflux temperature, and the reaction time is usually from 30 minutes to 1 day, varying based on a used starting material, solvent and reaction temperature.

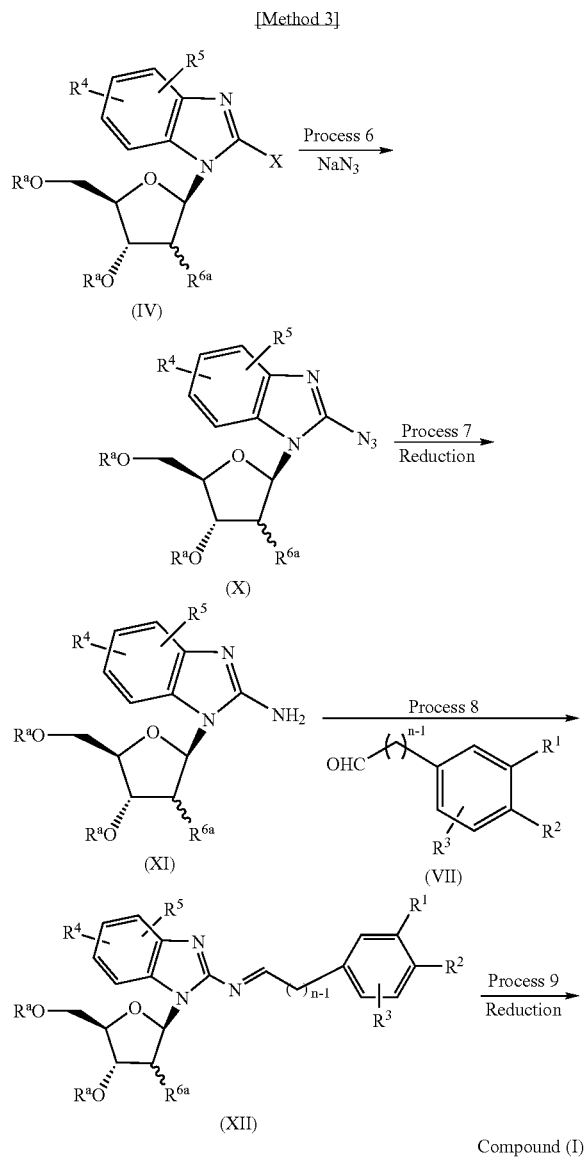

In the formula, X, $R^a$, $R^{6a}$, $R^1$ to $R^5$ and n have the same meanings as defined above.

Process 6

A compound represented by the above general formula (X) can be prepared by subjecting a compound represented by the above general formula (IV) to azidation using an aziding reagent such as sodium azide, lithium azide or the like in an inert solvent. As an inert solvent used in the azidation reaction, for example, toluene, tetrahydrofuran, dichloromethane, N,N-dimethylformamide, ethanol, isobutanol, water, a mixed solvent thereof or the like can be illustrated. The reaction temperature is usually from room temperature to reflux temperature, and the reaction time is usually from 1 hour to 3 days, varying based on a used starting material, solvent and reaction temperature.

Process 7

A compound represented by the above general formula (XI) can be prepared by subjecting a compound represented by the above general formula (X) to catalytic reduction using a metal catalyst such as palladium-carbon powder, platinum oxide or the like in the presence or absence of an acid such as hydrochloric acid in an inert solvent. As an inert solvent used in the catalytic reduction reaction, for example, methanol, ethanol, tetrahydrofuran, ethyl acetate, acetic acid, a mixed solvent thereof or the like can be illustrated. The reaction temperature is usually from room temperature to reflux temperature, and the reaction time is usually from 30 minutes to 1 day, varying based on a used starting material, solvent and reaction temperature.

Process 8

A compound represented by the above general formula (XII) can be prepared by subjecting a 2-aminobenzimidazole derivative represented by the above general formula (XI) to condensation with an aldehyde compound represented by the above general formula (VII) in the presence or absence of a base such as sodium acetate, sodium carbonate, sodium ethoxide or the like or an acid such as acetic acid, methanesulfonic acid or the like in an inert solvent. As an inert solvent used in the condensation reaction, for example, toluene, tetrahydrofuran, dichloromethane, N,N-dimethylformamide, ethanol, water, a mixed solvent thereof or the like can be illustrated. The reaction temperature is usually from room temperature to reflux temperature, and the reaction time is usually from 30 minutes to 1 day, varying based on a used starting material, solvent and reaction temperature.

Process 9

A compound represented by the above general formula (I) of the present invention can be prepared by subjecting compound represented by the above general formula (XII) to reduction using a reducing agent such as lithium aluminum hydride, sodium borohydride or the like, and optionally by removing the protective group at the sugar moiety or the like in accordance with a method used in general organic synthesis such as alkaline hydrogenation or the like in an inert solvent. As an inert solvent used in the reduction reaction, for example, toluene, tetrahydrofuran, dichloromethane, acetic acid, a mixed solvent thereof or the like can be illustrated. The reaction temperature is usually from −78° C. to reflux temperature, and the reaction time is usually from 30 minutes to 1 day, varying based on a used starting material, solvent and reaction temperature.

In addition, a compound represented by the above general formula (I) of the present invention can be also prepared, for example, in accordance with the following or similar method or in combination with the same. In a case that a protective group is necessary, introduction and removal procedures can be optionally combined in the usual way.

Among the compounds represented by the above general formula (I) of the present invention, a compound wherein at least one of $R^1$ to $R^3$ is $OR^7$, $SR^8$ or $NR^9R^{10}$ (with the proviso that at least one of $R^7$, $R^8$ and $R^9/R^{10}$ is not a hydrogen atom), or the above substituent (A) to (G) having $OR^{15}$, $SR^{16}$, $NR^{17}R^{18}$ or $NR^+R^DR^ER^F$ (with the proviso that at least one of $R^{15}$, $R^{16}$ and $R^{17}/R^{18}$ is not a hydrogen atom) can be prepared by subjecting a compound wherein the corresponding group is a hydroxy group, a thiol group or an amino group, or any of the above substituents (A) to (G) having a hydroxy group, a thiol group or an amino group to alkylation using an alkylating agent such as a corresponding halogenated alkyl compound or the like in the presence of a base such as sodium hydroxide, potassium carbonate, triethylamine, diisopropylethylamine or the like in an inert solvent optionally in the presence of a catalytic amount of sodium iodide. As an inert solvent used in the alkylation reaction, for example, methanol, ethanol, tetrahydrofuran, N,N-dimethylformamide, water, a mixed solvent thereof or the like can be illustrated. The reaction temperature is usually from room temperature to reflux temperature, and the reaction time is usually from 10 minutes to 1 day, varying based on a used starting material, solvent and reaction temperature.

Among the compounds represented by the above general formula (I) of the present invention, a compound wherein at least one of $R^1$ to $R^3$ is $OR^7$ or $COOR^{11}$ (with the proviso that neither $R^7$ nor $COOR^{11}$ is a hydrogen atom), or any of the above substituents (A) to (G) having $OR^{15}$ or $COOR^{19}$ (with the proviso that neither $R^{15}$ nor $R^{19}$ is not a hydrogen atom) can be prepared by subjecting a compound wherein the corresponding group is a hydroxy group or a carboxy group, or any of the above substituents (A) to (G) having a hydroxy group or a carboxy group to condensation using a corresponding alcohol compound in the presence of Mitsunobu reagent such as diethyl azodicarboxylate, diisopropyl azodicarboxylate or the like and an organic phosphorus reagent such as triphenylphosphine or the like in an inert solvent. As an inert solvent used in the condensation reaction, for example, toluene, tetrahydrofuran, N,N-dimethylformamide, a mixed solvent thereof or the like can be illustrated. The reaction temperature is usually from room temperature to reflux temperature, and the reaction time is usually from 10 minutes to 1 day, varying based on a used starting material, solvent and reaction temperature.

Among the compounds represented by the above general formula (I) of the present invention, a compound wherein at least one of $R^1$ to $R^3$ is $CONR^{12}R^{13}$, or any of the above substituents (A) to (G) having $CONR^{24}R^{25}$ can be prepared by subjecting an amine compound wherein the corresponding group is a carboxy group, or any of the above substituents (A) to (G) having a carboxy group to amidation, using a corresponding amine compound and a condensing agent such as diphenylphosphorylazide, dicyclohexylcarbodiimide or the like in an inert solvent, optionally in the presence of an activated esterifing reagent such as 1-hydroxybenzotriazole or the like. As an inert solvent used in the amidation reaction, for example, toluene, tetrahydrofuran, N,N-dimethylformamide, a mixed solvent thereof or the like can be illustrated. The reaction temperature is usually from room temperature to reflux temperature, and the reaction time is usually from 10 minutes to 1 day, varying based on a used starting material, solvent and reaction temperature.

Among the compounds represented by the above general formula (I) of the present invention, a compound wherein at least one of $R^1$ to $R^3$ is a $C_{2-6}$ alkenyl group or a $C_{2-6}$ alkynyl group can be prepared by subjecting a compound wherein the corresponding group is a halogen atom to condensation using a corresponding alkene or alkyne compound in the presence of a palladium catalyst such as palladium acetate or the like, an organic phosphorus ligand such as triphenylphosphine or the like and a base such as cesium carbonate, sodium tert-butoxide or the like in an inert solvent. As an inert solvent used in the condensation reaction, for example, toluene, tetrahydrofuran, N,N-dimethylformamide, a mixed solvent thereof or the like can be illustrated. The reaction temperature is usually from room temperature to reflux temperature, and the reaction time is usually from 10 minutes to 1 day, varying based on a used starting material, solvent and reaction temperature.

Among the compounds represented by the above general formula (I) of the present invention, a compound wherein at least one of $R^1$ to $R^3$ is a $C_{2-6}$ alkenyl group, a $C_{2-6}$ alkynyl group, a $C_{3-8}$ cycloalkyl group, a $C_{6-10}$ aryl group or a 5 to 10-membered cyclic heteroaryl group can be prepared by subjecting a compound wherein the corresponding group is a halogen atom to condensation with a corresponding boric acid compound in the presence of a base such as cesium carbonate, sodium tert-butoxide or the like and in the presence of a catalyst such as tetrakis(triphenylphosphine)palladium or the like and a ligand such as 2,2'-bis(diphenylphosphino)-1,1'-binaphthyl or the like in an inert solvent. As an inert solvent used in the condensation reaction, for example, toluene, tetrahydrofuran, N,N-dimethylformamide, a mixed solvent thereof or the like can be illustrated. The reaction temperature is usually from room temperature to reflux temperature, and the reaction time is usually from 10 minutes to 1 day, varying based on a used starting material, solvent and reaction temperature.

Among the compounds represented by the above general formula (I) of the present invention, a compound wherein at least one of $R^1$ to $R^3$ is a group having an acylamino group, an alkoxycarbonylamino group, a sulfonylamino group or an ureido group can be prepared by subjecting a compound having an amino group to reaction using an acylating agent such as a corresponding acylhalide derivative or the like, a carbamating agent such as chloroformate compound or the like, a sulfonylating agent such as a sulfonylhalide compound or the like, an agent to introduce into an ureide such as an isocyanate compound or the like in the presence or absence of a base such as sodium hydroxide, pyridine, triethylamine, diisopropylethylamine or the like in an inert solvent. As an inert solvent used in each reaction, for example, tetrahydrofuran, N,N-dimethylformamide, water, a mixed solvent thereof or the like can be illustrated. The reaction temperature is usually from room temperature to reflux temperature, and the reaction time is usually from 10 minutes to 1 day, varying based on a used starting material, solvent and reaction temperature.

Compounds represented by the above general formula (II) and (VI) used as a starting material in the above-mentioned production processes are commercially available or can be prepared in a known or similar method or the like, and the following method, for example, can be illustrated. In a case that a protective group is necessary, introduction or removal procedures can be optionally combined in the usual way.

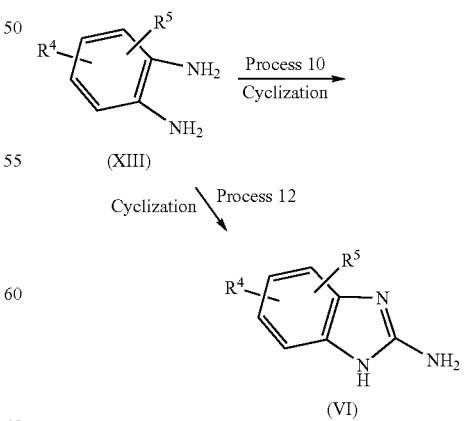

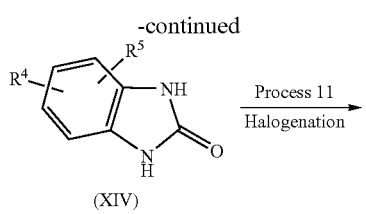

(XIV)

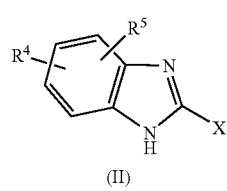

(II)

In the formula, X, $R^4$ and $R^5$ have the same meanings as defined above.

Process 10

A compound represented by the above general formula (XIV) can be prepared by subjecting a compound represented by the above general formula (XIII) to cyclization using a reagent such as phosgene, carbodiimidazole or the like in the presence or absence of a base such as sodium carbonate, triethylamine, pyridine or the like in an inert solvent. As an inert solvent used in the cyclization reaction, for example, tetrahydrofuran, dichloromethane, acetic acid, toluene, N,N-dimethylformamide, a mixed solvent thereof or the like can be illustrated. The reaction temperature is usually from 0° C. to reflux temperature, and the reaction time is usually from 10 minutes to 1 day, varying based on a used starting material, solvent and reaction temperature.

Process 11

A compound represented by the above general formula (II) can be prepared by subjecting a compound represented by the above general formula (XIV) to halogenation using an acid halogenating reagent such as thionylchloride, phosphorus trichloride, phosphorus pentachloride, phosphorus oxychloride, phosphorus tribromide, fluorosulfuric acid or the like without or in an inert solvent. As an inert solvent used in the halogenation reaction, for example, toluene, dichloromethane, a mixed solvent thereof or the like can be illustrated. The reaction temperature is usually from –78° C. to reflux temperature, and the reaction time is usually from 30 minutes to 1 day, varying based on a used starting material, solvent and reaction temperature.

Process 12

A compound represented by the above general formula (VI) can be prepared by subjecting a compound represented by the above general formula (XIII) to cyclization using a reagent such as cyanogen bromide or the like in an inert solvent. As an inert solvent used in the cyclization reaction, for example, tetrahydrofuran, dichloromethane, acetonitrile, toluene, a mixed solvent thereof or the like can be illustrated. The reaction temperature is usually from 0° C. to reflux temperature, and the reaction time is usually from 10 minutes to 1 day, varying based on a used starting material, solvent and reaction temperature.

Among the compounds represented by the above general formula (IX) used in the above-mentioned Method 2, a compound wherein n is 1 can be prepared in a known or similar method or the like, and the following method, for example, can be illustrated. In a case that a protective group is necessary, introduction or removal procedures can be optionally combined in the usual way.

[Method 5]

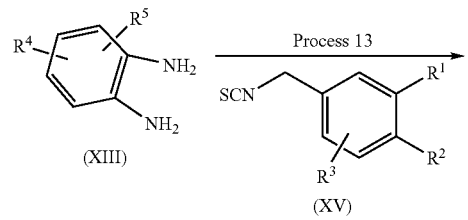

(XIII)            (XV)

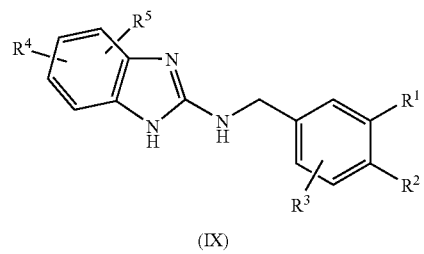

(IX)

In the formula, $R^1$ to $R^5$ have the same meanings as defined above.

Process 13

A compound represented by the above general formula (IX) can be prepared by allowing a compound represented by the above general formula (XIII) to react with a thioisocyanate derivative represented by the above general formula (XV) in the presence or absence of a base such as triethylamine, sodium carbonate, pyridine or the like without or in an inert solvent. As an inert solvent used in the reaction, for example, toluene, tetrahydrofuran, dichloromethane, N,N-dimethylformamide, ethanol, water, a mixed solvent thereof can be illustrated. The reaction temperature is usually from room temperature to reflux temperature, and the reaction time is usually from 10 minutes to 1 day, varying based on a used starting material, solvent and reaction temperature.

A compound represented by the above general formula (V) used as a starting material in the above-mentioned Method 1 is commercially available or can be prepared in a known or similar method or the like, and the following method, for example, can be illustrated. In a case that a protective group is necessary, introduction or removal procedures can be optionally combined in the usual way.

[Method 6]

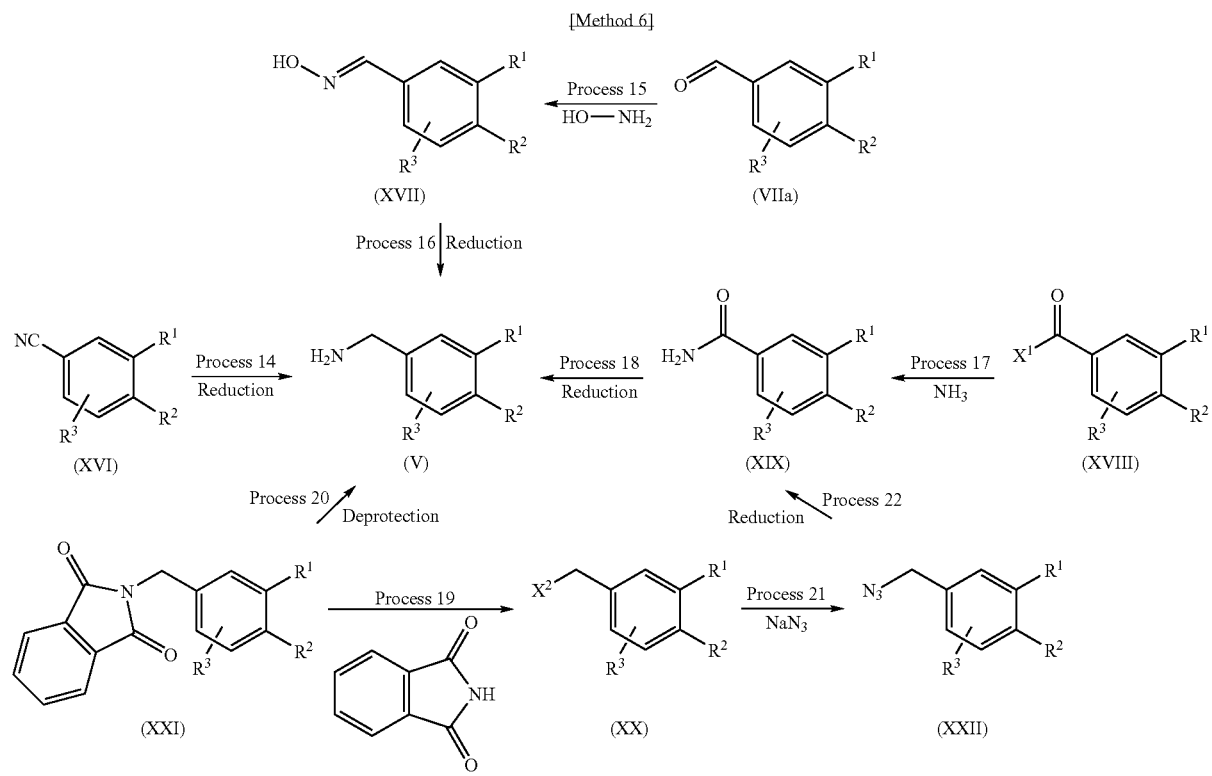

In the formula, $X^1$ represents a halogen atom, $X^2$ represents a halogen atom and $R^1$ to $R^3$ have the same meanings as defined above.

Process 14

A compound represented by the above general formula (V) can be prepared by subjecting a compound represented by the above general formula (XVI) according to a general reduction method of a nitrile, for example, 1) to reduction using a reducing agent such as lithium aluminum hydride, diisobutylaluminum hydride or the like in an inert solvent, or 2) to catalytic reduction using a metal catalyst such as palladium-carbon powder, platinum oxide or the like in the presence or absence of an acid such as hydrochloric acid or the like in an inert solvent. As a solvent used in the reduction reaction 1), for example, toluene, tetrahydrofuran, dichloromethane, a mixed solvent thereof or the like can be illustrated. The reaction temperature is usually from −78° C. to reflux temperature, and the reaction time is usually from 30 minutes to 1 day, varying based on a used starting material, solvent and reaction temperature. As a solvent used in the reduction reaction 2), methanol, ethanol, tetrahydrofuran, ethyl acetate, acetic acid, a mixed solvent thereof or the like can be illustrated. The reaction temperature is usually from room temperature to reflux temperature, and the reaction time is usually from 30 minutes to 1 day, varying based on a used starting material, solvent and reaction temperature.

Process 15

A corresponding oxime represented by the above general formula (XVII) can be prepared by allowing a compound represented by the above general formula (VIIa) to react with hydroxylamine in an inert solvent. As an inert solvent used in the reaction, for example, toluene, tetrahydrofuran, dichloromethane, a mixed solvent thereof or the like can be illustrated. The reaction temperature is usually from −78° C. to reflux temperature, and the reaction time is usually from 30 minutes to 1 day, varying based on a used starting material, solvent and reaction temperature.

Process 16

A compound represented by the above general formula (V) can be prepared by subjecting a compound represented by the above general formula (XVII) according to a general reduction method of an oxime, for example, 1) to reduction using a reducing agent such as lithium aluminum hydride, diisobutylaluminum hydride or the like in an inert solvent, or 2) to catalytic reduction using a metal catalyst such as palladium-carbon powder, platinum oxide or the like in the presence or absence of an acid such as hydrochloric acid or the like in an inert solvent. As a solvent used in the reduction reaction 1), for example, toluene, tetrahydrofuran, dichloromethane, a mixed solvent thereof or the like can be illustrated. The reaction temperature is usually from −78° C. to reflux temperature, and the reaction time is usually from 30 minutes to 1 day, varying based on a used starting material, solvent and reaction temperature. As a solvent used in the reduction reaction 2), methanol, ethanol, tetrahydrofuran, ethyl acetate, acetic acid, a mixed solvent thereof or the like can be illustrated. The reaction temperature is usually from room temperature to reflux temperature, and the reaction time is usually from 30 minutes to 1 day, varying based on a used starting material, solvent and reaction temperature.

Process 17

A compound represented by the above general formula (XIX) can be prepared by allowing a compound represented by the above general formula (XVIII) to react with ammonia without or in an inert solvent. As an inert solvent used in the reaction, for example, toluene, dichloromethane, a mixed solvent thereof or the like can be illustrated. The reaction temperature is usually from −78° C. to reflux temperature, and the reaction time is usually from 30 minutes to 1 day, varying based on a used starting material, solvent and reaction temperature.

Process 18

A compound represented by the above general formula (V) can be prepared by subjecting a compound represented by the above general formula (XIX) according to a general reduction method of a carbamoyl group, for example, to reduction using a reducing agent such as borane-dimethylsulfide complex, borane-tetrahydrofuran complex, lithium aluminum hydride, diisobutylaluminum hydride or the like in an inert solvent. As an inert solvent used in the reduction reaction, for example, toluene, tetrahydrofuran, dichloromethane, a mixed solvent thereof or the like can be illustrated. The reaction temperature is usually from −78° C. to reflux temperature, and the reaction time is usually from 30 minutes to 1 day, varying based on a used starting material, solvent and reaction temperature.

Process 19

A compound represented by the above general formula (XXI) can be prepared by allowing a compound represented by the above general formula (XX) to react with a phthalimide or a salt thereof in the presence or absence of a base such as sodium hydride, sodium carbonate, potassium hydroxide or the like in an inert solvent. As an inert solvent used in the reaction, for example, toluene, tetrahydrofuran, dichloromethane, N,N-dimethylformamide, ethanol, a mixed solvent thereof or the like can be illustrated. The reaction temperature is usually from room temperature to reflux temperature, and the reaction time is usually from 10 minutes to 1 day, varying based on a used starting material, solvent and reaction temperature.

Process 20

A compound represented by the above general formula (V) can be prepared by subjecting a compound represented by the above general formula (XXI) according to a general deprotection method of a phthalimide, for example, to deprotection using methylamine, hydrazine or the like in an inert solvent. As an inert solvent used in the deprotection reaction, for example, toluene, tetrahydrofuran, a mixed solvent thereof or the like can be illustrated. The reaction temperature is usually from −78° C. to reflux temperature, and the reaction time is usually from 30 minutes to 1 day, varying based on a used starting material, solvent and reaction temperature.

Process 21

A compound represented by the above general formula (XXII) can be prepared by allowing a compound represented by the above general formula (XX) to react with an azidating reagent such as sodium azide, lithium azide or the like in an inert solvent. As an inert solvent used in the azidation reaction, for example, toluene, tetrahydrofuran, N,N-dimethylformamide, ethanol, a mixed solvent thereof or the like can be used. The reaction temperature is usually from room temperature to reflux temperature, and the reaction time is usually from 10 minutes to 1 day, varying based on a used starting material, solvent and reaction temperature.

Process 22

A compound represented by the above general formula (V) can be prepared by subjecting a compound represented by the above general formula (XXII) according to a general reduction method of an azide, for example, 1) to reduction using a reducing agent such as lithium aluminum hydride, diisobutylaluminum hydride or the like in an inert solvent, or 2) to catalytic reduction using a metal catalyst such as palladium-carbon powder, platinum oxide or the like in the presence or absence of an acid such as hydrochloric acid or the like in an inert solvent. As an inert solvent used in the reduction reaction 1), for example, toluene, tetrahydrofuran, dichloromethane, a mixed solvent thereof or the like can be illustrated. The reaction temperature is usually from −78° C. to reflux temperature, and the reaction time is usually from 30 minutes to 1 day, varying based on a used starting material, solvent and reaction temperature. As a solvent used in the reduction reaction 2), for example, methanol, ethanol, tetrahydrofuran, ethyl acetate, acetic acid, a mixed solvent thereof or the like can be illustrated. The reaction temperature is usually from room temperature to reflux temperature, and the reaction time is usually from 30 minutes to 1 day, varying based on a used starting material, solvent and reaction temperature.

Among the compounds of the above general formula (VII) used in the above-mentioned Method 2 or 3, a compound represented by a general formula (VIIa) wherein n is 1 and a compound represented by the above general formula (XVI), (XVIII) or (XX) used in Method 6 is commercially available or can be prepared in a known or similar method or the like (J. Med. Chem., Vol. 46, pp. 1845-1857, 2003; Synthesis, Vol. 17, pp. 2503-2512, 2002 or the like), and as the preparation methods, the following Methods 7 to 10, for example, can be illustrated. In a case that a protective group is necessary, introduction or removal procedures can be optionally combined in the usual way.

[Method 7]

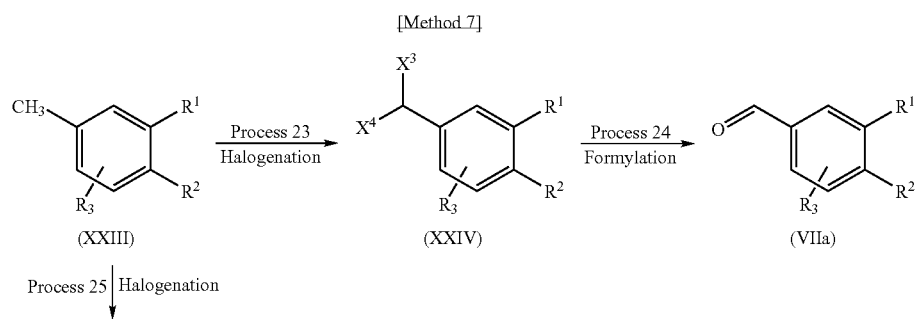

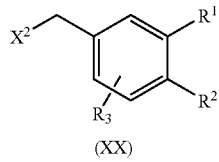

(XX)

In the formula, $X^3$ and $X^4$ represent a halogen atom, and $R^1$ to $R^3$ and $X^3$ have the same meanings as defined above.

Process 23

A compound represented by the above general formula (XXIV) can be prepared by subjecting a compound represented by the above general formula (XXIII) to halogenation using a halogenating reagent such as N-chlorosuccinimide, N-bromosuccinimide or the like, and optionally using an initiating agent such as benzoyl peroxide, α,α'-azobisisobutylonitrile or the like in an inert solvent. As an inert solvent used in the halogenation reaction, for example, tetrahydrofuran, dichloromethane, acetic acid, toluene, N,N-dimethylformamide, a mixed solvent thereof or the like can be illustrated. The reaction temperature is usually from 0° C. to reflux temperature, and the reaction time is usually from 10 minutes to 1 day, varying based on a used starting material, solvent and reaction temperature.

by treating the same with an aqueous solution of hydrochloric acid or nitric acid. The reaction temperature is usually from room temperature to reflux temperature, and the reaction time is usually from 1 hour to 1 day, varying based on a used starting material, solvent and reaction temperature.

Process 25

A compound represented by the above general formula (XX) can be prepared by subjecting a compound represented by the above general formula (XXIII) to halogenation using a halogenating reagent such as N-chlorosuccinimide, N-bromosuccinimide or the like, and optionally using an initiating agent such as benzoyl peroxide, α,α'-azobisisobutylonitrile or the like in an inert solvent. As an inert solvent used in the halogenation reaction, for example, tetrahydrofuran, dichloromethane, acetic acid, toluene, N,N-dimethylformamide, a mixed solvent thereof or the like can be illustrated. The reaction temperature is usually from 0° C. to reflux temperature, and the reaction time is usually from 10 minutes to 1 day, varying based on a used starting material, solvent and reaction temperature.

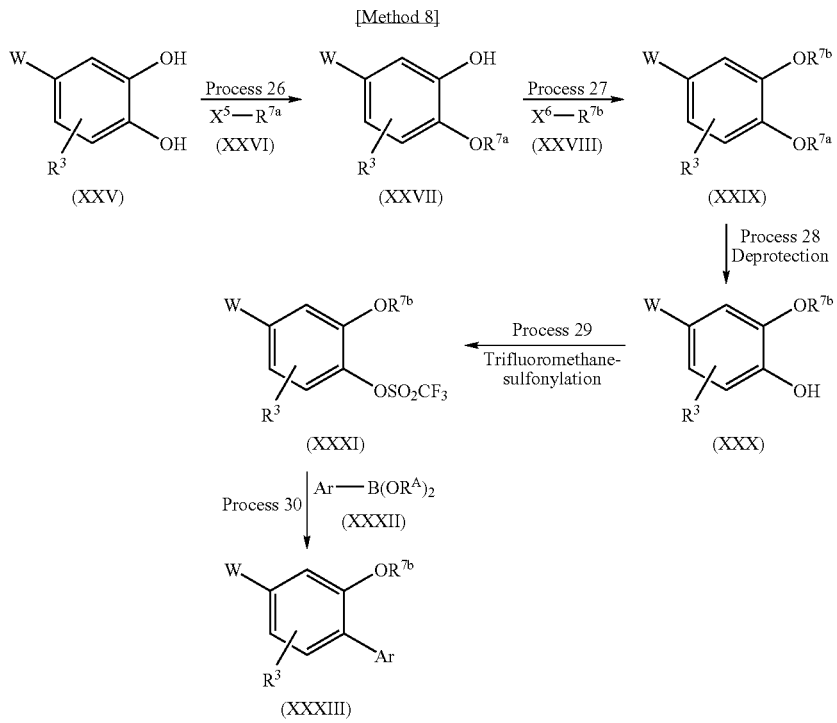

[Method 8]

Process 24

A formyl compound represented by the above general formula (VIIa) can be prepared by allowing a compound represented by the above general formula (XXIV) to react with a reagent such as silver nitrate or the like in methanol and then In the formula, $R^{7a}$ represents a hydroxy-protective group or has the same meaning to $R^7$; $R^{7b}$ has the same meaning to $R^7$; $X^5$ and $X^6$ independently represent a halogen atom; Ar represents a $C_{2-6}$ alkenyl group, a $C_{2-6}$ alkynyl group, a $C_{3-8}$ cycloalkyl group, a $C_{6-10}$ aryl group or a 5 to 10-membered cyclic heteroaryl group; $R^4$ represents a hydrogen atom or a $C_{1-6}$ alkyl group; W represents a formyl group, a cyano group or a carbamoyl group; and $R^3$ has the same meaning as defined above.

Process 26

A compound represented by the above general formula (XXVII) can be prepared by subjecting a compound represented by the above general formula (XXV) to O-alkylation using an alkylating agent or an agent to introduce a hydroxy-protective group represented by the above general formula (XXVI) in the presence of a base such as sodium hydroxide, potassium carbonate, triethylamine, diisopropylethylamine or the like, optionally in the presence of a catalytic amount of sodium iodide in an inert solvent. As an agent to introduce a hydroxy-protective group, benzyl bromide, chloromethylmethyl ether or the like can be illustrated. As an inert solvent used in the O-alkylation reaction, for example, methanol, ethanol, tetrahydrofuran, N,N-dimethylformamide, water, a mixed solvent thereof or the like can be illustrated. The reaction temperature is usually from room temperature to reflux temperature, and the reaction time is usually from 10 minutes to 1 day, varying based on a used starting material, solvent and reaction temperature.

Process 27

A compound represented by the above general formula (XXIX) can be prepared by subjecting a compound represented by the above general formula (XXVII) to O-alkylation using an alkylating agent represented by the above general formula (XXVIII) in the presence of a base such as sodium hydroxide, potassium carbonate, triethylamine, diisopropylethylamine or the like, optionally in the presence of a catalytic amount of sodium iodide in an inert solvent. As an inert solvent used in the O-alkylation reaction, for example, methanol, ethanol, tetrahydrofuran, N,N-dimethylformamide, water, a mixed solvent thereof or the like can be illustrated. The reaction temperature is usually from room temperature to reflux temperature, and the reaction time is usually from 10 minutes to 1 day, varying based on a used starting material, solvent and reaction temperature.

Process 28

A compound represented by the above general formula (XXX) can be prepared by removing a hydroxy-protective group of a compound represented by the above general formula (XXIX) wherein $R^{7a}$ represents a hydroxy-protective group in the usual way. For example, in a case that the protective group is a benzyl group, a compound represented by the above general formula (XXX) can be prepared by catalytic reduction using a metal catalyst such as palladium-carbon powder or the like in the presence or absence of an acid such as hydrochloric acid or the like in an inert solvent. As an inert solvent used in the catalytic reduction reaction, for example, methanol, ethanol, tetrahydrofuran, ethyl acetate, acetic acid, a mixed solvent thereof or the like can be illustrated. The reaction temperature is usually from room temperature to reflux temperature, and the reaction time is usually from 30 minutes to 1 day, varying based on a used starting material, solvent and reaction temperature.

Process 29

A compound represented by the above general formula (XXXI) can be prepared by allowing a compound represented by the above general formula (XXX) to react with a reagent to drive into a trifluoromethanesulfonyl compound such as trifluoromethanesulfonic anhydride or the like in the presence of a base such as pyridine, triethylamine, diisopropylethylamine or the like in an inert solvent. As an inert solvent used in the reaction, for example, toluene, tetrahydrofuran, N,N-dimethylformamide, dichloromethane, a mixed solvent thereof or the like can be illustrated. The reaction temperature is usually from 0° C. to reflux temperature, and the reaction time is usually from 10 minutes to 1 day, varying based on a used starting material, solvent and reaction temperature.

Process 30

A compound-represented by the above general formula (XXXIII) can be prepared by subjecting a compound represented by the above general formula (XXXI) to condensation with a boric acid compound represented by the above general formula (XXXII) using a catalyst such as tris(dibenzylidenacetone) dipalladium or the like and a ligand such as 2,2'-bis(diphenylphosphino)-1,1'-binaphthyl or the like in the presence of a base such as cesium carbonate, sodium tert-butoxide or the like in an inert solvent. As an inert solvent used in the condensation reaction, for example, N,N-dimethylacetamide, toluene, tetrahydrofuran, a mixed solvent thereof or the like can be illustrated. The reaction temperature is usually from room temperature to reflux temperature, and the reaction time is usually from 1 hour to 1 day, varying based on a used starting material, solvent and reaction temperature.

In the Method 8, an example is described regarding a compound wherein $R^1$ represents $OR^7$. A raw material of a compound represented by the above general formula (I) wherein at least one of $R^1$ to $R^3$ has $SR^8$ or $NR^9R^{10}$ can be also prepared in a similar or known method described in literatures or the like (for example, a method by Melvin et. al.: Journal of Organic Chemistry, 31, pp. 3980-3984, 1996) (similarly in the following Methods 9 and 10). In addition, in a case that a protective group is necessary in a compound wherein $R^1$ represents $NR^9NR^{10}$, introduction and removal procedures can be optionally combined in the usual way.

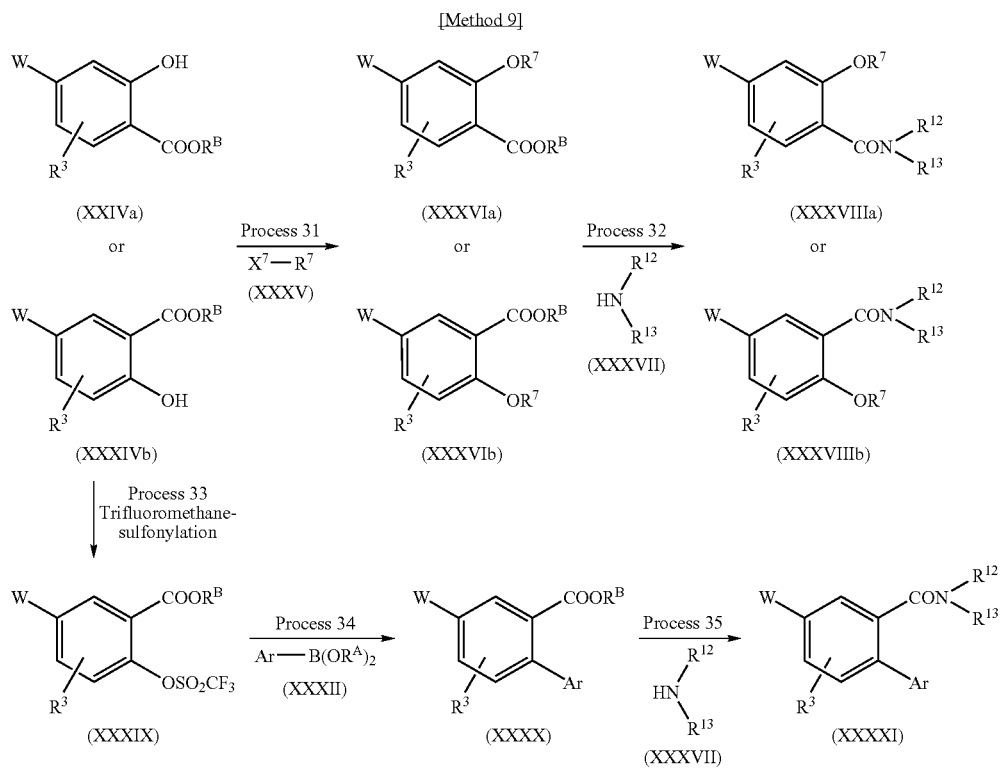

[Method 9]

In the formula, $R^8$ represents a $C_{1-6}$ alkyl group; $X^7$ represents a halogen atom; and Ar, $R^4$, $R^3$, $R^7$, $R^{12}$, $R^{13}$ and W have the same meaning as defined above.

Process 31

A compound represented by the above general formula (XXXVIa) or (XXXVIb) can be prepared by subjecting a compound represented by the above general formula (XXXIVa) or (XXXIVb) to O-alkylation using an alkylating agent represented by the above general formula (XXXV) in the presence of a base such as sodium hydroxide, potassium carbonate, triethylamine, diisopropylethylamine or the like, optionally in the presence of a catalytic amount of sodium iodide in an inert solvent. As an inert solvent used in the O-alkylation reaction, for example, methanol, ethanol, tetrahydrofuran, N,N-dimethylformamide, water, a mixed solvent thereof or the like can be illustrated. The reaction temperature is usually from room temperature to reflux temperature, and the reaction time is usually from 10 minutes to 1 day, varying based on a used starting material, solvent and reaction temperature.

Process 32

A compound represented by the above general formula (XXXVIIIa) or (XXXVIIIb) can be prepared: method 1) by deriving a compound represented by the above general formula (XXXVIa) or (XXXVIb) into a corresponding carbonic acid by a general alkaline hydrogenation, allowing to react with an activated esterifing reagent such as diphenylphosphoryladize or the like in the presence of a base such as triethylamine or the like, and then condensing with a corresponding amine represented by the above general formula (XXXVII) in an inert solvent, or method 2) by allowing a corresponding amine represented by the above general formula (XXXVII) to react with an activating agent such as trimethylaluminum or the like and then to react with a compound represented by the above general formula (XXXVIa) or (XXXVIb) in an inert solvent. As an inert solvent used in the condensation reaction in method 1), for example, tetrahydrofuran, N,N-dimethylformamide, a mixed solvent thereof or the like can be illustrated. As an inert solvent used in the condensation reaction in method 2), for example, toluene, tetrahydrofuran or the like can be illustrated. The reaction temperature for both reactions is usually from room temperature to reflux temperature, and the reaction time is usually from 10 minutes to 1 day, varying based on a used starting material, solvent and reaction temperature.

Process 33

A compound represented by the above general formula (XXXIX) can be prepared by allowing a compound represented by the above general formula (XXXIVb) to react with a reagent to drive into a trifluoromethanesulfonyl compound such as trifluoromethanesulfonic anhydride or the like in the presence of a base such as pyridine, triethylamine, diisopropylethylamine or the like in an inert solvent. As an inert solvent used in the reaction, for example, toluene, tetrahydrofuran, N,N-dimethylformamide, dichloromethane, a mixed solvent thereof or the like can be illustrated. The reaction temperature is usually from 0° C. to reflux temperature, and the reaction time is usually from 10 minutes to 1 day, varying based on a used starting material, solvent and reaction temperature.

Process 34

A compound represented by the above general formula (XXXX) can be prepared by subjecting a compound represented by the above general formula (XXXIX) to condensation with a boric acid compound represented by the above general formula (XXXII) using a catalyst such as tris(dibenzylidenacetone) dipalladium or the like and a ligand such as 2,2'-bis(diphenylphosphino)-1,1'-binaphthyl or the like in the presence of a base such as cesium carbonate, sodium tert-butoxide or the like in an inert solvent. As an inert solvent used in the condensation reaction, for example, N,N-dimethylacetamide, toluene, tetrahydrofuran, a mixed solvent thereof or the like can be illustrated. The reaction temperature is usually from room temperature to reflux temperature, and the reaction time is usually from 1 hour to 1 day, varying based on a used starting material, solvent and reaction temperature.

Process 35

A compound represented by the above general formula (XXXXI) can be prepared: method 1) by deriving a compound represented by the above general formula (XXXX) into a corresponding carbonic acid by a general alkaline hydrogenation, allowing to react with an activated esterifing reagent such as diphenylphosphoryladize or the like in the presence of a base such as triethylamine or the like, and then condensing with a corresponding amine represented by the above general formula (XXXVII) in an inert solvent, or method 2) by allowing a corresponding amine represented by the above general formula (XXXVII) to react with an activating agent such as trimethylaluminum or the like and then to react with a compound represented by the above general formula (XXXX) in an inert solvent. As an inert solvent used in the condensation reaction in method 1), for example, tetrahydrofuran, N,N-dimethylformamide, a mixed solvent thereof or the like can be illustrated. As an inert solvent used in the condensation reaction in method 2), for example, toluene, tetrahydrofuran or the like can be illustrated. The reaction temperature for both reactions is usually from room temperature to reflux temperature, and the reaction time is usually from 10 minutes to 1 day, varying based on a used starting material, solvent and reaction temperature.

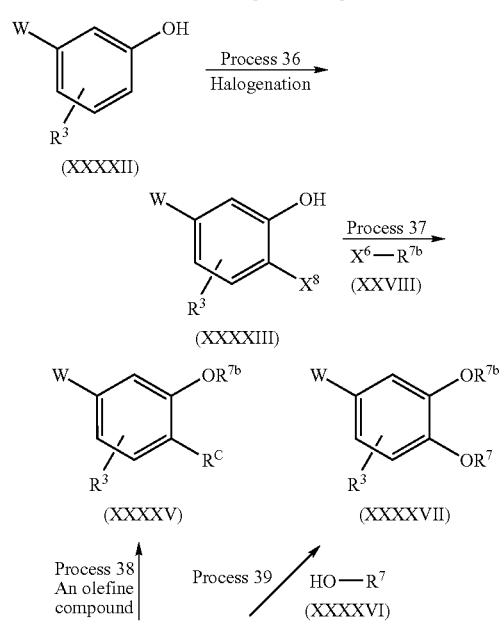

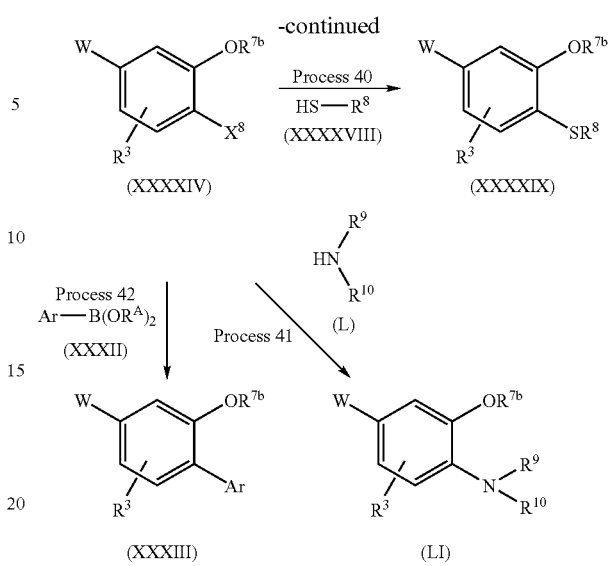

In the formula, $R^C$ represents a 1-alkenyl group; $X^8$ represents a halogen atom; and Ar, $R^4$, $R^3$, $R^7$, $R^{7b}$, $R^8$, $R^9$, $R^{10}$ and W have the same meaning as defined above.

Process 36

A compound represented by the above general formula (XXXXIII) can be prepared by allowing a compound represented by the above general formula (XXXXII) to react with a halogenating reagent such as iodine monochloride or the like in the presence or absence of an acid such as acetic acid or the like, in an inert solvent. As an inert solvent used in the halogenation reaction, for example, toluene, acetic acid, N,N-dimethylformamide, dichloromethane, a mixed solvent thereof or the like can be used. The reaction temperature is usually from room temperature to reflux temperature, and the reaction time is usually from 10 minutes to 1 day, varying based on a used starting material, solvent and reaction temperature.

Process 37

A compound represented by the above general formula (XXXXIV) can be prepared by subjecting a compound represented by the above general formula (XXXXIII) to O-alkylation using an alkylating agent represented by the above general formula (XXVIII) in the presence of a base such as sodium hydroxide, potassium carbonate, triethylamine, diisopropylethylamine or the like, optionally in the presence of a catalytic amount of sodium iodide in an inert solvent. As an inert solvent used in the O-alkylation reaction, for example, methanol, ethanol, tetrahydrofuran, N,N-dimethylformamide, water, a mixed solvent thereof or the like can be illustrated. The reaction temperature is usually from room temperature to reflux temperature, and the reaction time is usually from 10 minutes to 1 day, varying based on a used starting material, solvent and reaction temperature.

Process 38

A compound represented by the above general formula (XXXXV) can be prepared by allowing a compound represented by the above general formula (XXXXIV) to react with an olefine compound using a catalyst such as tris(dibenzylidenacetone) dipalladium or the like and a ligand such as 2,2'-bis(diphenylphosphino)-1,1'-binaphthyl or the like in the presence of a base such as cesium carbonate, sodium tert-butoxide or the like in an inert solvent. As an inert solvent used in the alkenylating reaction, for example, N,N-dimethylacetamide, toluene, tetrahydrofuran, a mixed solvent thereof or the like can be illustrated. The reaction temperature is usually from room temperature to reflux temperature, and the reaction time is usually from 1 hour to 1 day, varying based on a used starting material, solvent and reaction temperature.

Process 39

A compound represented by the above general formula (XXXXVII) can be prepared by subjecting a compound represented by the above general formula (XXXXIV) to condensation with an alcohol compound represented by the above general formula (XXXXVI) in the presence or absence of a base such as sodium hydride, potassium carbonate or the like in an inert solvent. As an inert solvent used in the condensation reaction, for example, N,N-dimethylacetamide, toluene, tetrahydrofuran, a mixed solvent thereof or the like can be illustrated. The reaction temperature is usually from room temperature to reflux temperature, and the reaction time is usually from 1 hour to 1 day, varying based on a used starting material, solvent and reaction temperature.

Process 40

A compound represented by the above general formula (XXXXIX) can be prepared by subjecting a compound represented by the above general formula (XXXXIV) to condensation with a thiol compound represented by the above general formula (XXXXVIII) in the presence or absence of a base such as sodium hydride, potassium carbonate or the like in an inert solvent. As an inert solvent used in the condensation reaction, for example, N,N-dimethylacetamide, toluene, tetrahydrofuran, a mixed solvent thereof or the like can be illustrated. The reaction temperature is usually from room temperature to reflux temperature, and the reaction time is usually from 1 hour to 1 day, varying based on a used starting material, solvent and reaction temperature.

Process 41

A compound represented by the above general formula (LI) can be prepared by subjecting a compound represented by the above general formula (XXXXIV): method 1) to condensation with an amine compound represented by the above general formula (L) in the presence or absence of a base such as sodium hydride, potassium carbonate or the like in an inert solvent, or method 2) to condensation with an amine compound represented by the above general formula (L) using a catalyst such as tris(dibenzylidenacetone) dipalladium or the like and a ligand such as 2,2'-bis(diphenylphosphino)-1,1'-binaphthyl or the like in the presence of a base such as cesium carbonate, sodium tert-butoxide or the like in an inert solvent. As an inert solvent used in the Method 1), for example, N,N-dimethylacetamide, toluene, tetrahydrofuran, a mixed solvent thereof or the like can be illustrated. The reaction temperature is usually from room temperature to reflux temperature, and the reaction time is usually from 1 hour to 1 day, varying based on a used starting material, solvent and reaction temperature. In addition, as an inert solvent used in the Method 2), for example, N,N-dimethylacetamide, toluene, tetrahydrofuran, a mixed solvent thereof or the like can be illustrated. The reaction temperature is usually from room temperature to reflux temperature, and the reaction time is usually from 1 hour to 1 day, varying based on a used starting material, solvent and reaction temperature.

Process 42

A compound represented by the above general formula (XXXIII) can be prepared by subjecting a compound represented by the above general formula (XXXXIV) to condensation with a compound represented by the above general formula (XXXII) using a catalyst such as tris(dibenzylidenacetone) dipalladium or the like and a ligand such as 2,2'-bis(diphenylphosphino)-1,1'-binaphthyl or the like in the presence of a base such as cesium carbonate, sodium tert-butoxide or the like in an inert solvent. As an inert solvent used in the condensation reaction, for example, N,N-dimethylacetamide, toluene, tetrahydrofuran, a mixed solvent thereof or the like can be illustrated. The reaction temperature is usually from room temperature to reflux temperature, and the reaction time is usually from 1 hour to 1 day, varying based on a used starting material, solvent and reaction temperature.

[Method 11]

Among the compounds represented by the above general formula (VII) used as starting materials in the above-mentioned Methods 2 and 3, a compound (VIIb) wherein n is 2 is commercially available or can be prepared in a known or similar method or the like, and the following method, for example, can be illustrated.

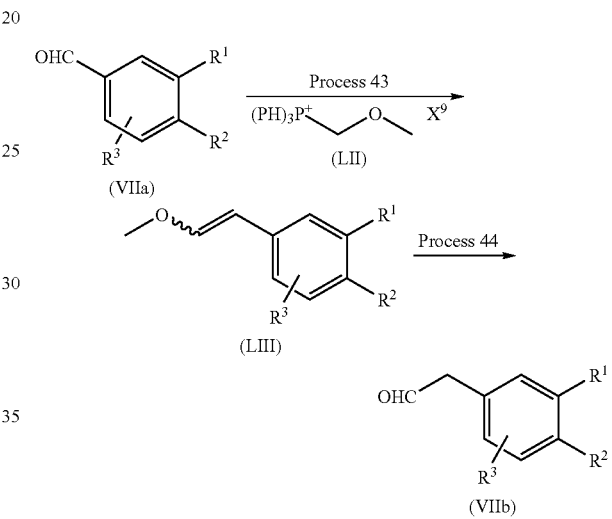

In the formula, Ph represents a phenyl group; $X^9$ represents a halogen ion; and $R^1$, $R^2$, $R^3$ have the same meanings as defined above.

Process 43

A compound represented by the above general formula (LIII) can be prepared by subjecting a compound represented by the above general formula (VIIa) to condensation with a compound represented by the above general formula (LII) in the presence of a base such as sodium hydride, potassium tert-butoxide, n-butyllithium, lithium bis(trimethylsilyl)amide, sodium bis(trimethylsilyl)amide, sodium hydroxide or the like in an inert solvent. As an inert solvent used in the reaction, for example, tetrahydrofuran, dimethylsulfoxide, N,N-dimethylformamide, N,N-dimethylacetamide, N-methylpyrrolidinone, 1,3-dimethyl-2-imidazolidinone, acetonitrile, a mixed solvent thereof or the like can be illustrated. The reaction temperature is usually from −78° C. to reflux temperature, and the reaction time is usually from 30 minutes to 1 day, varying based on a used starting material, solvent and reaction temperature.

Process 44

A compound represented by the above general formula (VIIb) can be prepared by subjecting a compound represented by the above general formula (LIII) to hydrogenation in the presence of an acid such as hydrochloric acid, sulfuric acid, methanesulfonic acid, p-toluenesulfonic acid, pyridinium p-toruenesulfonate or the like. As a solvent used in the reaction, for example, tetrahydrofuran, acetone, acetonitrile, water, a mixed solvent thereof or the like can be illustrated. The reaction temperature is usually from 0° C. to reflux temperature, and the reaction time is usually from 30 minutes to 1 day, varying based on a used starting material, solvent and reaction temperature.

organic syntheses can be used. For example, as a hydroxy-protective group, a p-methoxybenzyl group, a benzyl group, a methoxymethyl group, an acetyl group, a pivaroyl group, a benzoyl group, a tert-butyldimethylsilyl group, a tert-butyldiphenylsilyl group, an aryl group and the like, in addition, in a case that there are two neighboring hydroxy groups, an isopropylidene group, a cyclopentylidene group, a cyclo-

[Method 12]

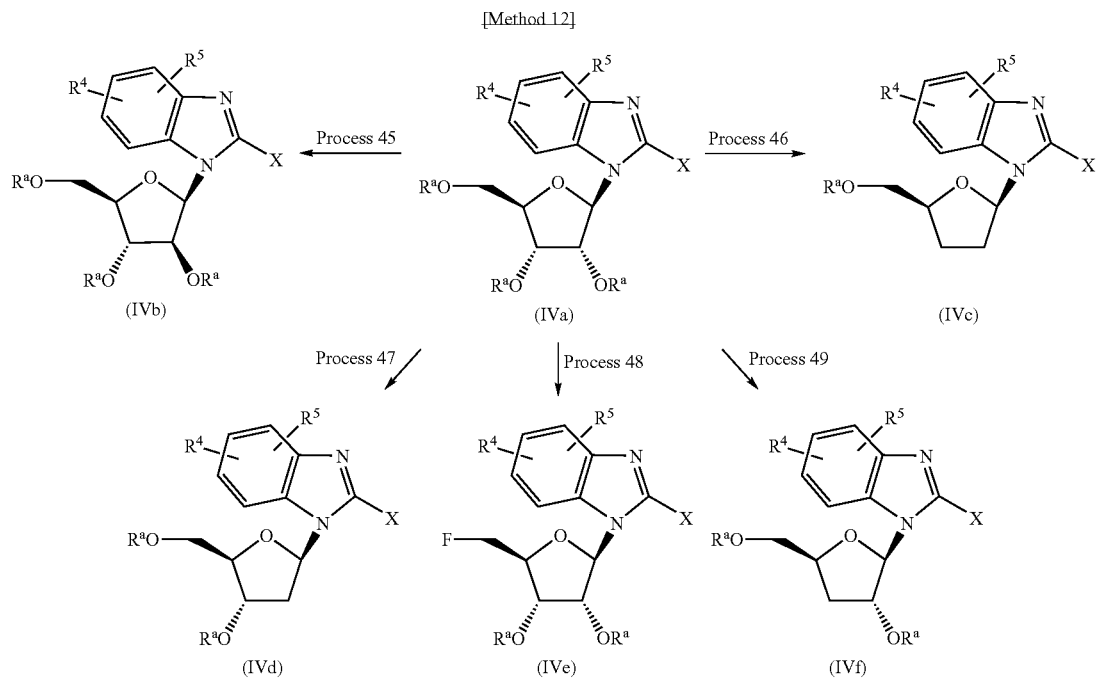

In the formula, X, $R^a$, $R^4$, $R^5$ have the same meanings as defined above.

Processes 45 to 49

A ribose compound (IVa) of the above general formula (IV) can be derived into compounds represented by the above general formula (IVb) to (IVf), for example, in methods described in the following literatures of Process 45 to Process 49, optionally using a protective group.

Process 45: Chemical & Pharmaceutical Bulletin, 51(4), pp. 399-403, 2003; Chemical & Pharmaceutical Bulletin, 36(3), pp. 945-953, 1988.

Process 46: J. Chem. Soc., Perkin Trans. 1, pp. 298-304, 2001; J. Heterocyclic Chem., 38, p. 1297, 2001.

Process 47: The Journal of Antibiotics, 37, pp. 941-942, 1984; European Journal of Organic Chemistry, pp. 3997-4002, 2003; Journal of Medicinal Chemistry, 46(22), pp. 4776-4789, 2003.

Process 48: Angew. Chem. Int. Ed., 41, No. 20, pp. 3913-3915, 2002; Nucleosides & Nucleotide, 14(9&10), pp. 1831-1852, 1995; Journal of Organic Chemistry, 53, pp. 5046-5050, 1988.

Process 49: Tetrahedron Letters, pp. 7941-7943, 2003; Journal of Organic Chemistry, 66, pp. 7469-7477, 2001; Journal of the American Chemical Society, 123(5), pp. 870-874, 2001.

As protective groups used in the above-mentioned production methods, various protective groups generally used in hexylidene group and the like can be illustrated. As a thiol-protective group, a p-methoxybenzyl group, a benzyl group, an acetyl group, a pivaroyl group, a benzoyl group, a benzyloxycarbonyl group and the like can be illustrated. As an amino-protective groups, a benzyloxycarbonyl group, a tert-butoxycarbonyl group, a benzyl group, a p-methoxybenzyl group, a trifluoroacetyl group, an acetyl group, a phthaloyl group and the like can be illustrated. As a carboxyl-protective group, a benzyl group, a tert-butyldimethylsilyl group, an aryl group and the like can be illustrated.

The compounds represented by the above general formula (I) of the present invention obtained by the above production methods can be isolated and purified by conventional separation means such as fractional recrystallization, purification using chromatography, solvent extraction and solid phase extraction or the like.

The benzimidazole derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like, salts with inorganic bases such as sodium salt, potassium salt and the like, addition salts with organic bases such as N-methyl-D-glucamin, N,N'-dibenzylethylenediamine, 2-aminoethanol, tris(hydroxymethyl)aminomethane, arginine, lysine and the like.

The benzimidazole derivatives represented by the above general formula (I) of the present invention or pharmaceutically acceptable salts thereof include their solvates with pharmaceutically acceptable solvents such as ethanol, water and the like.

Among the benzimidazole derivatives represented by the above general formula (I) of the present invention, there can be two geometric isomers, cis(Z)-isomer and trans(E)-isomer, in each compound having an unsaturated bond. In the present invention, either of cis(Z)-isomer and trans(E)-isomer can be employed.

Among the benzimidazole derivatives represented by the above general formula (I) of the present invention, there can be two optical isomers, R-isomer and S-isomer, in each compound having an asymmetric carbon atom excluding the sugar-residue moiety. In the present invention, either of R-isomer and S-isomer can be employed, and a mixture of both isomers can be also employed.

Among the benzimidazole derivatives represented by the above general formula (I) of the present invention, there can be some tautomers. The compounds of the present invention include their tautomers.

In addition, in the present invention, various prodrugs of the compounds represented by the above general formula (I) can be also used. The term "prodrug" means a compound obtained by modifying a parent compound with a pharmaceutically acceptable group generally used in a prodrug, and such compound can be expected, for example, to have additional characteristics such as improved stability, long action or the like and exert an efficacy after being converted into the parent compound in the intestine tract or the like. The prodrugs of the compound represented by the above general formula (I) of the present invention can be prepared by suitably introducing a group forming a prodrug into one or more group optionally selected a hydroxy group, an amino group, another group acceptable to form a prodrug of a compound represented by the above general formula (I) using an agent to form a prodrug such as a corresponding halide or the like in the usual way and then optionally isolating and purifying in the usual way as an occasion demand (see "Gekkan-yakuji The clinical pharmacokinetics for proper uses of pharmaceutical drugs", Extra edition, March 2000, Vol. 42, No. 4, pp. 669-707; "New drug delivery system", issued by CMC Co. Ltd., Jan. 31, 2000, pp. 67-173). As a group forming a prodrug used in a hydroxy group or an amino group, for example, $C_{1-6}$ alkyl-CO—, $C_{1-6}$ alkyl-O—$C_{1-6}$ alkyl-CO—, $C_{1-6}$ alkyl-OCO—$C_{1-6}$ alkyl-CO—, $C_{1-6}$ alkyl-OCO—, $C_{1-6}$ alkyl-O—$C_{1-6}$ alkyl-OCO— and the like can be illustrated.

In the present invention, as the diseases associated with an abnormality of plasma uric acid level include gout, hyperuricemia, urinary lithiasis, hyperuricemic nephropathy, acute uric acid nephropathy and the like, especially gout and hyperuricemia.

When the pharmaceutical compositions of the present invention are employed in the practical prevention or treatment, the dosage of a compound represented by the above general formula (I) or a pharmaceutically acceptable salt thereof, or a prodrug thereof as the active ingredient is appropriately decided depending on the age, sex, body weight and degree of symptoms and treatment of each patient, for example, which is approximately within the range of 1 to 2,000 mg per day per adult human in the case of oral administration, and the daily dose can be divided into one or several doses and administered suitably.

When the pharmaceutical compositions of the present invention are employed in the practical prevention or treatment, various dosage forms are used depending on their usages for oral or parenteral administration. As examples of the dosage forms, orally administration forms such as powders, fine granules, granules, tablets, capsules, dry syrups or the like are preferable.

These pharmaceutical compositions can be prepared by admixing with an appropriate pharmaceutical additive such as excipients, disintegrators, binders, lubricants or the like in accordance with pharmaceutically conventional methods and formulating the mixture depending on their dosage forms in the usual way.

For example, powders can be formulated by, if desired, admixing well an active ingredient with appropriate excipients, lubricants and the like. Tablets can be formulated by, if desired, admixing an active ingredient with appropriate excipients, disintegrators, binders, lubricants and the like, and compressing the mixture in accordance with conventional methods. The tablets, further if desired, can be suitably coated to provide film-coated tablets, sugar-coated tablets, enteric-coated tablets and the like. Capsules can be formulated by, if desired, admixing well an active ingredient with appropriate excipients, lubricants and the like, or formulating granules or fine-powders in accordance with conventional methods, and then filling the compositions in appropriate capsules. Such orally administration forms can be formulated as immediate release or sustained release preparations depending on the prevention or treatment methods.

The active ingredient of the present invention can be used in combination with a drug for the treatment of hyperuricemia or gout which does not substantially inhibit the absorption of nucleosides. As drugs usable for the treatment of hyperuricemia in the present invention, for example, a uricosuric drug such as probenecid, bucolome, benzbromarone or the like; a uric acid synthesis inhibitor such as allopurinol, oxypurinol, febuxostat, Y-700 or the like; a urinary alkalinizer such as sodium hydrogen carbonate, potassium citrate, sodium citrate or the like; and a uric acid oxidase such as rasburicase, uricase PEG-20, a recombinant uric acid oxidase (uricase) or the like can be illustrated. In addition, as drugs for the treatment of gout, colchicines; a nonsteroidal anti-inflammatory agent such as indometacin, naproxen, fenbufen, pranoprofen, oxaprozin, ketoprofen, etoricoxib, tenoxicam or the like; an adrenocortical steroid such as prednisolone or the like; and the like can be illustrated. In the present invention, the active ingredient of the present invention can be used in combination with at least one of these drugs, and the pharmaceutical composition comprising in combination at least one of these drugs is not limited to a single preparation simultaneously formulated with the active ingredient of the present invention, and includes administration modes such as a combination of a separated preparation formulated separately from a pharmaceutical composition containing the active ingredient of the present invention to be administered at the same or different dosage intervals. In addition, in a case of use in combination with a drug other than the active ingredient of the present invention, the dose of the compound of the present invention can be decreased according to the dosage of the other drug used in combination with, occasionally, beneficial effect more than additive effect in the prevention or treatment of the above diseases can be obtained, and adverse effects of coadministrated drugs can be avoided or declined.

BRIEF DESCRIPTION OF DRAWINGS

The FIG. 1 is a graph showing the pattern of CNT1 and CNT2 distribution in human tissues. The vertical axis is the number of molecular per 1 ng cDNA (molecular numbering cDNA). The horizontal axis is the name of tissues. The left bar graph shows CNT1 and the right bar graph shows CNT2.

The FIG. 2 is a graph showing the pattern of CNT1 to CNT3 distribution in human stomach and intestines. The vertical axis is the number of molecular per 1 ng total RNA (molecular number/ng total RNA). The horizontal axis is the name of part. The left bar graph shows CNT1, the central bar graph shows CNT2 and the right bar graph shows CNT3.

BEST MODE FOR CARRYING OUT THE INVENTION

Figure 1:
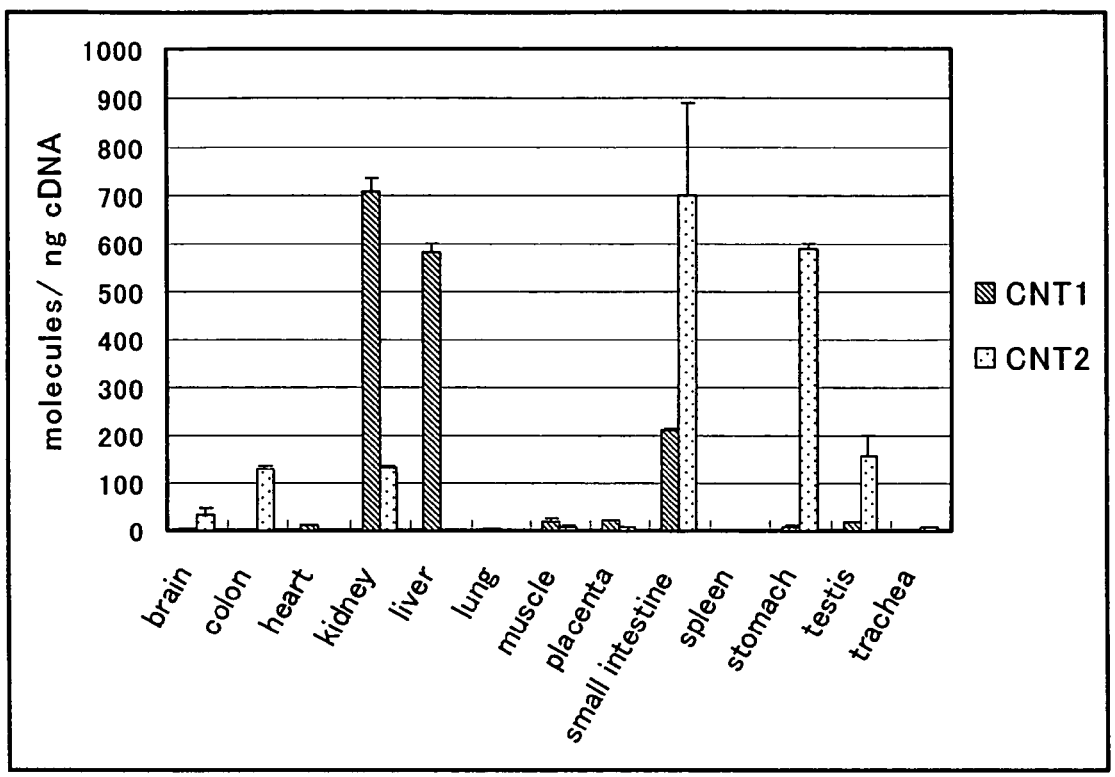

The present invention is further illustrated in more detail by way of the following REFERENCE EXAMPLE s, Examples and Test Examples. However, the present invention is not limited thereto.

REFERENCE EXAMPLE 1

5,6-Dichloro-1,3-dihydro-2H-benzimidazol-2-one 4,5-Dichloro-1,2-phenylenediamine (10 g) was dissolved in tetrahydrofuran (35 mL), and to the mixture was added a suspension of carbonyldiimidazole (9.6 g) in tetrahydrofuran (15 mL) at room temperature. The reaction mixture was stirred at room temperature for 1 hour, and to the reaction mixture was added water under ice-cooling. The insoluble material was collected by filtration and dried to give the title compound (11.6 g).
$^1$H-NMR (DMSO-$d_6$) δ ppm: 7.11 (2H, s), 10.93 (2H, s)

REFERENCE EXAMPLE 2

2,5,6-Trichloro-1H-benzimidazole 5,6-Dichloro-1,3-dihydro-2H-benzimidazol-2-one (11.5 g) was suspended in phosphorus oxychloride (40 mL), and the mixture was stirred at 120° C. for 24 hours. After cooling the reaction mixture, water was added to the reaction mixture, and to the mixture was added 28% aqueous ammonia solution to alkalize. The solid was collected by filtration and dried to give the title compound (5.0 g).
$^1$H-NMR (DMSO-$d_6$) δ ppm: 7.83 (2H, brs), 13.30-14.00 (1H, br)

REFERENCE EXAMPLE 3

2-Chloro-1-(2,3,5-tri-O-acetyl-β-D-ribofuranosyl)-1H-benzimidazole

2-Chlorobenzimidazole (7.5 g) and N,O-bis(trimethylsilyl)acetoamide (18.3 mL) were suspended in acetonitrile (150 mL), and the mixture was stirred at 80° C. for 1 hour. The reaction mixture was allowed to cool to room temperature. To the mixture was added trifluoromethanesulfonic acid trimethylsilyl ester (17.9 mL), and the mixture was stirred for 15 minutes. To the reaction mixture was added 1,2,3,5-tetra-O-acetyl-D-ribofuranose (17.3 g), and the mixture was stirred at room temperature for 6 hour. To the reaction mixture was added a saturated aqueous sodium hydrogen carbonate solution, and the resulting mixture was extracted with ethyl acetate. The organic layer was washed with brine and dried over anhydrous magnesium sulfate, and the solvent was removed under reduced pressure. The obtained residue was purified by column chromatography on silica gel (eluent: ethyl acetate/hexane=1/10) to give the title compound (12.4 g).
$^1$H-NMR (CDCl$_3$) δ ppm: 2.05 (3H, s), 2.17 (3H, s), 2.22 (3H, s), 4.30-4.60 (3H, m), 5.51 (1H, dd, J=4.0 Hz, 6.6 Hz), 5.65 (1H, dd, J=6.6 Hz, 7.3 Hz), 6.24, (1H, J=7.3 Hz), 7.20-7.40 (2H, m), 7.61 (1H, d, J=7.4 Hz), 7.71 (1H, d, J=7.4 Hz)

REFERENCE EXAMPLE 4

The following compound was prepared in a similar manner to that described in Reference Example 3 using the corresponding materials.

1-(2,3,5-Tri-O-acetyl-β-D-ribofuranosyl)-2,5,6-trichloro-1H-benzimidazole $^1$H-NMR (CDCl$_3$) δ ppm: 2.05 (3H, s), 2.19 (3H, s), 2.32 (3H, s), 4.30-4.45 (2H, m), 4.55-4.65 (1H, m), 5.46 (1H, dd, J=2.7 Hz, 6.8 Hz), 5.50 (1H, dd, J=6.8 Hz, 7.5 Hz), 6.18, (1H, J=7.5 Hz), 7.80 (1H, s), 7.81 (1H, s)

REFERENCE EXAMPLE 5

2-Chloro-1-(β-D-ribofuranosyl)-1H-benzimidazole

2-Chloro-1-(2,3,5-tri-O-acetyl-β-D-ribofuranosyl)-1H-benzimidazole (12.3 g) was dissolved in methanol (150 mL). To the mixture was added 28% sodium methoxide-methanol solution (1 mL), and the mixture was stirred for 1 hour. The reaction mixture was concentrated under reduced pressure to give the title compound (8.5 g).
$^1$H-NMR (DMSO-$d_6$) δ ppm: 3.60-3.78 (2H, m), 3.90-4.03 (1H, m), 4.13 (1H, dd, J=2.2 Hz, 5.8 Hz), 4.50 (1H, dd, J=5.8 Hz, 7.5 Hz), 5.89 (1H, d, J=7.5 Hz), 7.15-7.35 (2H, m), 7.62 (1H, d, J=7.5 Hz), 7.99 (1H, d, 7.5 Hz)

REFERENCE EXAMPLE 6

The following compound was prepared in a similar manner to that described in Reference Example 5 using the corresponding materials.

1-(β-D-Ribofuranosyl)-2,5,6-trichloro-1H-benzimidazole $^1$H-NMR (DMSO-$d_6$) δ ppm: 3.60-3.80 (2H, m), 3.95-4.25 (2H, m), 4.35-4.50 (1H, m), 5.20-5.60 (3H, m), 5.89 (1H, d, J=7.9 Hz), 7.97 (1H, s), 8.56 (1H, s)

REFERENCE EXAMPLE 7

2-Azido-1-(2,3,5-tri-O-acetyl-β-D-ribofuranosyl-1H-benzimidazole

2-Chloro-1-(2,3,5-tri-O-acetyl-β-D-ribofuranosyl)-1H-benzimidazole (1.0 g) was dissolved in N,N-dimethylformamide (10 mL). To the mixture was added sodium azide (1.1 g), and the mixture was stirred at 100° C. for 24 hours. To the reaction mixture was added water, and the resulting mixture was extracted with ethyl acetate. The organic layer was washed with brine and dried over anhydrous magnesium sulfate, and the solvent was removed under reduced pressure. The obtained residue was purified by column chromatography on silica gel (eluent: ethyl acetate/hexane=1/2) to give the title compound (0.45 g).

$^1$H-NMR (CDCl$_3$) δ ppm: 2.06 (3H, s), 2.16 (3H, s), 2.19 (3H, s), 4.30-4.50 (3H, m), 5.51 (1H, dd, J=4.1 Hz, 6.5 Hz), 5.70 (1H, dd, J=6.5 Hz, 6.7 Hz), 5.59 (1H, d, J=6.7 Hz), 7.15-7.35 (2H, m), 7.47 (1H, d, J=8.0 Hz), 7.63 (1H, d, J=8.0 Hz)

REFERENCE EXAMPLE 8

2-Amino-1-(2,3,5-tri-O-acetyl-β-D-ribofuranosyl)-1H-benzimidazole

2-Azido-1-(2,3,5-tri-O-acetyl-β-D-ribofuranosyl)-1H-benzimidazole (100 mg) was dissolved in methanol (2 mL). To the solution was added a catalytic amount of 10% palladium-carbon powder, and the mixture was stirred at room temperature under a hydrogen atmosphere for 1 hour. The insoluble material was removed by filtration, and the solvent of filtrate was removed under reduced pressure to give the title compound (97 mg).

$^1$H-NMR (CDCl$_3$) δ ppm: 1.99 (3H, s), 2.16 (3H, s), 2.17 (3H, s), 4.27-4.43 (2H, m), 4.55-4.68 (1H, m), 5.07 (2H, brs), 5.43 (H, dd, J=3.7 Hz, 6.6 Hz), 5.57 (1H, dd, J=6.6 Hz, 7.5 Hz), 6.04 (1H, d, J=7.5 Hz), 7.08 (1H, t, J=7.8 Hz), 7.15 (1H, t, J=7.8 Hz), 7.21 (1H, d, J=7.8 Hz), 7.42 (1H, d, J=7.8 Hz)

REFERENCE EXAMPLE 9

4-Benzyloxy-3-hydroxybenzaldehyde 3,4-Dihydroxybenzaldehyde (21.6 g) and potassium carbonate (21.56 g) were suspended in N,N-dimethylformamide (200 mL). To the mixture was added dropwise benzylbromide (18.5 mL) under ice-cooling, and the mixture was stirred at room temperature for 16 hours. To the reaction mixture was added dropwise 2 mol/L hydrochloric acid (400 mL), and the resulting mixture was extracted with ethyl acetate. The organic layer was washed with brine and dried over anhydrous magnesium sulfate. The solvent was removed under reduced pressure, and the obtained residue was purified by column chromatography on silica gel (eluent: ethyl acetate/hexane=1/5) to give the title compound (19.0 g).

$^1$H-NMR (CDCl$_3$) δ ppm: 5.20 (2H, s), 7.04 (1H, d, J=8.2 Hz), 7.20-7.60 (7H, m), 9.84 (1H, s)

REFERENCE EXAMPLE 10

The following compound was prepared in a similar manner to that described in Reference Example 9 using the corresponding materials.

3-Benzyloxybenzonitrile $^1$H-NMR (CDCl$_3$) δ ppm: 5.08 (2H, s), 7.13-7.50 (9H, m)

REFERENCE EXAMPLE 11

3-Methoxy-4-phenylbenzonitrile

4-Hydroxy-3-methoxybenzonitrile (14.9 g) and pyridine (24 mL) were dissolved in dichloromethane (150 mL). To the stirred mixture was added dropwise trifluoromethanesulfonic anhydride (19.4 mL) under ice-cooling. The mixture was stirred at room temperature for 30 minutes. To the reaction mixture was added dilute hydrochloric acid, and the resulting mixture was extracted with ethyl acetate. The organic layer was washed with brine and dried over anhydrous magnesium sulfate. The solvent was removed under reduced pressure to give the trifluoromethanesulfonic acid ester. The obtained trifluoromethanesulfonic acid ester, phenylboronic acid (14.7 g), tetrabutylammonium bromide (1.6 g), sodium carbonate (21.2 g), tetrakis(triphenylphosphine)palladium (5.7 g) and water (24 mL) were suspended in toluene (150 mL), and the mixture was stirred at 80° C. for 12 hours. The insoluble material was removed by filtration through celite, and the solvent of filtrate was removed under reduced pressure. To the residue was added dropwise water, and then added brine, and the resulting mixture was extracted with ethyl acetate. The organic layer was washed with brine and dried over anhydrous magnesium sulfate. The solvent was removed under reduced pressure, and the obtained residue was purified by column chromatography on silica gel (eluent: ethyl acetate/hexane=1/5) to give the title compound (18.0 g).

$^1$H-NMR (CDCl$_3$) δ ppm: 3.84 (3H, s), 7.15-7.60 (8H, m)

REFERENCE EXAMPLE 12

The following compound was prepared in a similar manner to that described in Reference Example 11 using the corresponding materials.

2-Methoxy-4-phenylbenzaldehyde $^1$H-NMR (CDCl$_3$) δ ppm: 4.01 (3H, s), 7.17 (1H, d, J=1.9 Hz), 7.20-7.70 (6H, m), 7.90 (1H, d, J=8.3 Hz), 10.49 (1H, s)

REFERENCE EXAMPLE 13

4-Benzyloxy-3-hydroxybenzonitrile

4-Benzyloxy-3-hydroxybenzaldehyde (19.0 g), hydroxylamine hydrochloride (8.6 g), sodium acetate (13.7 g) and water (30 mL) were suspended in ethanol (150 mL), and the mixture was stirred at 80° C. for 8 hours. To the reaction mixture was added water (100 mL), and the resulting mixture was extracted with ethyl acetate. The organic layer was washed with brine and dried over anhydrous magnesium sulfate. The solvent was removed under reduced pressure to give the oxime compound. The obtained oxime compound was dissolved in dichloromethane (100 mL), and to the reaction mixture was added pyridine (20 mL). To the stirred mixture was added dropwise trifluoroacetic anhydride (35.3 mL) under ice-cooling. The mixture was stirred at room temperature for 6 hours. To the stirred mixture was added 2 mol/L hydrochloric acid (100 mL), and the resulting mixture was extracted with ethyl acetate. The organic layer was washed with a saturated aqueous sodium hydrogen carbonate solution and brine successively and dried over anhydrous magnesium sulfate. The solvent was removed under reduced pressure, and the obtained residue was purified by column chromatography on silica gel (eluent: ethyl acetate/hexane=1/10 to give the title compound (11.0 g).

$^1$H-NMR (CDCl$_3$) δ ppm: 5.17 (2H, s), 5.82 (1H, s), 6.96 (1H, d, J=8.3 Hz), 7.13-7.25 (2H, m), 7.35-7.50 (5H, m)

REFERENCE EXAMPLE 14

3-Hydroxy-4-phenylbenzonitrile

3-Methoxy-4-phenylbenzonitrile (17.8 g) was dissolved in dichloromethane (200 mL). To the stirred mixture was added dropwise boron tribromide (14 mL) under ice-cooling, and the mixture was stirred at continuous temperature for 6 hours. To the stirred reaction mixture was added dropwise water (200 mL) under ice-cooling, and the resulting mixture was extracted with ethyl acetate. The organic layer was washed with brine and dried over anhydrous magnesium sulfate. The solvent was removed under reduced pressure, and the obtained residue was purified by column chromatography on silica gel (eluent: ethyl acetate/hexane=1/5) to give the title compound (11.0 g).

$^1$H-NMR (CDCl$_3$) δ ppm: 5.55 (1H, brs), 7.20-7.60 (8H, m)

REFERENCE EXAMPLE 15

The following compound was prepared in a similar manner to that described in Reference Example 14 using the corresponding materials.

2-Hydroxy-4-phenylbenzaldehyde $^1$H-NMR (CDCl$_3$) δ ppm: 7.15-7.32 (2H, m), 7.35-7.53 (3H, m), 7.57-7.70 (3H, m), 9.93 (1H, s), 11.12 (1H, s)

REFERENCE EXAMPLE 16

2-Hydroxy-4-phenylbenzaldehyde oxime

2-Hydroxy-4-phenylbenzaldehyde (3.7 g), hydroxylamine hydrochloride (1.4 g), sodium acetate (3.1 g) and water (10 mL) were suspended in ethanol (50 mL), and the mixture was stirred at 80° C. for 3 hours. To the reaction mixture was added water (50 mL), and the resulting mixture was extracted with ethyl acetate. The organic layer was washed with brine and dried over anhydrous magnesium sulfate, and the solvent was removed under reduced pressure to give the title compound (3.0 g).

$^1$H-NMR (CDCl$_3$) δ ppm: 7.17 (1H, dd, J=2.0 Hz, 7.9 Hz), 7.20-7.30 (2H, m), 7.34-7.50 (3H, m), 7.55-7.65 (2H, m), 8.26 (1H, s), 9.87 (1H, brs)

REFERENCE EXAMPLE 17

The following compound was prepared in a similar manner to that described in Reference Example 16 using the corresponding materials.

2-Methoxy-4-phenylbenzaldehyde oxime $^1$H-NMR (CDCl$_3$) δ ppm: 3.93 (3H, s), 7.11 (1H, d, J=1.6 Hz), 7.20 (1H, dd, J=1.6 Hz, 7.9 Hz), 7.33-7.50 (3H, m), 7.55-7.65 (2H, m), 7.78 (1H, d, J=7.9 Hz), 8.53 (1H, s)

REFERENCE EXAMPLE 18

4-Benzyloxy-3-(4-benzyloxybutoxy)benzonitrile

4-Benzyloxy-3-hydroxybenzonitrile (3.4 g) and potassium carbonate (6.3 g) were dissolved in N,N-dimethylformamide (20 mL). To the mixture was added benzyl 4-bromobutylether (3 mL), and the mixture was stirred at 50° C. for 16 hours. To the reaction mixture was added dropwise 2 mol/L hydrochloric acid (4 mL), and the resulting mixture was extracted with ethyl acetate. The organic layer was washed with brine and dried over anhydrous magnesium sulfate. The solvent was removed under reduced pressure, and the obtained residue was purified by column chromatography on silica gel (eluent: ethyl acetate/hexane=1/5) to give the title compound (5.9 g)

$^1$H-NMR (CDCl$_3$) δ ppm: 1.70-2.10 (4H, m), 3.55 (2H, t, J=6.1 Hz), 4.04 (2H, t, J=6.5 Hz), 4.49 (2H, s), 5.17 (2H, s), 6.90 (1H, d, J=8.2 Hz), 7.08 (1H, d, J=1.9 Hz), 7.19 (1H, dd, J=1.9 Hz, 8.2 Hz), 7.24-7.45 (10H, m)

REFERENCE EXAMPLE 19

The following compound was prepared in a similar manner to that described in Reference Example 18 using the corresponding materials.

3-(3-Benzyloxypropoxy)benzonitrile $^1$H-NMR (CDCl$_3$) δ ppm: 1.95-2.25 (2H, m), 3.65 (2H, t, J=6.0 Hz), 4.10 (2H, t, J=6.0 Hz), 4.52 (2H, s), 7.00-7.50 (9H, m)

REFERENCE EXAMPLE 20

4-Hydroxy-3-(4-hydroxybutoxy)benzonitrile

4-Benzyloxy-3-(4-benzyloxybutoxy)benzonitrile (4.0 g) was dissolved in a mixed solvent of trifluoroacetic acid (9 mL), dimethylsulfide (0.5 mL) and water (5 mL), and the mixture was stirred at room temperature for 18 hours. The solvent was removed under reduced pressure, and the obtained residue was purified by column chromatography on silica gel (eluent: ethyl acetate/hexane=1/5) to give the title compound (1.0 g).

$^1$H-NMR (CDCl$_3$) δ ppm: 1.90-2.05 (4H, m), 4.05-4.20 (2H, m), 4.40-4.55 (2H, m), 6.06 (1H, s), 6.98 (1H, d, J=8.3 Hz), 7.07 (1H, d, J=1.8 Hz), 7.24 (1H, dd, J=1.8 Hz, 8.3 Hz)

REFERENCE EXAMPLE 21

4-(3-Benzyloxyphenyl)-3-(4-hydroxybutoxy)benzonitrile

4-Hydroxy-3-(4-hydroxybutoxy)benzonitrile (1.0 g) and pyridine (1.9 mL) were dissolved in dichloromethane (15 mL), and to the mixture was added dropwise trifluoromethanesulfonic anhydride (1.7 mL) under ice-cooling. The mixture was stirred at room temperature for 30 minutes, and to the reaction mixture was added 1 mol/L hydrochloric acid (50 mL). The resulting mixture was extracted with ethyl acetate, and the organic layer was washed with a saturated aqueous sodium hydrogen carbonate solution and brine successively and dried over anhydrous magnesium sulfate. The solvent was removed under reduced pressure to give trifluoromethanesulfonic acid ester. The obtained trifluoromethanesulfonic acid ester, 3-benzyloxyphenylboronic acid (1.3 g), sodium carbonate (1.0 g), tetrakis(triphenylphosphine)palladium (0.3 g) and water (2 mL) were suspended in N,N-dimethylformamide (15 mL), and the mixture was stirred at 80° C. for 12 hours. To the reaction mixture was added dropwise 1 mol/L hydrochloric acid (30 mL), and the resulting mixture was extracted with ethyl acetate. The organic layer was washed with brine and dried over anhydrous magnesium sulfate. The solvent was removed under reduced pressure, and the obtained residue was purified by column chromatography on aminopropylated silica gel (eluent: ethyl acetate/hexane=1/5) to give the title compound (0.8 g).

$^1$H-NMR (CDCl$_3$) δ ppm: 1.60-1.72 (2H, m), 1.78-1.90 (2H, m), 3.62 (2H, t, J=6.5 Hz), 4.02 (2H, t, J=6.2 Hz), 5.10 (2H, s), 6.90-7.50 (12H, m)

REFERENCE EXAMPLE 22

4-Benzyloxy-3-(4-benzyloxybutoxy)benzylamine

Lithium aluminium hydride (2.6 g) was suspended in tetrahydrofuran (30 mL), and to the mixture was added dropwise a solution of 4-benzyloxy-3-(4-benzyloxybutoxy)benzonitrile (5.9 g) in tetrahydrofuran (30 mL) under ice-cooling. The mixture was stirred at 60° C. for 2 hours. After the mixture was cooled in an ice bath, ethanol and water were successively added dropwise to the reaction mixture. To the reaction mixture was added anhydrous sodium sulfate, and the insoluble material was removed by filtration through celite. The filtrate was concentrated under reduced pressure, and the obtained residue was purified by column chromatography on aminopropylated silica gel (eluent: ethyl acetate/hexane=1/5) to give the title compound (2.5 g).

$^1$H-NMR (CDCl$_3$) δ ppm: 1.70-2.00 (4H, m), 3.55 (2H, t, J=6.4 Hz), 3.78 (2H, s), 4.06 (2H, t, J=6.5 Hz), 4.49 (2H, s), 5.10 (2H, s), 6.70-7.00 (3H, m), 7.20-7.50 (10H, m)

REFERENCE EXAMPLE 23

The following compounds were prepared in a similar manner to that described in Reference Example 20 using the corresponding nitrile compound or oxime compound.

3-Methoxy-4-phenylbenzylamine $^1$H-NMR (CDCl$_3$) δ ppm: 3.83 (3H, s), 3.92 (2H, s), 6.80-7.70 (8H, m)

2-Methoxy-4-phenylbenzylamine $^1$H-NMR (CDCl$_3$) δ ppm: 3.87 (2H, s), 3.92 (3H, s), 7.00-7.70 (8H, m)

3-(3-Benzyloxypropoxy)benzylamine $^1$H-NMR (CDCl$_3$) δ ppm: 1.95-2.15 (2H, m), 3.65 (2H, t, J=6.1 Hz), 3.83 (2H, s), 4.07 (2H, t, J=6.1 Hz), 4.51 (2H, s), 6.70-7.50 (9H, m)

3-Hydroxy-4-phenylbenzylamine $^1$H-NMR (DMSO-d$_6$) δ ppm: 3.67 (2H, s), 6.83 (1H, d, J=7.8 Hz), 6.91 (1H, s), 7.16 (1H, d, J=7.8 Hz), 7.26 (1H, t, J=7.7 Hz), 7.37 (2H, t, J=7.7 Hz), 7.52 (2H, d, J=7.7 Hz)

2-Hydroxy-4-phenylbenzylamine $^1$H-NMR (CDCl$_3$) δ ppm: 4.17 (2H, s), 6.95-7.70 (8H, m)

3-Benzyloxybenzylamine $^1$H-NMR (CDCl$_3$) δ ppm: 3.85 (2H, s), 5.08 (2H, s), 6.86 (1H, d, J=8.2 Hz), 6.91 (1H, d, J=7.7 Hz), 6.96 (1H, s), 7.20-7.50 (6H, m)

4-(3-Benzyloxyphenyl)-3-(4-hydroxybutoxy)benzylamine $^1$H-NMR (CDCl$_3$) δ ppm: 1.60-1.72 (2H, m), 1.75-1.90 (2H, m), 3.60 (2H, t, J=6.4 Hz), 3.89 (2H, s), 4.02 (2H, t, J=6.2 Hz), 5.09 (2H, s), 6.85-7.55 (12H, m)

REFERENCE EXAMPLE 24

3-(4-Acetoxybutoxy)-5-hydroxybenzaldehyde 3,5-Dihydroxybenzaldehyde (0.96 g) and potassium carbonate (1.44 g) were suspended in N,N-dimethylformamide (5 mL). To the mixture was added 4-bromobutyl acetate (1.49 g) under ice-cooling, and the mixture was stirred at room temperature for 16 hours. To the reaction mixture was added 1 mol/L hydrochloric acid, and the resulting mixture was extracted with diethyl ether. The organic layer was washed with a saturated aqueous sodium hydrogen carbonate solution and brine successively and dried over anhydrous magnesium sulfate. The filtrate was concentrated under reduced pressure, and the obtained residue was purified by column chromatography on silica gel (ethyl acetate/hexane=1/5) to give the title compound (0.57 g).

$^1$H-NMR (CDCl$_3$) δ ppm: 1.75-1.95 (4H, m), 2.07 (3H, s), 3.95-4.25 (4H, m), 5.65 (1H, s), 6.67 (1H, s), 6.90-7.05 (2H, m), 9.88 (1H, s)

REFERENCE EXAMPLE 25

3-(4-Benzyloxybutoxy)-4-hydroxybenzaldehyde 3,4-Dihydroxybenzaldehyde (0.1 g) and sodium hydride (60%, 0.064 g) were suspended in N,N-dimethylformamide (2 mL), and to the reaction mixture was added benzyl 4-bromobutylether (0.185 g) under ice-cooling. The mixture was stirred at room temperature for 17 hours. To the reaction mixture was added water, and the resulting mixture was extracted with ethyl acetate. The organic layer was washed with brine and dried over anhydrous magnesium sulfate. The filtrate was concentrated under reduced pressure, and the obtained residue was purified by column chromatography on silica gel (ethyl acetate/hexane=1/3) to give the title compound (0.1 g).

$^1$H-NMR (CDCl$_3$) δ ppm: 1.70-1.85 (2H, m), 1.90-2.05 (2H, m), 3.56 (2H, t, J=6.1 Hz), 4.15 (2H, t, J=6.3 Hz), 4.53 (2H, s), 6.42 (1H, s), 7.03 (1H, d, J=8.3 Hz), 7.20-7.50 (7H, m), 9.81 (1H, s)

REFERENCE EXAMPLE 26

3-(4-Acetoxybutoxy)-5-phenylbenzaldehyde 3-(4-Acetoxybutoxy)-5-hydroxybenzaldehyde (0.35 g) and pyridine (0.50 mL) were dissolved in dichloromethane (5 mL), and to the mixture was added dropwise trifluoromethanesulfonic anhydride (0.27 mL) under ice-cooling. The mixture was stirred at room temperature for 30 minutes. To the reaction mixture was added 1 mol/L hydrochloric acid, and the resulting mixture was extracted with ethyl acetate. The organic layer was washed with brine and dried over anhydrous magnesium sulfate, and the solvent was removed under reduced pressure to give the trifluoromethanesulfonic acid ester. The obtained trifluoromethanesulfonic acid ester, phenylboronic acid (0.20 g), potassium carbonate (0.29 g), tetrakis(triphenylphosphine) palladium (0.08 g) and water (1 mL) were suspended in N,N-dimethylformamide (5 mL), and the mixture was stirred at 80° C. for 12 hours. The insoluble material was removed by filtration through celite, and the filtrate was concentrated under reduced pressure. To the residue was added dropwise water, and then added brine, and the resulting mixture was extracted with ethyl acetate. The organic layer was washed with brine and dried over anhydrous magnesium sulfate. The filtrate was concentrated under reduced pressure, and the obtained residue was purified by column chromatography on silica gel (eluent: ethyl acetate/hexane=1/5) to give the title compound (0.22 g).
$^1$H-NMR (CDCl$_3$) δ ppm: 1.80-2.00 (4H, m), 2.06 (3H, s), 4.05-4.25 (4H, m), 7.30-7.52 (5H, m), 7.56-7.75 (3H, m), 10.04 (1H, s)

REFERENCE EXAMPLE 27

The following compound was prepared in a similar manner to that described in Reference Example 26 using the corresponding materials.

3-(4-Benzyloxybutoxy)-4-(3-methoxycarbonylphenyl)benzaldehyde $^1$H-NMR (CDCl$_3$) δ ppm: 1.60-1.95 (4H, m), 3.47 (2H, t, J=6.2 Hz), 3.91 (3H, s), 4.09 (2H, t, J=6.2 Hz), 4.45 (2H, s), 6.95-7.70 (9H, m), 7.76 (1H, d, J=7.6 Hz), 8.04 (1H, d, J=7.6 Hz), 8.25 (1H, s), 10.00 (1H, s)

3-Methoxy-4-phenylbenzaldehyde $^1$H-NMR (CDCl$_3$) δ ppm: 3.89 (3H, s), 7.30-7.65 (8H, m), 10.01 (1H, s)

3-(4-Benzyloxybutoxy)-4-(3-methanesulfonylphenyl)benzaldehyde $^1$H-NMR (CDCl$_3$) δ ppm: 1.60-1.95 (4H, m), 3.04 (3H, s), 3.49 (2H, t, J=6.1 Hz), 4.10 (2H, t, J=6.3 Hz), 4.46 (2H, s), 7.20-7.70 (9H, m), 7.83 (1H, d, J=8.0 Hz), 7.93 (1H, d, J=8.0 Hz), 8.19 (1H, s), 10.01 (1H, s)

4-(3-Hydroxyphenyl)benzaldehyde $^1$H-NMR (CDCl$_3$) δ ppm: 6.60-8.00 (8H, m), 10.06 (1H, s)

REFERENCE EXAMPLE 28

3-Hydroxy-4-phenylbenzaldehyde

3-Methoxy-4-phenylbenzaldehyde (23.0 g) was dissolved in dichloromethane (150 mL). To the stirred mixture was added dropwise boron tribromide (15.4 mL) under ice-cooling, and the mixture was stirred at room temperature for 2 hours. To the stirred reaction mixture was added dropwise water (20 mL) under ice-cooling, and the resulting mixture was extracted with ethyl acetate. The organic layer was washed with brine and dried over anhydrous magnesium sulfate. The solvent was removed under reduced pressure. The obtained residue was suspended in methanol (100 mL) and 2 mol/L hydrochloric acid (50 mL), and the mixture was stirred at 50° C. for 2 hours. To the reaction mixture was added brine, and the resulting mixture was extracted with ethyl acetate. The organic layer was washed with brine and dried over anhydrous magnesium sulfate. The solvent was removed under reduced pressure, and the obtained residue was purified by column chromatography on silica gel (eluent: ethyl acetate/hexane=1/5) to give the title compound (13.8 g).
$^1$H-NMR (CDCl$_3$) δ ppm: 5.43 (1H, s), 7.30-7.65 (8H, m), 9.99 (1H, s)

REFERENCE EXAMPLE 29

4-Fluoro-3-methoxymethoxybenzaldehyde

4-Fluoro-3-hydroxybenzaldehyde (11.9 g) and N,N-diisopropylethylamine (44 mL) were dissolved in dichloromethane (100 mL). To the mixture was added chloromethylmethylether (13 mL), and the mixture was stirred at room temperature for 3 hours. To the reaction mixture was added dropwise 1 mol/L hydrochloric acid (250 mL), and the resulting mixture was extracted with ethyl acetate. The organic layer was washed with brine and dried over anhydrous magnesium sulfate. The solvent was removed under reduced pressure to give the title compound (14.5 g).
$^1$H-NMR (CDCl$_3$) δ ppm: 3.54 (3H, s), 5.29 (2H, s), 7.20-7.30 (1H, m), 7.50-7.60 (1H, m), 7.70-7.80 (1H, m), 9.92 (1H, s)

REFERENCE EXAMPLE 30

3-Methoxymethoxy-4-(morpholin-4-yl)benzaldehyde

4-Fluoro-3-methoxymethoxybenzaldehyde (1.12 g), morpholine (0.8 mL), potassium carbonate (1.26 g) and water (3 mL) were suspended in dimethylsulfoxide (10 mL), and the mixture was stirred at 100° C. for 18 hours. To the reaction mixture was added a saturated aqueous sodium hydrogen carbonate solution, and the resulting mixture was extracted with ethyl acetate. The organic layer was washed with brine and dried over anhydrous magnesium sulfate. The solvent was removed under reduced pressure, and the obtained residue was purified by column chromatography on silica gel (eluent: ethyl acetate/hexane=1/5) to give the title compound (0.8 g).
$^1$H-NMR (CDCl$_3$) δ ppm: 3.15-3.30 (4H, m), 3.53 (3H, s), 3.80-3.95 (4H, m), 5.27 (2H, s), 6.98 (1H, d, J=8.2 Hz), 7.51 (1H, dd, J=2.0 Hz, 8.2 Hz), 7.59 (1H, d, J=2.0 Hz), 9.85 (1H, s)

REFERENCE EXAMPLE 31

3-Hydroxy-4-(morpholin-4-yl)benzaldehyde

3-Methoxymethoxy-4-(morpholin-4-yl)benzaldehyde (0.35 g) was dissolved in methanol (10 mL). To the mixture was added 2 mol/L hydrochloric acid (5 mL), and the mixture was stirred at 60° C. for 18 hours. To the reaction mixture was added a saturated aqueous sodium hydrogen carbonate solution, and the resulting mixture was extracted with ethyl acetate. The organic layer was washed with brine and dried over anhydrous magnesium sulfate. The solvent was removed under reduced pressure to give the title compound (0.29 g).
$^1$H-NMR (CDCl$_3$) δ ppm: 2.90-3.02 (4H, m), 3.80-3.95 (4H, m), 6.55-6.75 (1H, m), 7.20-7.30 (1H, m), 7.40-7.50 (2H, m), 9.91 (1H, s)

REFERENCE EXAMPLE 32

3-(4-Benzyloxybutoxy)-4-(morpholin-4-yl)benzaldehyde

3-Hydroxy-4-(morpholin-4-yl)benzaldehyde (0.28 g) and potassium carbonate (0.38 g) were suspended in N,N-dimethylformamide (2 mL). To the reaction mixture was added benzyl 4-bromobutylether (0.36 g), and the mixture was stirred at 50° C. for 16 hours. To the reaction mixture was added water, and the resulting mixture was extracted with ethyl acetate. The organic layer was washed with brine and dried over anhydrous magnesium sulfate. The filtrate was concentrated under reduced pressure, and the obtained residue was purified by column chromatography on silica gel (ethyl acetate/hexane=1/5) to give the title compound (0.50 g).

$^1$H-NMR (CDCl$_3$) δ ppm: 1.70-1.85 (2H, m), 1.90-2.05 (2H, m), 3.15-3.30 (4H, m), 3.55 (2H, t, J=6.3 Hz), 3.80-3.95 (4H, m), 4.09 (2H, t, J=6.5 Hz), 4.09 (2H, t, J=6.5 Hz), 4.53 (2H, s), 6.94 (1H, d, J=8.3 Hz), 7.20-7.50 (7H, m), 9.84 (1H, s)

REFERENCE EXAMPLE 33

3-(N-t-Butoxycarbonylpiperidin-4-yloxy)benzaldehyde

3-Hydroxybenzaldehyde (0.98 g), 1-t-butoxycarbonyl-4-hydroxypiperidine (2.41 g) and triphenylphosphine (3.15 g) were suspended in tetrahydrofuran (10 mL). To the mixture was added dropwise 40% azodicarboxylic acid diisopropyl ester-toluene solution (6.1 mL) under ice-cooling, and the mixture was stirred at room temperature for 1 hour. The solvent was removed under reduced pressure, and the obtained residue was purified by column chromatography on silica gel (eluent: ethyl acetate/hexane=1/3) to give the title compound (0.74 g).
$^1$H-NMR (CDCl$_3$) δ ppm: 1.47 (9H, s), 1.70-1.82 (2H, m), 1.88-2.00 (2H, m), 3.30-3.40 (2H, m), 3.65-3.80 (2H, m), 4.50-4.60 (1H, m), 7.13-7.23 (1H, m), 7.35-7.50 (3H, m), 9.97 (1H, s)

REFERENCE EXAMPLE 34

4-Ethoxy-3-hydroxybenzaldehyde 3,4-Dihydroxybenzaldehyde (101.6 g) and potassium carbonate (101.7 g) were suspended in N,N-dimethylformamide (500 mL). To the mixture was added dropwise ethyl iodide (58.8 mL) under ice-cooling, and the mixture was stirred at room temperature for 16 hours. To the reaction mixture was added dropwise 2 mol/L hydrochloric acid (500 mL), and the resulting mixture was extracted with ethyl acetate. The organic layer was washed with brine and dried over anhydrous magnesium sulfate. The solvent was removed under reduced pressure, and the obtained residue was purified by column chromatography on silica gel (eluent: ethyl acetate/hexane=1/1) to give the title compound (74.3 g).
$^1$H-NMR (CDCl$_3$) δ ppm: 1.50 (3H, t, J=7.0 Hz), 4.22 (2H, q, J=7.0 Hz), 5.76 (1H, s), 6.95 (1H, d, J=8.1 Hz), 7.35-7.50 (2H, m), 9.84 (1H, s)

REFERENCE EXAMPLE 35

The following compound was prepared in a similar manner to that described in Reference Example 34 using the corresponding materials.

3-Hydroxy-4-propoxybenzaldehyde

REFERENCE EXAMPLE 36

3-(3-Chloropropoxy)-4-ethoxybenzaldehyde

4-Ethoxy-3-hydroxybenzaldehyde (74.3 g) and potassium carbonate (111.3 g) were suspended in N,N-dimethylformamide (350 mL). To the mixture was added dropwise 1-bromo-3-chloropropane (79.6 mL) under ice-cooling, and the mixture was stirred at room temperature for 16 hours. To the reaction mixture was added dropwise 2 mol/L hydrochloric acid (300 mL), and the resulting mixture was extracted with ethyl acetate. The organic layer was washed with brine and dried over anhydrous magnesium sulfate. The solvent was removed under reduced pressure, and the obtained residue was purified by column chromatography on silica gel (eluent: ethyl acetate/hexane=1/5) to give the title compound (69.8 g).
$^1$H-NMR (CDCl$_3$) δ ppm: 1.49 (3H, t, J=7.0 Hz), 2.20-2.40 (2H, m), 3.78 (2H, t, J=6.3 Hz) 4.17 (2H, t, J=7.0 Hz), 4.22 (2H, t, J=5.8 Hz), 6.96 (1H, d, J=8.1 Hz), 7.38-7.52 (2H, m), 9.84 (1H, s)

REFERENCE EXAMPLE 37

The following compounds were prepared in a similar manner to that described in Reference Example 36 using the corresponding materials.

3-(3-Chloropropoxy)-4-phenylbenzaldehyde $^1$H-NMR (CDCl$_3$) δ ppm: 2.10-2.25 (2H, m), 3.50-3.70 (2H, m), 4.10-4.30 (2H, m), 7.30-7.70 (8H, m), 10.01 (1H, s)

4-Benzyloxy-3-(3-chloropropoxy)benzaldehyde $^1$H-NMR (CDCl$_3$) δ ppm: 2.15-2.40 (2H, m), 3.65-3.85 (2H, m), 4.15-4.35 (2H, m), 5.21 (2H, s), 6.95-7.55 (8H, m), 9.84 (1H, s)

3-(3-Chloropropoxy)-4-methoxybenzaldehyde 3-(3-Chloropropoxy)benzaldehyde 3-(3-Chloropropoxy)-4-propoxybenzaldehyde 4-(3-Chloropropoxyphenyl)benzaldehyde

REFERENCE EXAMPLE 38

3,5-Bis(4-acetoxybutoxy)benzaldehyde 3,5-Dihydroxybenzaldehyde (0.49 g) and potassium carbonate (1.48 g) were suspended in N,N-dimethylformamide (5 mL). To the mixture was added 4-bromobutyl acetate (1.46 g) under ice-cooling, and the mixture was stirred at 50° C. for 16 hours. To the reaction mixture was added 1 mol/L hydrochloric acid, and the resulting mixture was extracted with diethyl ether. The organic layer was washed with a saturated aqueous sodium hydrogen carbonate solution and brine successively and dried over anhydrous magnesium sulfate. The filtrate was concentrated under reduced pressure, and the obtained residue was purified by column chromatography on silica gel (ethyl acetate/hexane=1/5) to give the title compound (0.30 g).
$^1$H-NMR (CDCl$_3$) δ ppm: 1.75-1.95 (8H, m), 2.05 (6H, s), 3.95-4.25 (8H, m), 6.69 (1H, s), 6.99 (2H, s), 9.89 (1H, s)

REFERENCE EXAMPLE 39

3-(4-Benzyloxybutylamino)benzonitrile

3-Aminobenzonitrile (0.45 g) and potassium carbonate (1.05 g) were suspended in N,N-dimethylformamide (5 mL). To the reaction mixture was added benzyl-4-bromobutyl ether (0.63 g), and the mixture was stirred at 50° C. for 16 hours. To the reaction mixture was added 1 mol/L hydrochloric acid, and the resulting mixture was extracted with diethyl ether. The organic layer was washed with a saturated aqueous sodium hydrogen carbonate solution and brine successively and dried over anhydrous magnesium sulfate. The filtrate was concentrated under reduced pressure, and the obtained residue was purified by column chromatography on silica gel (ethylacetate/hexane=1/1) to give the title compound (0.45 g).

$^1$H-NMR (CDCl$_3$) δ ppm: 1.65-1.85 (4H, m), 3.05-3.20 (2H, m), 3.45-3.60 (2H, m), 4.00-4.10 (1H, m), 4.52 (2H, s), 6.65-6.75 (2H, m), 6.91 (1H, d, J=7.6 Hz), 7.17 (1H, t, J=7.6 Hz), 7.23-7.45 (5H, m)

REFERENCE EXAMPLE 40

3-[N-(4-Benzyloxybutyl)-N-methylamino]benzonitrile 3-(4-Benzyloxybutylamino)benzonitrile (0.22 g) and potassium carbonate (0.21 g) were suspended in N,N-dimethylformamide (5 mL). To the reaction mixture was added methyl iodide (0.16 g), and the mixture was stirred at 50° C. for 16 hours. To the reaction mixture was added 1 mol/L hydrochloric acid, and the resulting mixture was extracted with diethyl ether. The organic layer was washed with a saturated aqueous sodium hydrogen carbonate solution and brine successively and dried over anhydrous magnesium sulfate. The filtrate was concentrated under reduced pressure, and the obtained residue was purified by column chromatography on silica gel (ethyl acetate/hexane=1/1) to give the title compound (0.22 g).

$^1$H-NMR (CDCl$_3$) δ ppm: 1.55-1.80 (4H, m), 2.93 (3H, s), 3.25-3.40 (2H, m), 3.45-3.55 (2H, m), 4.51 (2H, s), 6.75-6.95 (3H, m), 7.15-7.40 (6H, m)

REFERENCE EXAMPLE 41

3-(4-Acetoxybutylsulfanyl)benzonitrile

3-Mercaptobenzonitrile (0.40 g) and potassium carbonate (0.61 g) were suspended in N,N-dimethylformamide (5 mL). To the reaction mixture was added 4-bromobutyl acetate (0.63 g), and the mixture was stirred at room temperature for 16 hours. To the reaction mixture was added 1 mol/L hydrochloric acid, and the resulting mixture was extracted with diethyl ether. The organic layer was washed with a saturated aqueous sodium hydrogen carbonate solution and brine successively and dried over anhydrous magnesium sulfate. The filtrate was concentrated under reduced pressure, and the obtained residue was purified by column chromatography on silica gel (ethyl acetate/hexane=1/5) to give the title compound (0.75 g).

$^1$H-NMR (CDCl$_3$) δ ppm: 1.65-1.90 (4H, m), 2.05 (3H, s), 2.94-3.05 (2H, m), 4.03-4.20 (2H, m), 7.30-7.60 (4H, m)

REFERENCE EXAMPLE 42

3-(4-Hydroxybutylsulfanyl)benzylamine

Lithium aluminum hydride (0.20 g) was suspended in tetrahydrofuran (15 mL). To the mixture was added 3-(4-acetoxy-butylsulfanyl)benzonitrile (0.75 g) under ice-cooling. The mixture was stirred at 60° C. for 2 hours, and the mixture was cooled under ice-cooling. To the reaction mixture were added dropwise ethanol and water successively, and then added diethyl ether. To the reaction mixture was added anhydrous sodium sulfate, and the insoluble material was removed by filtration. The filtrate was concentrated under reduced pressure to give the title compound (0.22 g).

$^1$H-NMR (CDCl$_3$) δ ppm: 1.60-1.85 (4H, m), 2.97 (2H, t, J=7.1 Hz), 3.67 (2H, t, J=6.1 Hz), 3.85 (2H, s), 7.05-7.40 (4H, m)

REFERENCE EXAMPLE 43

The following compounds were prepared in a similar manner to that described in Reference Example 42 using the corresponding materials.

3-(4-Benzyloxybutylamino)benzylamine $^1$H-NMR (CDCl$_3$) δ ppm: 1.60-1.80 (4H, m), 3.05-3.25 (2H, m), 3.44-3.60 (2H, m), 3.77 (2H, s), 4.51 (2H, s), 6.46 (1H, d, J=7.9 Hz), 6.52 (1H, s), 6.62 (1H, d, J=7.6 Hz), 7.14 (1H, dd, J=7.6 Hz, 7.9 Hz), 7.24-7.45 (5H, m)

3-[N-(4-Benzyloxybutyl)-N-methylamino]benzylamine $^1$H-NMR (CDCl$_3$) δ ppm: 1.55-1.80 (4H, m), 2.92 (3H, s), 3.25-3.40 (2H, m), 3.43-3.58 (2H, s), 3.79 (2H, s), 4.50 (2H, s), 6.50-6.70 (3H, m), 7.10-7.45 (6H, m)

REFERENCE EXAMPLE 44

3-Benzyloxy-4-formylbenzonitrile

4-Formyl-3-hydroxybenzonitrile (4.0 g) and potassium carbonate (3.76 g) were suspended in N,N-dimethylformamide (20 mL). To the reaction mixture was added benzylbromide (3.6 mL), and the mixture was stirred at room temperature for 16 hours. To the reaction mixture was added 1 mol/L hydrochloric acid, and the resulting mixture was extracted with diethyl ether. The organic layer was washed with a saturated aqueous sodium hydrogen carbonate solution and brine successively and dried over anhydrous magnesium sulfate. The filtrate was concentrated under reduced pressure, and the obtained residue was purified by column chromatography on silica gel (ethyl acetate/hexane=1/1) to give the title compound (3.0 g).

$^1$H-NMR (CDCl$_3$) δ ppm: 5.23 (2H, s), 7.30-7.50 (7H, m), 7.93 (1H, d, J=7.9 Hz), 10.55 (1H, s)

REFERENCE EXAMPLE 45

3-Benzyloxy-4-(3-hydroxypropyl)benzylamine

3-Benzyloxy-4-formylbenzonitrile (0.93 g) and (carboethoxymethyl)triphenylphosphonium bromide (2.52 g) were suspended in N,N-dimethylformamide (10 mL). To the reaction mixture was added potassium t-butoxide (0.66 g), and the mixture was stirred at room temperature for 18 hours. To the reaction mixture was added 1 mol/L hydrochloric acid, and the resulting mixture was extracted with ethyl acetate. The organic layer was washed with brine and dried over anhydrous magnesium sulfate. The filtrate was concentrated under reduced pressure. The obtained residue was dissolved in tetrahydrofuran (10 mL), and the mixture was added dropwise to a suspension of lithium aluminum hydride (0.20 g) in tetrahydrofuran (15 mL) under ice-cooling. The mixture was stirred at 60° C. for 2 hours. After mixture was cooled in an ice bath, and to the reaction mixture were added dropwise ethanol and water successively, and then added diethyl ether. To the reaction mixture was added anhydrous sodium sulfate, and the insoluble material was removed by filtration. The filtrate was concentrated under reduced pressure to give the title compound (0.20 g).

¹H-NMR (CDCl₃) δ ppm: 1.75-1.95 (2H, m), 2.75 (2H, t, J=7.3 Hz), 3.58 (2H, t, J=6.2 Hz), 3.85 (2H, t, J=6.2 Hz), 5.10 (2H, s), 6.88 (1H, d, J=7.6 Hz), 6.96 (1H, s), 7.14 (1H, d, J=7.6 Hz), 7.25-7.55 (5H, m)

REFERENCE EXAMPLE 46

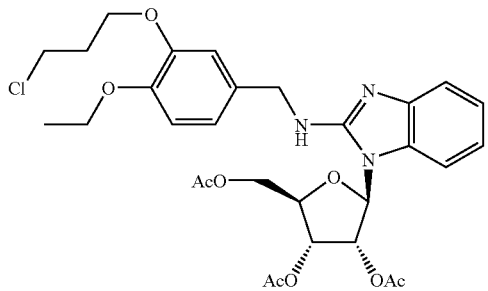

2-[3-(3-Chloropropoxy)-4-ethoxybenzylamino]-1-(2,3,5-tri-O-acetyl-β-D-ribofuranosyl)-1H-benzimidazole 2-Amino-1-(2,3,5-tri-O-acetyl-β-D-ribofuranosyl)-1H-benzimidazole (13.7 g) and 3-(3-chloropropoxy)-4-ethoxybenzaldehyde (15.3 g) were suspended in tetrahydrofuran (150 mL), and the mixture was stirred at 70° C. for 20 hours. To the stirred reaction mixture was added sodium triacetoxyborohydride (21.7 g) under ice-cooling, and the mixture was stirred at room temperature for 24 hours. To the reaction mixture was added water, and the resulting mixture was extracted with ethyl acetate. The organic layer was washed with brine and dried over anhydrous magnesium sulfate, and the filtrate was concentrated under reduced pressure. The obtained residue was purified by column chromatography on silica gel (eluent: ethyl acetate/hexane=1/3) to give the title compound (16.8 g).

¹H-NMR (CDCl₃) δ ppm: 1.42 (3H, t, J=7.1 Hz), 1.83 (3H, s), 1.97 (3H, s), 2.15 (3H, s), 2.20-2.30 (2H, m), 3.76 (2H, t, J=6.6 Hz), 3.95-4.40 (6H, m), 4.47 (1H, dd, J=3.6 Hz, 12.4 Hz), 4.68 (2H, s), 5.20-5.45 (2H, m), 5.57 (1H, dd, J=6.8 Hz, 7.4 Hz), 6.01 (1H, d, J=7.4 Hz), 6.83 (1H, d, J=8.1 Hz), 6.92 (1H, dd, J=2.1 Hz, 8.1 Hz), 6.99 (1H, d, J=2.1 Hz), 7.02-7.25 (3H, m), 7.49 (1H, d, J=7.8 Hz)

REFERENCE EXAMPLE 47

The following compounds were prepared in a similar manner to that described in Reference Example 46 using the corresponding materials.

2-[3-(3-Chloropropoxy)benzylamino]-1-(2,3,5-tri-O-acetyl-β-D-ribofuranosyl)-1H-benzimidazole ¹H-NMR (CDCl₃) δ ppm: 1.81 (3H, s), 1.98 (3H, s), 2.15 (3H, s), 2.18-2.30 (2H, m), 3.73 (2H, t, J=6.6 Hz), 4.10 (2H, t, J=6.0 Hz), 4.22 (1H, dd, J=2.4 Hz, 12.5 Hz), 4.30-4.38 (1H, m), 4.49 (1H, d, J=3.4 Hz, 12.5 Hz), 4.65-4.85 (2H, m), 5.30-5.45 (2H, m), 5.56 (1H, dd, J=6.4 Hz, 7.6 Hz), 6.03 (1H, d, J=7.6 Hz), 6.81 (1H, dd, J=2.2 Hz, 8.1 Hz), 6.90-7.00 (2H, m), 7.03-7.30 (4H, m), 7.49 (1H, d, J=7.6 Hz)

2-[4-Benzyloxy-3-(3-chloropropoxy)benzylamino]-1-(2,3,5-tri-O-acetyl-β-D-ribofuranosyl)-1H-benzimidazole ¹H-NMR (CDCl₃) δ ppm: 1.80 (3H, s), 1.97 (3H, s), 2.15 (3H, s), 2.18-2.30 (2H, m), 3.74 (2H, t, J=6.5 Hz), 4.05-4.40 (4H, m), 4.46 (1H, d, J=3.5 Hz, 12.5 Hz), 4.67 (2H, d, J=5.2 Hz), 5.10 (2H, s), 5.25-5.40 (2H, m), 5.57 (1H, dd, J=6.5 Hz, 7.3 Hz), 6.00 (1H, d, J=7.3 Hz), 6.80-7.60 (12H, m)

2-[3-(3-Chloropropoxy)-4-phenylbenzylamino]-1-(2,3,5-tri-O-acetyl-β-D-ribofuranosyl)-1H-benzimidazole ¹H-NMR (CDCl₃) δ ppm: 1.83 (3H, s), 1.98 (3H, s), 2.05-2.25 (5H, m), 3.55-3.65 (2H, m), 4.00-4.40 (4H, m), 4.52 (1H, d, J=3.4 Hz, 12.5 Hz), 4.70-4.90 (2H, m), 5.30-5.50 (2H, m), 5.50 (1H, dd, J=6.5 Hz, 7.8 Hz), 6.04 (1H, d, J=7.8 Hz), 7.00-7.60 (12H, m)

2-{4-[3-(3-Chloropropoxy)phenyl]benzylamino}-1-(2,3,5-tri-O-acetyl-β-D-ribofuranosyl)-1H-benzimidazole ¹H-NMR (CDCl₃) δ ppm: 1.77 (3H, s), 2.00 (3H, s), 2.16 (3H, s), 2.20-2.35 (2H, m), 3.60-3.85 (2H, m), 4.10-4.30 (4H, m), 4.50 (1H, d, J=3.5 Hz, 12.7 Hz), 4.75-4.90 (2H, m), 5.30-5.50 (2H, m), 5.57 (1H, dd, J=6.5 Hz, 7.7 Hz), 6.04 (1H, d, J=7.7 Hz), 6.85-7.60 (12H, m)

2-[3-(3-Chloropropoxy)-4-methoxybenzylamino]-1-(2,3,5-tri-O-acetyl-β-D-ribofuranosyl)-1H-benzimidazole 2-[3-(3-Chloropropoxy)-4-propoxybenzylamino]-1-(2,3,5-tri-O-acetyl-β-D-ribofuranosyl)-1H-benzimidazole

EXAMPLE 1

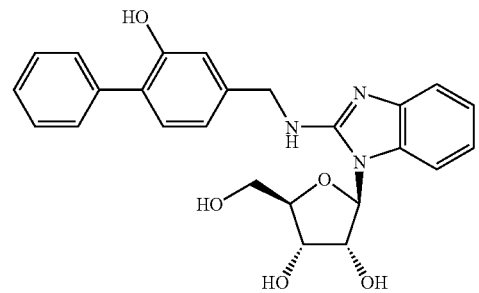

2-(3-Hydroxy-4-phenylbenzylamino)-1-(β-D-ribofuranosyl)-1H-benzimidazole

2-Chloro-1-(β-D-ribofuranosyl)-1H-benzimidazole (0.21 g) and 3-hydroxy-4-phenylbenzylamine (0.19 g) were suspended in isobutanol (5 mL). To the mixture was added triethylamine (0.36 mL), and the mixture was stirred for reflux for 16 hours. The reaction mixture was concentrated under reduced pressure, and the obtained residue was purified by column chromatography on silica gel (eluent: methanol/ethyl acetate=1/20) to give the title compound (0.1 g).

¹H-NMR (DMSO-d₆) δ ppm: 3.60-3.80 (2H, m), 3.90-4.20 (2H, m), 4.35-4.65 (3H, m), 5.21 (1H, d, J=4.4 Hz), 5.25 (1H, d, J=7.4 Hz), 5.56 (1H, t, J=4.0 Hz), 5.82 (1H, d, J=7.4 Hz), 6.80-7.01 (4H, m), 7.10-7.60 (9H, m), 9.44 (1H, s)

EXAMPLES 2-12

The compounds of Tables 1 and 2 were prepared in a similar manner to that described in Example 1 using the corresponding materials.

TABLE 1

| Example No. | Structure | ¹H-NMR δ ppm: |
|---|---|---|
| Example 2 | 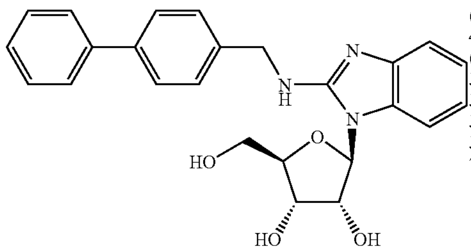 | (DMSO-d₆) 3.60-3.80 (2 H, m), 3.95-4.03 (1 H, m), 4.06-4.18 (1 H, m), 4.35-4.50 (1 H, m), 4.55-4.70 (2 H, m), 5.19 (1 H, d, J = 4.4 Hz), 5.29 (1 H, d, J = 7.4 Hz), 5.60 (1 H, t, J = 4.5 Hz), 5.83 (1 H, d, J = 7.3 Hz), 6.80-7.03 (2 H, m), 7.17 (1 H, d, J = 7.3 Hz), 7.29 (1 H, d, J = 7.3 Hz), 7.34 (1 H, t, J = 7.4 Hz), 7.40-7.48 (4 H, m) 7.50 (1 H, t, J = 6.1 Hz), 7.57-7.67 (4 H, m) |
| Example 3 | 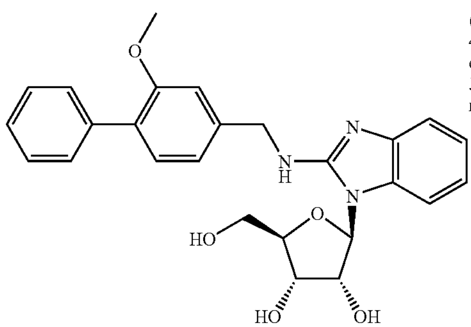 | (DMSO-d₆) 3.60-3.80 (5 H, m), 3.95-4.20 (2 H, m), 4.40-4.50 (1 H, m), 4.61 (2 H, d, J = 6.2 Hz), 5.21 (1 H, d, J = 4.4 Hz), 5.31 (1 H, d, J = 7.6 Hz), 5.63 (1 H, t, J = 4.4 Hz), 5.84 (1 H, d, J = 7.8 Hz), 6.80-7.07 (3 H, m), 7.10-7.46 (9 H, m), 7.50 (1 H, t, J = 6.2 Hz) |
| Example 4 | 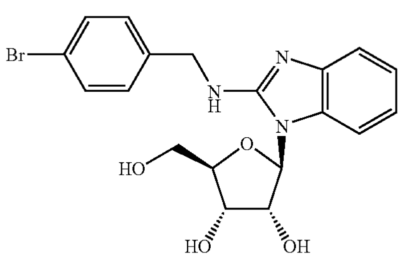 | (DMSO-d₆) 3.60-3.80 (2 H, m), 3.95-4.02 (1 H, m), 4.05-4.15 (1 H, m), 4.30-4.45 (1 H, m), 4.46-4.64 (2 H, m), 5.19 (1 H, d, J = 4.2 Hz), 5.29 (1 H, d, J = 7.5 Hz), 5.57 (1 H, t, J = 4.3 Hz), 5.80 (1 H, d, J = 7.8 Hz), 6.88 (1 H, t, J = 7.5 Hz), 6.93 (1 H, t, J = 7.5 Hz), 7.16 (1 H, d, J = 7.5 Hz), 7.28 (1 H, d, J = 7.5 Hz), 7.32 (1 H, d, J = 8.4 Hz), 7.40-7.60 (3 H, m) |
| Example 5 | 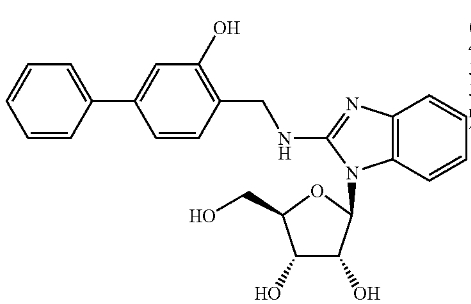 | (DMSO-d₆) 3.60-3.80 (2 H, m), 3.96-4.04 (1 H, m) 4.07-4.16 (1 H, m), 4.30-4.60 (3 H, m), 5.22 (1 H, d, J = 4.4 Hz), 5.35 (1 H, d, J = 7.6 Hz), 5.78 (1 H, t, J = 4.1 Hz), 5.80 (1 H, d, J = 4.7 Hz), 6.90-7.10 (4 H, m), 7.20-7.37 (4 H, m), 7.39-7.47 (2 H, m), 7.55-7.62 (2 H, m), 11.74 (1 H, s) |

TABLE 1-continued

| Example No. | Structure | ¹H-NMR δ ppm: |
|---|---|---|
| Example 6 | 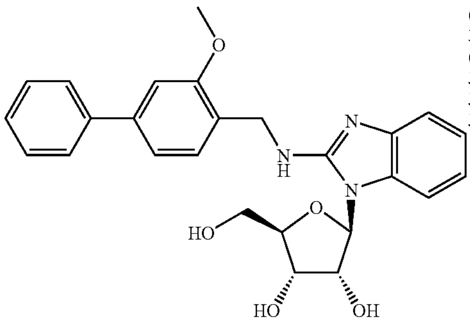 | (DMSO-d$_6$) 3.60-3.75 (2 H, m), 3.94 (3 H, s), 3.96-4.04 (1 H, m), 4.08-4.16 (1 H, m), 4.40-4.70 (3 H, m), 5.22 (1 H, d, J = 4.4 Hz), 5.36 (1 H, d, J = 7.6 Hz), 5.55 (1 H, t, J = 4.4 Hz), 5.85 (1 H, d, J = 7.6 Hz), 6.88 (1 H, t, J = 7.6 Hz), 6.94 (1 H, t, J = 7.6 Hz), 7.10-7.50 (9 H, m), 7.60-7.70 (2 H, m) |
| Example 7 | 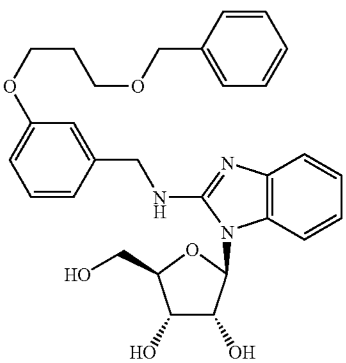 | (DMSO-d$_6$) 1.85-2.05 (2 H, m), 3.57 (2 H, t, J = 6.3 Hz), 3.60-3.80 (2 H, m), 3.95-4.15 (4 H, m), 4.35-4.60 (5 H, m), 5.81 (1 H, d, J = 4.4 Hz), 6.70-7.50 (14 H, m) |

TABLE 2

| Example No. | Structure | ¹H-NMR δ ppm: |
|---|---|---|
| Example 8 | 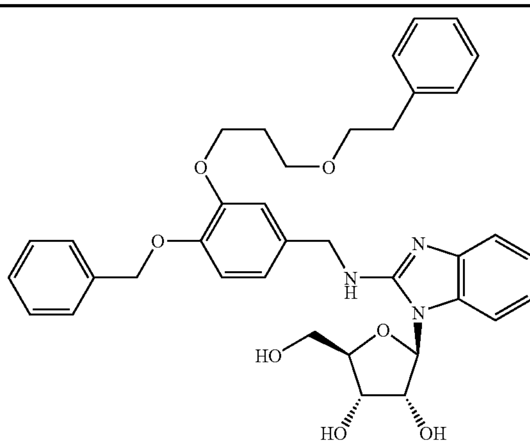 | (DMSO-d$_6$) 1.60-1.85 (4 H, m), 3.46 (2 H, t, J = 6.2 Hz), 3.60-3.75 (2 H, m), 3.90-4.02 (3 H, m), 4.06-4.14 (1 H, m), 4.35-4.53 (5 H, m), 5.04 (2 H, s), 5.18 (1 H, d, J = 4.5 Hz), 5.26 (1 H, d, J = 7.5 Hz), 5.56 (1 H, t, J = 4.6 Hz), 5.80 (1 H, d, J = 7.4 Hz), 6.80-7.06 (5 H, m), 7.10-7.50 (13 H, m) |
| Example 9 | 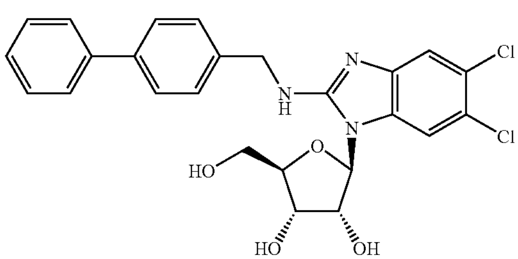 | (DMSO-d$_6$) 3.60-3.80 (2 H, m), 3.95-4.15 (2 H, m), 4.30-4.45 (1 H, m), 4.61 (2 H, d, J = 6.0 Hz), 5.25 (1 H, d, J = 4.5 Hz), 5.32 (1 H, d, J = 7.6 Hz), 5.68 (1 H, t, J = 4.5 Hz), 5.83 (1 H, d, J = 7.7 Hz), 7.34 (1 H, t, J = 7.4 Hz), 7.37 (1 H, s), 7.40-7.49 (4 H, m), 7.55-7.66 (4 H, m), 7.70 (1 H, s), 7.83 (1 H, t, J = 6.0 Hz) |

TABLE 2-continued

| Example No. | Structure | $^1$H-NMR δ ppm: |
|---|---|---|
| Example 10 | 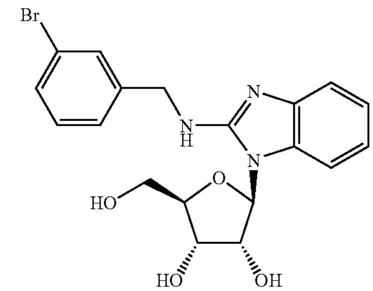 | (CD$_3$OD) 3.75-3.90 (2 H, m), 4.05-4.15 (1 H, m), 4.26 (1 H, J = 2.4 Hz, 5.9 Hz), 4.58 (1 H, dd, J = 5.9 Hz, 7.3 Hz), 4.61 (2 H, s), 5.97 (1 H, d, J = 7.3 Hz), 6.90-7.10 (2 H, m), 7.15-7.45 (5 H, m), 7.57 (1 H, s) |
| Example 11 | 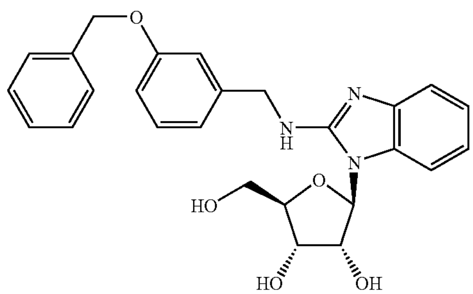 | (CDCl$_3$) 3.60-3.80 (2 H, m), 4.05-4.15 (4 H, m), 4.55-4.65 (1 H, m), 5.01 (2 H, s), 5.80 (1 H, d, J = 6.9 Hz), 6.08 (1 H, brs), 6.70-6.90 (3 H, m), 6.95-7.50 (10 H, m) |
| Example 12 | 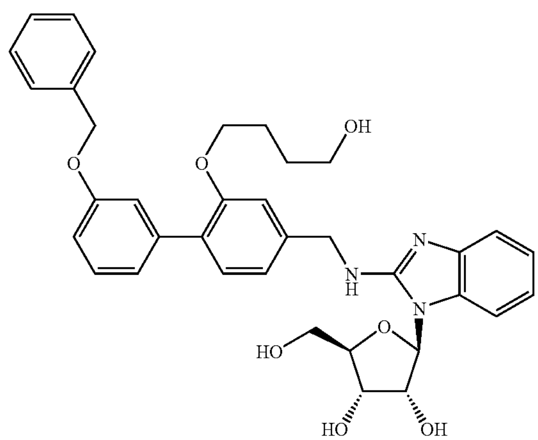 | (DMSO-d$_6$) 1.43-1.55 (2 H, m), 1.60-1.75 (2 H, m), 3.33-3.45 (2 H, m), 3.60-3.80 (2 H, m), 3.90-4.20 (4 H, m) 3 4.35-4.50 (2 H, m), 4.59 (2 H, d, J = 6.0 Hz), 5.11 (2 H, s), 5.21 (1 H, d, J = 4.5 Hz), 5.29 (1 H, d, J = 7.5 Hz), 5.63 (1 H, t, J = 4.5 Hz), 5.83 (1 H, d, J = 7.2 Hz), 6.80-7.60 (17 H, m) |

EXAMPLE 13

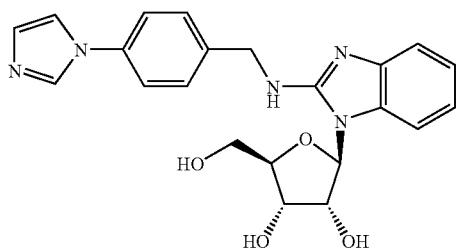

2-[4-(1H-Imidazol-1-yl)benzylamino]-1-(β-D-ribofuranosyl)-1H-benzimidazole

2-Amino-1-(2,3,5-tri-O-acetyl-β-D-ribofuranosyl)-1H-benzimidazole (94 mg) and 4-(1H-imidazol-1-yl)benzaldehyde (41 mg) were suspended in tetrahydrofuran (3 mL), and the mixture stirred at room temperature for 2 hours. To the reaction mixture was added acetic acid (200 μL), and then was added sodium triacetoxyborohydride (56 mg). The mixture was stirred at room temperature for 24 hours. After adding water to the reaction mixture, and the mixture was concentrated under reduced pressure. The obtained residue was dissolved in ethanol (2 mL). To the mixture was added 5 mol/L aqueous sodium hydroxide solution (0.5 mL), and the mixture was stirred at room temperature for 1 hour. To the reaction mixture was added acetic acid (1 mL), and the mixture was concentrated under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (67 mg).

$^1$H-NMR (CD$_3$OD) δ ppm: 3.75-3.90 (2H, m), 4.08-4.18 (1H, m), 4.26 (1H, dd, J=2.1 Hz, 5.6 Hz), 4.60 (1H, dd, J=5.6 Hz, 7.6 Hz), 4.66 (1H, d, J=15.8 Hz), 4.71 (1H, d, J=15.8 Hz), 5.97 (1H, d, J=7.6 Hz), 6.94-7.07 (2H, m), 7.12 (1H, s), 7.20-7.32 (2H, m), 7.45-7.60 (5H, m), 8.51 (1H, s)

EXAMPLE 14

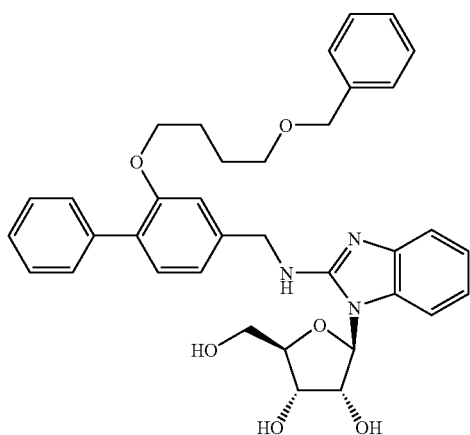

2-[3-(4-Benzyloxybutoxy)-4-phenylbenzylamino]-1-(β-D-ribofuranosyl)-1H-benzimidazole 2-(3-Hydroxy-4-phenylbenzylamino)-1-(β-D-ribofuranosyl)-1H-benzimidazole (70 mg) and potassium carbonate (65 mg) were suspended in N,N-dimethylformamide (1 mL). To the mixture was added benzyl 4-bromobutylether (45 μL), and the mixture was stirred at 50° C. for 16 hours. The insoluble material was removed by filtration, and the reaction mixture was concentrated under reduced pressure. The obtained residue was purified by column chromatography on silica gel (eluent methanol/ethyl acetate=1/20) to give the title compound (54 mg).

$^1$H-NMR (DMSO-d$_6$) δ ppm: 1.50-1.80 (4H, m), 3.39 (2H, t, J=6.3 Hz), 3.60-3.80 (2H, m), 3.90-4.20 (4H, m), 4.39 (2H, s), 4.41-4.50 (1H, m), 4.59 (2H, d, J=5.9 Hz), 5.21 (1H, d, J=4.4 Hz), 5.31 (1H, d, J=7.1 Hz), 5.62 (1H, t, J=4.4 Hz), 5.83 (1H, d, J=7.5 Hz), 6.89 (1H, t, J=7.6 Hz), 6.95 (1H, t, J=7.6 Hz), 7.02 (1H, d, J=7.6 Hz), 7.10-7.60 (15H, m)

EXAMPLES 15-27

The compounds of Tables 3 to 6 were prepared in a similar manner to that described in Example 14 using the corresponding materials.

TABLE 3

| Example No. | Structure | $^1$H-NMR δ ppm: |
|---|---|---|
| Example 15 | 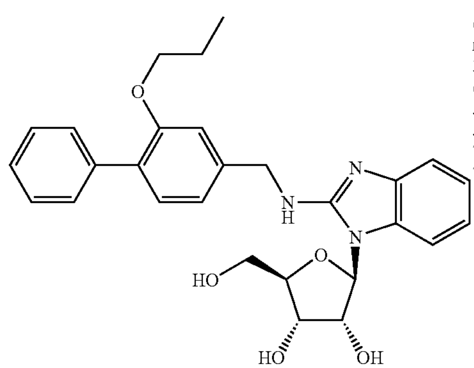 | (DMSO-d$_6$) 0.89 (3 H, t, J = 7.5 Hz), 1.50-1.70 (2 H, m), 3.60-3.80 (2 H, m), 3.92 (2 H, t, J = 6.1 Hz), 3.98-4.05 (1 H, m), 4.08-4.16 (1 H, m), 4.40-4.50 (1 H, m), 4.59 (2 H, d, J = 6.0 Hz), 5.83 (1 H, d, J = 7.4 Hz), 6.89 (1 H, t, J = 7.6 Hz), 6.95 (1 H, t, J = 7.6 Hz), 7.01 (1 H, d, J = 7.6 Hz), 7.13 (1 H, s), 7.17 (1 H, d, J = 7.6 Hz), 7.22 (1 H, d, J = 7.3 Hz), 7.24-7.55 (7 H, m) |
| Example 16 | 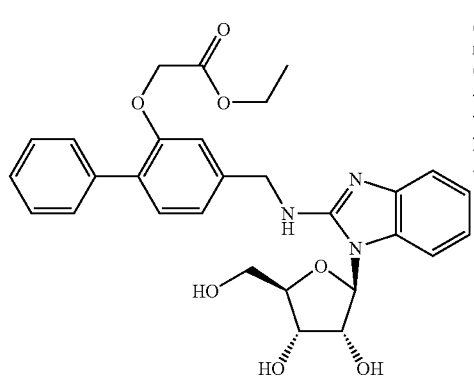 | (DMSO-d$_6$) 1.16 (3 H, t, J = 7.1 Hz), 3.60-3.80 (2 H, m), 3.95-4.20 (4 H, m), 4.35-4.50 (1 H, m), 4.58 (2 H, d, J = 7.0 Hz), 4.75 (2 H, s), 5.21 (1 H, d, J = 4.4 Hz), 5.28 (1 H, d, J = 7.2 Hz), 5.61 (1 H, t, J = 4.5 Hz), 5.83 (1 H, d, J = 7.5 Hz), 6.89 (1 H, t, J = 7.6 Hz) . 6.95 (1 H, t, J = 7.6 Hz), 7.02 (1 H, s), 7.05 (1 H, d, J = 7.6 Hz), 7.17 (1 H, d, J = 7.6 Hz), 7.25 (1 H, d, J = 7.8 Hz), 7.26-7.58 (7 H, m) |

TABLE 4

| Example No. | Structure | $^1$H-NMR δ ppm: |
| --- | --- | --- |
| Example 17 | 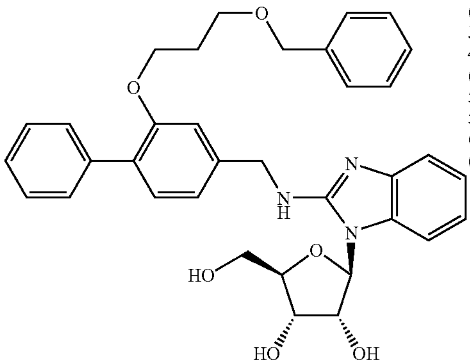 | (DMSO-d$_6$) 1.80-2.00 (2 H, m), 3.48 (2 H, t, J = 6.3 Hz), 3.60-3.80 (2 H, m), 3.05-4.02 (1 H, m), 4.04 (2 H, t, J = 6.0 Hz), 4.09-4.15 (1 H, m), 4.41 (2 H, s), 4.40-4.48 (1 H, m), 4.55-4.65 (2 H, m), 5.20 (1 H, d, J = 4.4 Hz), 5.29 (1 H, d, J = 7.1 Hz), 5.63 (1 H, t, J = 4.4 Hz), 5.83 (1 H, d, J = 7.7 Hz), 6.89 (1 H, t, J = 7.6 Hz), 6.95 (1 H, t, J = 7.6 Hz), 7.02 (1 H, d, J = 7.6 Hz), 7.10-7.60 (15 H, m) |
| Example 18 | 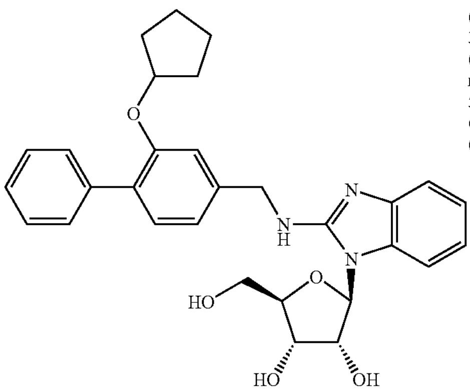 | (DMSO-d$_6$) 1.40-1.90 (8 H, m), 3.60-3.80 (2 H, m), 3.95-4.05 (1 H, m), 4.08-4.15 (1 H, m), 4.40-4.50 (1 H, m), 4.80 (2 H, d, J = 6.2 Hz), 4.70-4.85 (1 H, m), 5.21 (1 H, d, J = 4.4 Hz), 5.29 (1 H, d, J = 7.7z), 5.64 (1 H, t, J = 4.4 Hz), 5.83 (1 H, d, J = 7.6 Hz), 6.89 (1 H, t, J = 7.6 Hz), 6.95 (1 H, t, J = 7.6 Hz), 6.99 (1 H, d, J = 7.6 Hz), 7.07-7.60 (10 H, m) |
| Example 19 | 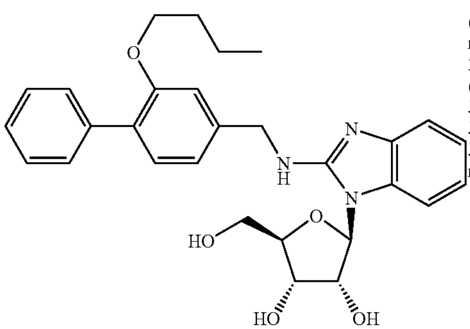 | (DMSO-d$_6$) 0.85 (3 H, t, J = 7.4 Hz), 1.25-1.43 (2 H, m), 1.53-1.70 (2 H, m), 3.60-3.80 (2 H, m), 3.90-4.20 (4 H, m), 4.40-4.50 (1 H, m), 4.55-4.65 (2 H, m), 5.21 (1 H, d, J = 4.4 Hz), 5.29 (1 H, d, J = 7.1 Hz), 5.63 (1 H, t, J = 4.4 Hz), 5.83 (1 H, d, J = 7.6 Hz), 6.89 (1 H, t, J = 7.6 Hz), 6.95 (1 H, t, J = 7.6 Hz), 7.01 (1 H, d, J = 7.6 Hz), 7.08-7.60 (10 H, m) |
| Example 20 | 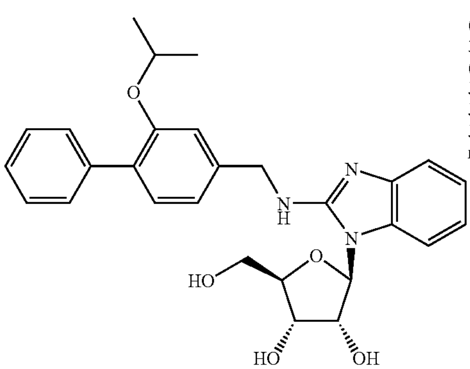 | (DMSO-d$_6$) 1.10-1.30 (6 H, m), 3.60-3.80 (2 H, m), 3.95-4.05 (1 H, m), 4.08-4.16 (1 H, m), 4.35-4.65 (4 H, m), 5.21 (1 H, t, J = 4.4 Hz), 5.29 (1 H, d, J = 7.5 Hz), 5.64 (1 H, t, J = 4.4 Hz), 5.83 (1 H, d, J = 7.5 Hz), 6.89 (1 H, t, J = 7.6 Hz), 6.95 (1 H, t, J = 7.6 Hz), 6.99 (1 H, d, J = 7.6 Hz), 7.10-7.60 (10 H, m) |

TABLE 4-continued
| Example No. | Structure | $^1$H-NMR δ ppm: |
| --- | --- | --- |
| Example 21 | 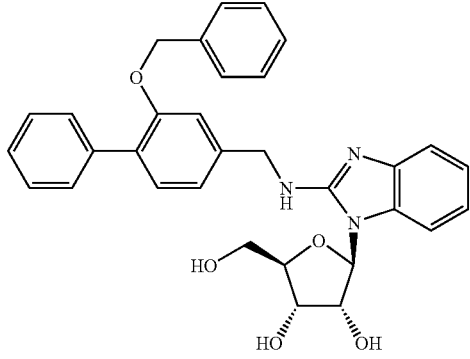 | (DMSO-$d_6$) 3.60-3.80 (2 H, m), 3.95-4.05 (1 H, m), 4.08-4.16 (1 H, m), 4.40-4.52 (1 H, m), 4.56-4.70 (2 H, m), 5.09 (2 H, s), 5.22 (1 H, d, J = 4.4 Hz), 5.31 (1 H, d, J = 7.4 Hz), 5.63 (1 H, t, J = 4.4Hz), 5.85 (1 H, t, J = 7.6 Hz), 7.04 (1 H, d, J = 7.6 Hz), 7.15-7.60 (15 H, m) |
TABLE 5
| Example No. | Structure | $^1$H-NMR δ ppm: |
| --- | --- | --- |
| Example 22 | 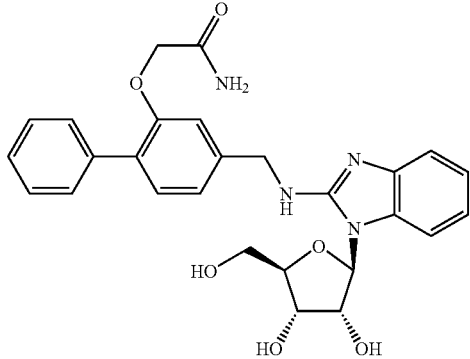 | (DMSO-$d_6$) 3.60-3.80 (2 H, m), 3.96-4.04 (1 H, m), 4.08-4.18 (1 H, m), 4.35-4.50 (3 H, m), 4.58 (2 H, d, J = 6.0 Hz), 5.23 (1 H, d, J = 4.5 Hz), 5.32 (1 H, d, J = 7.3 Hz), 5.62 (1 H, t, J = 4.4 Hz), 5.83 (1 H, d, J = 7.6 Hz), 6.89 (1 H, t, J = 7.6 Hz), 6.95 (1 H, t, J = 7.6 Hz), 7.00-7.60 (13 H, m) |
| Example 23 | 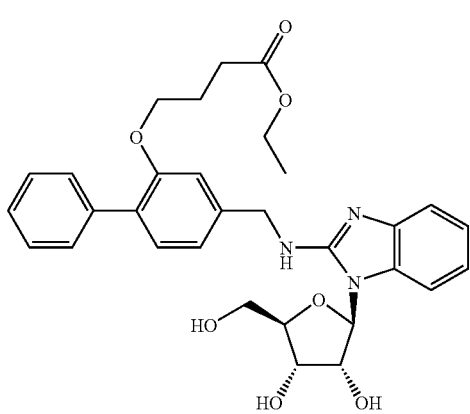 | (DMSO-$d_6$) 1.15 (3 H, t, J = 7.0 Hz), 1.80-1.95 (2 H, m), 2.30-2.40 (2 H, m), 3.60-3.80 (2 H, m), 3.90-4.20 (6 H, m), 4.35-4.50 (1 H, m), 4.58 (2 H, d, J = 7.0 Hz), 5.21 (1 H, d, J = 4.4 Hz), 5.28 (1 H, d, J = 7.2 Hz), 5.61 (1 H, t, J = 4.5 Hz), 5.83 (1 H, d, J = 7.5 Hz), 8.89 (1 H, t, J = 7.6 Hz), 6.95 (1 H, t, J = 7.6 Hz), 7.02 (1 H, d, J = 7.6 Hz), 7.12 (1 H, s), 7.17 (1 H, d, J = 7.6 Hz), 7.22 (1 H, d, J = 7.6 Hz), 7.26-7.58 (7 H, m) |

TABLE 5-continued

| Example No. | Structure | $^1$H-NMR δ ppm: |
|---|---|---|
| Example 24 | 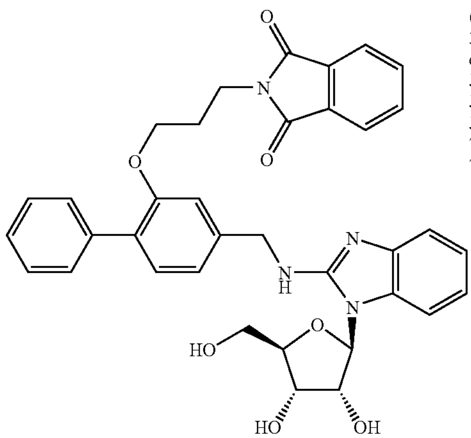 | (DMSO-d$_6$) 1.90-2.10 (2 H, m), 3.60-3.80 (4 H, m), 3.90-4.20 (4 H, m), 4.35-4.50 (1 H, m), 4.58 (2 H, d, J = 7.0 Hz), 5.21 (1 H, d, J = 4.4 Hz), 5.28 (1 H, d, J = 7.2 Hz), 5.63 (1 H, t, J = 4.5 Hz), 5.82 (1 H, d, J = 7.5 Hz), 6.89 (1 H, t, J = 7.6 Hz), 6.95 (1 H, t, J = 7.6 Hz), 7.02 (1 H, d, J = 7.6 Hz), 7.08 (1 H, s), 7.16 (1 H, d, J = 7.6 Hz), 7.18-1.70 (5 H, m), 7.45-7.60 (3 H, m), 7.75-7.90 (4 H, m) |
| Example 25 | 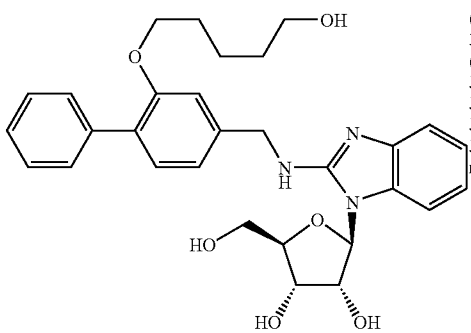 | (DMSO-d$_6$) 1.25-1.45 (4 H, m), 1.55-1.70 (2 H, m), 3.25-3.40 (2 H, m), 3.60-3.80 (2 H, m), 3.90-4.20 (4 H, m), 4.35-4.50 (1 H, m), 4.59 (2 H, d, J = 6.3 Hz), 5.21 (1 H, d. J = 4.4 Hz), 5.30 (1 H, d, J = 7.5 Hz), 5.63 (1 H, t, J = 4.4 Hz), 5.83 (1 H, d, J = 7.5 Hz), 6.88 (1 H, t, J = 7.6 Hz), 6.95 (1 H, t, J = 7.6 Hz), 7.01 (1 H, d, 47.6 Hz), 7.10-7.60 (10 H, m) |
| Example 26 | 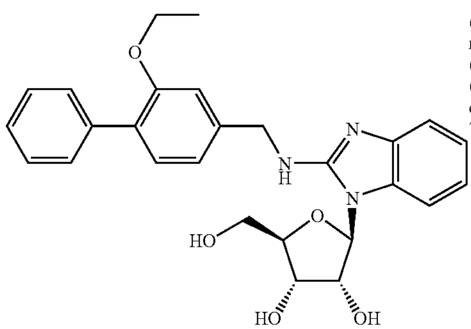 | (DMSO-d$_6$) 1.24 (3 H, t, J = 6.9 Hz), 3.60-3.80 (2 H, m), 3.95-4.20 (4 H, m), 4.35-4.50 (1 H, m), 4.59 (2 H, d, J = 5.8 Hz), 5.83 (1 H, d, J = 7.8 Hz), 6.88 (1 H, t, J = 7.6 Hz), 6.95 (1 H, t, J = 7.6 Hz), 7.01 (1 H, d, J = 7.6 Hz), 7.12 (1 H, s), 7.17 (1 H, d, J = 7.6 Hz), 7.21 (1 H, d, J = 7.9 Hz), 7.24-7.55 (7 H, m) |

TABLE 6

| Example No. | Structure | $^1$H-NMR δ ppm: |
|---|---|---|
| Example 27 | 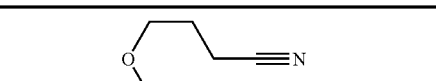 | (CD$_3$OD) 1.90-2.02 (2 H, m), 2.40 (2 H, t, J = 7.2 Hz), 3.78-3.90 (2 H, m), 4.04 (2 H, t, J = 5.7 Hz), 4.10-4.20 (1 H, m), 4.28 (1 H, dd, J = 2.1 Hz, 5.6 Hz), 4.55-4.75 (3 H, m) 1 5.98 (1 H, d, J = 7.0 Hz), 6.90-7.50 (13 H, m) |

EXAMPLE 28

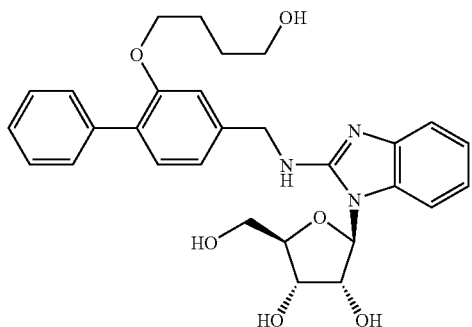

2-[3-(4-Hydroxybutoxy)-4-phenylbenzylamino]-1-(β-D-ribofuranosyl)-1H-benzimidazole 2-[3-(4-Benzyloxybutoxy)-4-phenylbenzylamino]-1-(β-D-ribofuranosyl)-1H-benzimidazole (35 mg) was dissolved in ethanol (5 mL). To the solution was added a catalytic amount of 10% palladium-carbon powder, and the mixture was stirred at 60° C. under a hydrogen atmosphere for 24 hour. The insoluble material was removed by filtration, and the solvent of the filtrate was removed under reduced pressure to give the title compound (21 mg).

$^1$H-NMR (DMSO-$d_6$) δ ppm: 1.40-1.55 (2H, m), 1.60-1.75 (2H, m), 3.30-3.45 (2H, m), 3.60-3.80 (2H, m), 3.90-4.20 (4H, m), 4.35-4.50 (2H, m), 4.59 (2H, d, J=6.3 Hz), 5.21 (1H, d, J=4.4 Hz), 5.30 (1H, d, J=7.5 Hz), 5.63 (1H, t, J=4.4 Hz), 5.83 (1H, d, J=7.5 Hz), 6.88 (1H, t, J=7.6 Hz), 6.95 (1H, t, J=7.6 Hz), 7.01 (1H, d, J=7.6 Hz), 7.10-7.60 (10H, m)

EXAMPLES 29-33

The compounds of Table 7 were prepared in a similar manner to that described in Example 28 using the corresponding materials.

TABLE 7

| Example No. | Structure | $^1$H-NMR δ ppm: |
|---|---|---|
| Example 29 | 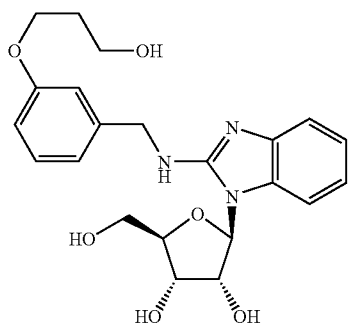 | (DMSO-$d_6$) 1.75-1.95 (2 H, m), 3.48-3.58 (2 H, m), 3.62-3.76 (2 H, m), 3.96-4.03 (3 H, m), 4.07-4.14 (1 H, m), 4.36-4.46 (1 H, m), 4.49-4.57 (2 H, m), 5.21 (1 H, d, J = 4.4 Hz), 5.30 (1 H, d, J = 7.4 Hz), 5.60 (1 H, t, J = 4.4 Hz), 5.81 (1 H, d, J = 7.4 Hz), 6.70-7.00 (5 H, m), 7.16 (1 H, d, J = 7.8 Hz), 7.19 (1 H, t, J = 7.8 Hz), 7.28 (1 H, d, J = 7.8 Hz), 7.45 (1 H, t, J = 6.5 Hz) |
| Example 30 | 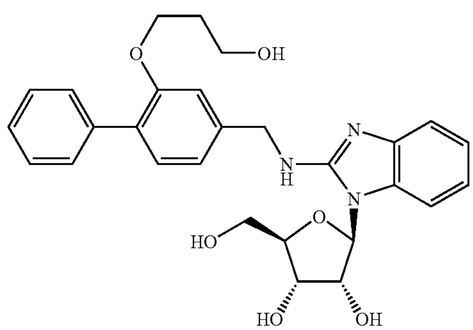 | (DMSO-$d_6$) 1.70-1.85 (2 H, m), 3.40-3.55 (2 H, m), 3.65-3.80 (2 H, m), 3.95-4.20 (4 H, m), 4.35-4.42 (2 H, m), 4.59 (2 H, d, J = 6.3 Hz), 5.21 (1 H, d, J = 4.4 Hz), 5.30 (1 H, d, J = 7.4 Hz), 5.63 (1 H, t, J = 4.4 Hz), 5.83 (1 H, d, J = 7.5 Hz), 6.88 (1 H, t, J = 7.6 Hz), 6.95 (1 H, t, J = 7.6 Hz), 7.01 (1 H, d, J = 7.6 Hz), 7.10-7.60 (10 H, m) |
| Example 31 | 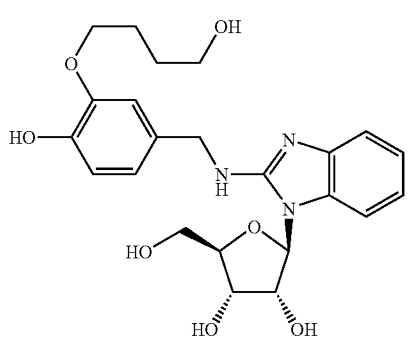 | (DMSO-$d_6$) 1.47-1.62 (2 H, m), 1.66-1.80 (2 H, m), 3.43 (2 H, t, J = 6.8 Hz), 3.60-3.75 (2 H, m), 3.85-4.02 (3 H, m), 4.05-4.15 (1 H, m), 4.30-4.50 (3 H, m), 5.79 (1 H, d, J = 7.7 Hz), 6.69 (1 H, d, J = 7.9 Hz), 6.75 (1 H, dd, J = 1.8 Hz, 7.9 Hz), 6.80-7.00 (3 H, m), 7.10-7.40 (3 H, m) |

TABLE 7-continued

| Example No. | Structure | $^1$H-NMR δ ppm: |
|---|---|---|
| Example 32 | 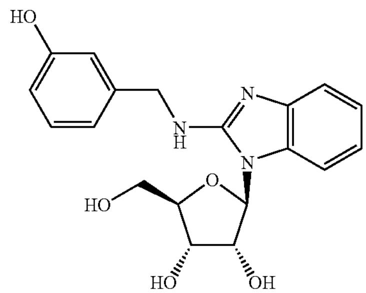 | (CD$_3$OD) 3.70-3.90 (2 H, m), 4.05-4.15 (1 H, m), 4.25 (1 H, dd, J = 2.3 Hz, 5.7 Hz), 4.45-4.70 (3 H, m), 5.95 (1 H, d, J = 7.8 Hz), 6.63 (1 H, dd, J = 2.0 Hz, 8.0 Hz), 6.75-6.90 (2 H, m), 6.94-7.15 (3 H, m), 7.10-7.22 (2 H, m) |
| Example 33 | 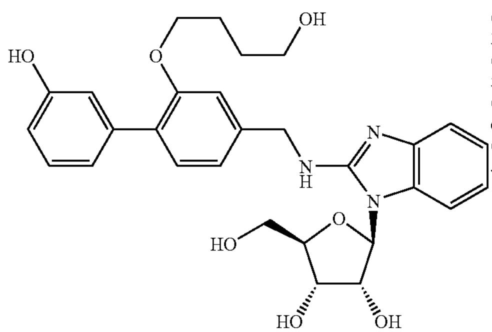 | (DMSO-d$_6$) 1.40-1.55 (2 H, m), 1.60-1.75 (2 H, m), 3.33-3.45 (2 H, m), 3.60-3.80 (2 H, m), 3.90-4.20 (4 H, m), 4.30-4.50 (2 H, m), 4.59 (2 H, d, J = 5.9 Hz), 5.22 (1 H, d, J = 3.9 Hz), 5.31 (1 H, d, J = 7.4 Hz), 5.63 (1 H, t, J = 4.0 Hz), 5.83 (1 H, d, J = 7.7 Hz), 6.67 (1 H, dd, J = 1.8 Hz, 7.8 Hz) . 6.80-7.03 (5 H, m), 7.08-7.25 (4 H, m), 7.29 (1 H, d, J = 7.8 Hz), 7.45 (1 H, t, J = 5.9 Hz), 9.29 (1 H, s) |

EXAMPLE 34

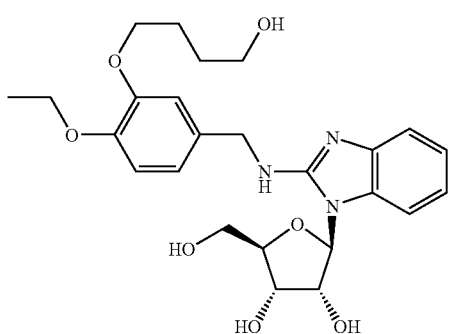

2-[4-Ethoxy-3-(4-hydroxybutoxy)benzylamino]-1-(β-D-ribofuranosyl)-1H-benzimidazole 2-[4-Hydroxy-3-(4-hydroxybutoxy)benzylamino]-1-(β-D-ribofuranosyl)-1H-benzimidazole (30 mg) and potassium carbonate (18 mg) was suspended in N,N-dimethylformamide (0.7 mL). To the mixture was added ethyl iodide (20 μL), and the mixture was stirred at 55° C. for 16 hour. The insoluble material was removed by filtration, and the reaction mixture was concentrated under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=90/10-10/90) to give the title compound (13 mg).

$^1$H-NMR (CD$_3$OD) δ ppm: 1.36 (3H, t, J=7.1 Hz), 1.56-1.90 (4H, m), 3.58 (2H, t, J=6.5 Hz), 3.73-3.90 (2H, m), 3.94-4.16 (5H, m), 4.24 (1H, dd, J=2.3 Hz, 5.7 Hz), 4.43-4.65 (3H, m), 5.94 (1H, d, J=7.6 Hz), 6.80-7.10 (5H, m), 7.20-7.35 (2H, m)

EXAMPLES 35-48

The compounds of Tables 8 to 11 were prepared in a similar manner to that described in Example 34 using the corresponding materials.

TABLE 8

| Example No. | Structure | $^1$H-NMR δ ppm: |
|---|---|---|
| Example 35 | 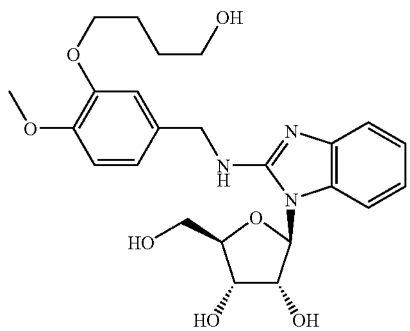 | (CD$_3$OD) 1.56-1.90 (4 H, m), 3.57 (2 H, t, J = 6.5 Hz), 3.70-3.85 (5 H, m), 3.94-4.05 (2 H, m), 4.08-4.15 (1 H, m), 4.24 (1 H, dd, J = 2.3 Hz, 5.7 Hz), 4.45-4.65 (3 H, m), 5.94 (1 H, d, J= 7.8 Hz), 8.80-7.10 (5 H, m), 7.20-7.35 (2 H, m) |

TABLE 9

| Example No. | Structure | $^1$H-NMR δ ppm: |
|---|---|---|
| Example 36 | 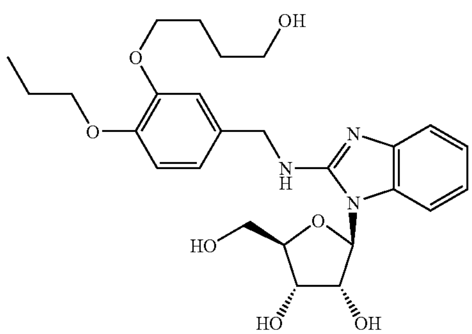 | (CD$_3$OD) 1.02 (3 H, t, J = 7.4 Hz), 1.56-1.90 (6 H, m), 3.58 (2 H, t, J = 6.5 Hz), 3.73-3.85 (2 H, m), 3.91 (2 H, t, J = 6.5 Hz), 3.99 (2 H, t, ,J = 6.5 Hz), 4.05-4.15 (1 H, m), 4.24 (1 H, dd, J = 2.3 Hz, 5.8 Hz), 4.43-4.65 (3 H, m), 5.94 (1 H, d, J = 7.7 Hz), 6.80-7.10 (5 H, m), 7.15-7.35 (2 H, m) |
| Example 37 | 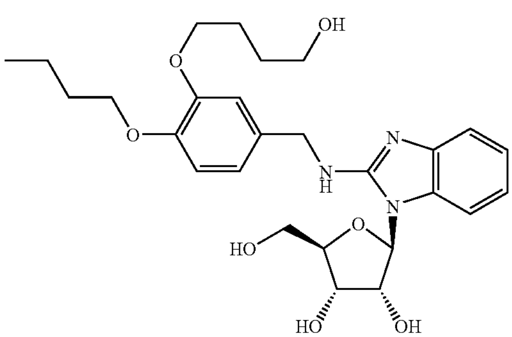 | (CD$_3$OD) 0.97 (3 H, t, J = 7.4 Hz), 1.40-1.55 (2 H, m), 1.60-1.90 (6 H, m), 3.58 (2 H, t, J = 6.6 Hz), 3.55-3.85 (2 H, m), 3.96 (2 H, t, J = 6.5 Hz), 4.00 (2 H, t, J = 6.4 Hz), 4.05-4.15 (1 H, m), 4.25 (1 H, dd, J = 2.4 Hz, 5.9 Hz), 4.45-4.65 (3 H, m), 5.95 (1 H, d, J = 7.5 Hz), 6.80-7.10 (5 H, m), 7.20-7.35 (2 H, m) |
| Example 38 | 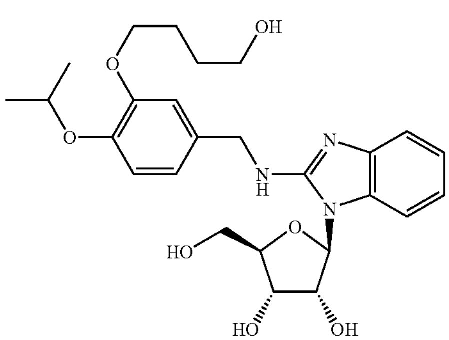 | (CD$_3$OD) 1.26 (6 H, d, J = 7.8 Hz), 1.60-1.90 (4 H, m), 3.58 (2 H, t, J = 6.4 Hz), 3.75-3.85 (2 H, m), 4.00 (2 H, t, J = 6.3 Hz), 4.05-4.15 (1 H, m), 4.25 (1 H, dd, J = 2.3 Hz, 5.7 Hz) , 4.35-4.65 (4 H, m), 5.95 (1 H, d, J = 7.4 Hz), 6.80-7.10 (5 H, m), 7.20-7.35 (2 H, m) |

TABLE 9-continued

| Example No. | Structure | $^1$H-NMR δ ppm: |
|---|---|---|
| Example 39 | 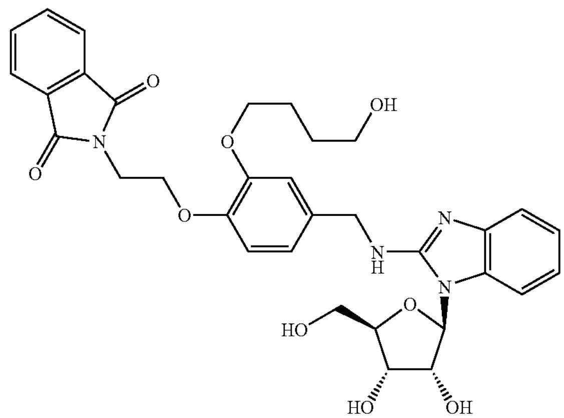 | (CD$_3$OD) 1.45-1.75 (4 H, m), 3.50 (2 H, t, J = 6.5 Hz), 3.70-3.95 (4 H, m), 4.00-4.40 (6 H, m), 4.43-4.65 (3 H, m), 5.94 (1 H, d, J = 7.7 Hz), 6.80-7.10 (5 H, m), 7.15-7.35 (2 H, m), 7.50-7.70 (4 H, m) |
| Example 40 | 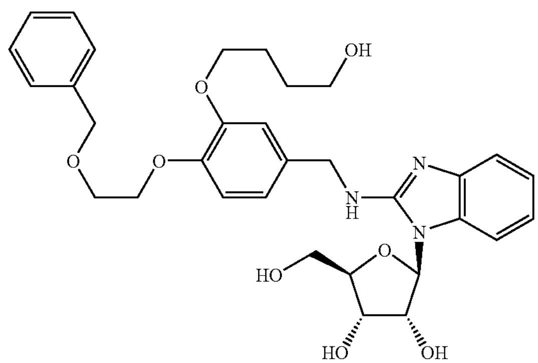 | (CD$_3$OD) 1.55-1.90 (4 H, m), 3.55 (2 H, t, J = 6.4 Hz), 3.70-3.90 (4 H, m), 4.01 (2 H, t, J = 6.4 Hz), 4.05-4.20 (3 H, m), 4.24 (1 H, dd, J = 2.3 Hz, 5.9 Hz), 4.40-4.70 (5 H, m), 5.94 (1 H, d, J = 7.4 Hz), 6.80-7.10 (5 H, m), 7.15-7.45 (7 H, m) |
| Example 41 | 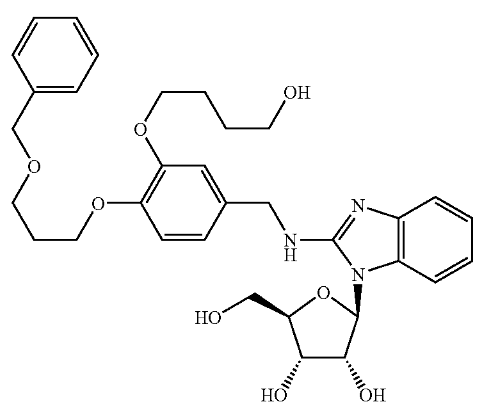 | (CD$_3$OD) 1.55-1.85 (4 H, m), 1.90-2.10 (2 H, m), 3.56 (2 H, t, J = 6.5 Hz), 3.67 (2 H, t, J = 6.2 Hz), 3.72-3.88 (2 H, m), 3.92 (2 H, t, J = 6.4 Hz), 4.07 (2 H, t, J = 6.1 Hz), 4.09-4.15 (1 H, m), 4.24 (1 H, dd, J = 2.4 Hz, 5.9 Hz), 4.40-4.70 (5 H, m), 5.95 (1 H, d, J = 7.5 Hz), 6.80-7.10 (5 H, m), 7.15-7.45 (7 H, m) |

TABLE 10

| Example No. | Structure | $^1$H-NMR δ ppm: |
|---|---|---|
| Example 42 | 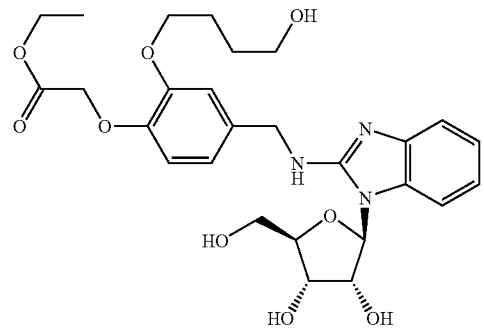 | (CD$_3$OD) 1.25 (3 H, t, J = 7.0 Hz), 1.55-1.90 (4 H, m), 3.58 (2 H, t, J = 6.4 Hz), 3.73-3.85 (2 H, m), 4.03 (2 H, t, J = 6.4 Hz), 4.05-4.15 (1 H, m), 4.21 (2 H, q, J = 7.0 Hz), 4.25 (1 H, dd, J = 2.4 Hz, 5.9 Hz), 4.43-4.70 (5 H, m), 5.96 (1 H, d, J = 7.3 Hz), 6.80-7.15 (5 H, m), 7.20-7.40 (2 H, m) |
| Example 43 | 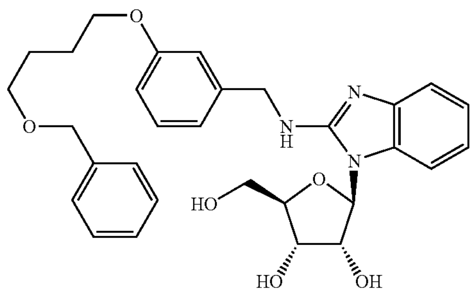 | (CD$_3$OD) 1.65-1.90 (4 H, m), 3.49 (2 H, t, J = 6.3 Hz), 3.73-3.88 (2 H, m), 3.94 (2 H, t, J = 6.3 Hz), 4.05-4.17 (1 H, m) 1 4.25 (1 H, dd, J = 2.2 Hz, 5.7 Hz), 4.45 (2 H, s), 4.50-4.70 (3 H, m), 5.95 (1 H, d, J = 7.0 Hz), 6.73 (1 H, dd, J = 1.7 Hz, 8.9 Hz), 6.90-7.08 (4 H, m), 7.13-7.38 (8 H, m) |
| Example 44 | 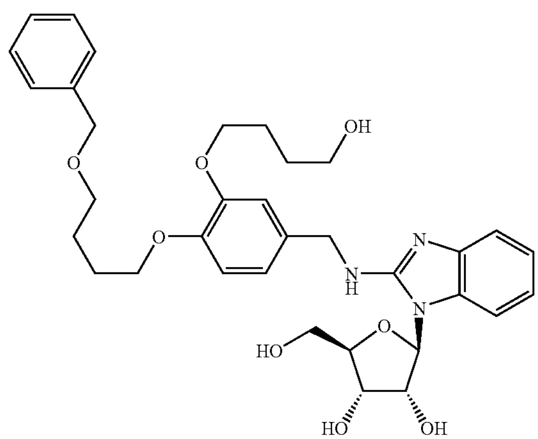 | (CD$_3$OD) 1.60-1.90 (8 H, m), 3.50-3.65 (4 H, m), 3.75-3.85 (2 H, m), 3.93-4.15 (5 H, m), 4.24 (1 H, dd, J = 2.4 Hz, 5.8 Hz), 4.45-4.85 (5 H, m), 5.94 (1 H, d, J = 7.7 Hz), 6.80-7.10 (5 H, m), 7.19-7.50 (7 H, m) |
| Example 45 | 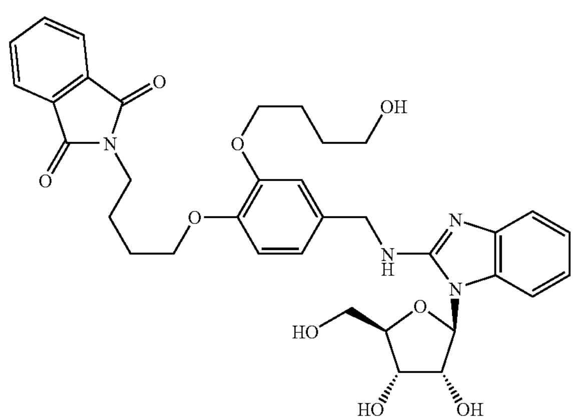 | (DMSO-d$_6$) 1.44-1.58 (2 H, m), 1.62-1.83 (6 H, m), 3.30-3.45 (2 H, m), 3.57-3.75 (4 H, m), 3.85-4.00 (5 H, m), 4.05-4.15 (1 H, m), 4.30-4.55 (4 H, m), 5.18 (1 H, d, J = 3.9 Hz), 5.26 (1 H, d, J = 7.2 Hz), 5.56 (1 H, t, J = 4.3 Hz), 5.79 (1 H, d, J = 7.4 Hz), 6.75-7.01 (5 H, m), 7.16 (1 H, d, J = 7.5 Hz), 7.26 (1 H, d, J = 7.5 Hz), 7.33 (1 H, t, J = 6.0 Hz), 7.75-7.95 (4 H, m) |

TABLE 10-continued

| Example No. | Structure | $^1$H-NMR δ ppm: |
|---|---|---|
| Example 46 | 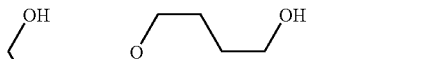 | (DMSO-d$_6$) 1.35-1.80 (10 H, m), 3.30-3.50 (4 H, m), 3.60-3.76 (2 H, m), 3.85-4.02 (5 H, m), 4.05-4.15 (1 H, m), 4.30-4.55 (5 H, m), 5.19 (1 H, d, J = 3.9 Hz), 5.26 (1 H, d, J = 7.2 Hz), 5.56 (1 H, t, J = 4.3 Hz), 5.79 (1 H, d, J = 7.6 Hz), 6.80-7.05 (5 H, m), 7.16 (1 H, d, J = 7.9 Hz), 7.26 (1 H, d, J = 7.9 Hz), 7.34 (1 H, t, J = 6.1 Hz) |

TABLE 11

| Example No. | Structure | $^1$H-NMR δ ppm: |
|---|---|---|
| Example 47 | 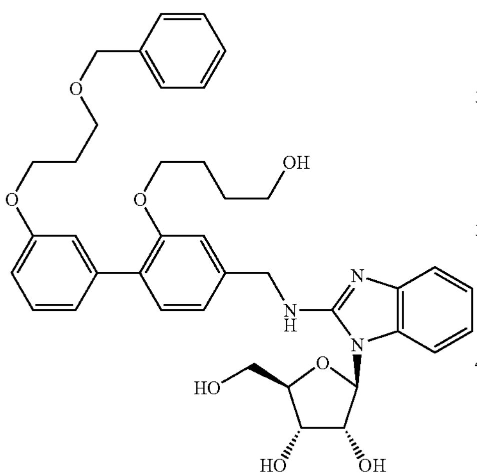 | (DMSO-d$_6$) 1.40-1.55 (2 H, m), 1.60-1.75 (2 H, m), 1.90-2.05 (2 H, m), 3.30-3.45 (2 H, m), 3.53-3.63 (2 H m), 3.65-3.80 (2 H, m), 3.90-4.20 (6 H, m), 4.37 (1 H, t, J = 5.1 Hz), 4.40-4.52 (3 H, m), 4.59 (2 H, d, J = 6.0 Hz), 5.22 (1 H, d, J = 3.9 Hz), 5.30 (1 H, d, J = 7.4 Hz), 5.63 (1 H, t, J = 4.0 Hz), 5.83 (1 H, d, J = 7.6 Hz), 6.80-7.40 (16 H, m), 7.49 (1 H, t, J = 6.0 Hz) |
| Example 48 | 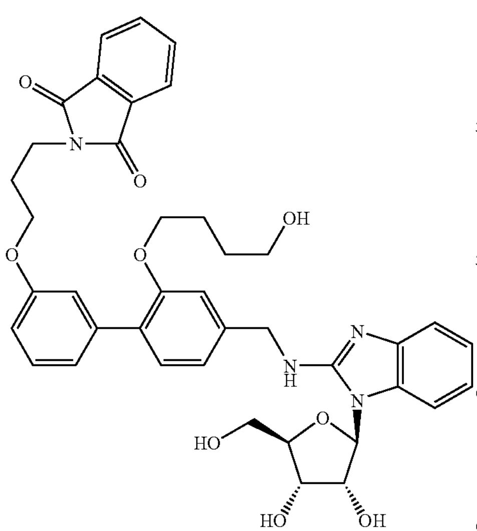 | (DMSO-d$_6$) 1.40-1.53 (2 H, m), 1.58-1.73 (2 H, m), 1.98-2.12 (2 H, m), 3.30-3.43 (2 H, m), 3.63-3.82 (4H, m), 3.88-4.18 (6 H, m), 4.36 (1 H, t, J = 5.1 Hz), 4.40-4.50 (1 H, m), 4.59 (2 H, d, J = 6.1 Hz), 5.22(1 H, d, J = 3.9 Hz), 5.31 (1 H, d, J = 7.4 Hz), 5.63 (1 H, t, J = 4.0 Hz), 5.83 (1 H, d, J = 7.4 Hz), 6.71 (1 H, dd, J = 1.7 Hz, 8.0 Hz), 6.80-7.35 (10 H, m), 7.49 (1 H, t, J = 6.1 Hz), 7.70-7.90 (4 H, m) |

EXAMPLE 49

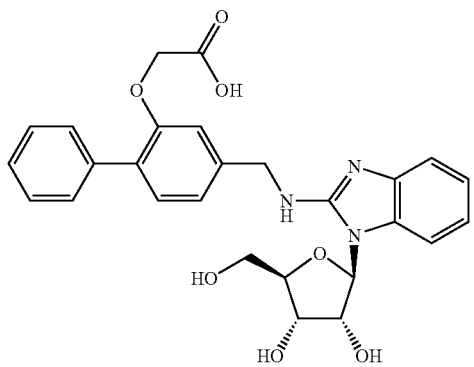

2-(3-Carboxymethyloxy-4-phenylbenzylamino)-1-
(β-D-ribofuranosyl)-1H-benzimidazole 2-(3-Ethoxycarbonylmethyloxy-4-phenylbenzylamino)-1-(β-D-ribofuranosyl)-1H-benzimidazole (53 mg) was dissolved in tetrahydrofuran (5 mL). To the reaction mixture was added 2 mol/L aqueous sodium hydroxide solution (1 mL), and the mixture was stirred 60° C. for 1 hour. To the reaction mixture was added 2 mol/L hydrochloric acid (1 mL), and the solvent was removed under reduced pressure. The obtained residue was purified by preparative reverse phase column chromatography (Shiseido CAPSELL PAC C18UG80, 5 µm, 20×50 mm, flow rate 30 mL/minutes linear gradient, water/methanol=70/30-10/90) to give the title compound (20 mg).
$^1$H-NMR (DMSO-$d_6$) δ ppm: 3.60-3.80 (2H, m), 3.96-4.04 (1H, m), 4.08-4.16 (1H, m), 4.35-4.50 (1H, m), 4.58 (2H, d, J=6.0 Hz), 4.66 (2H, s), 5.83 (1H, d, J=7.6 Hz), 6.89 (1H, t, J=7.6 Hz), 6.95 (1H, t, J=7.6 Hz), 7.00-7.60 (11H, m)

EXAMPLE 50

The compound of Table 12 was prepared in a similar manner to that described in Example 49 using the corresponding materials.

EXAMPLE 51

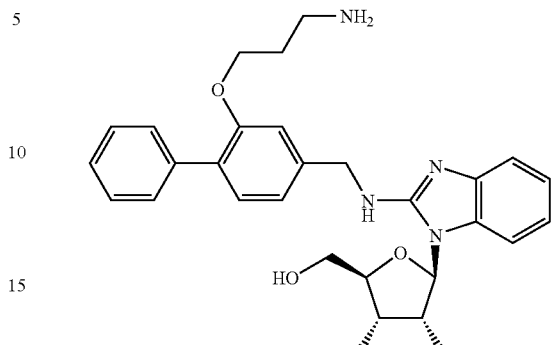

2-[3-(3-Aminopropoxy)-4-phenylbenzylamino]-1-
(β-D-ribofuranosyl)-1H-benzimidazole 2-[3-(3-Phthalimidepropoxy)-4-phenylbenzylamino]-1-(β-D-ribofuranosyl)-1H-benzimidazole (53 mg) was dissolved in methanol (5 mL). To the mixture was added hydrazine monohydrate (0.5 mL), and the mixture was stirred at 90° C. for 6 hours. The solvent was removed under reduced pressure, and the obtained residue was purified by preparative reverse phase column chromatography (Shiseido CAPSELL PAC C18UG80, 5 µm, 20×50 mm, flow rate 30 mL/minutes linear gradient, water/methanol=70/30-10/90) to give the title compound (22 mg).
$^1$H-NMR (DMSO-$d_6$) δ ppm: 1.60-1.88 (2H, m), 2.50-2.70 (2H, m), 3.60-3.80 (2H, m), 3.95-4.20 (4H, m), 4.40-4.50 (1H, m), 4.55-4.65 (2H, m), 5.84 (1H, d, J=7.5 Hz), 6.88 (1H, t, J=7.6 Hz), 6.95 (1H, t, J=7.6 Hz), 7.01 (1H, d, J=7.6 Hz), 7.10-7.60 (10H, m)

EXAMPLES 52-53

The compounds of Table 13 were prepared in a similar manner to that described in Example 51 using the corresponding materials.

TABLE 12

| Example No. | Structure | $^1$H-NMR δ ppm: |
|---|---|---|
| Example 50 | 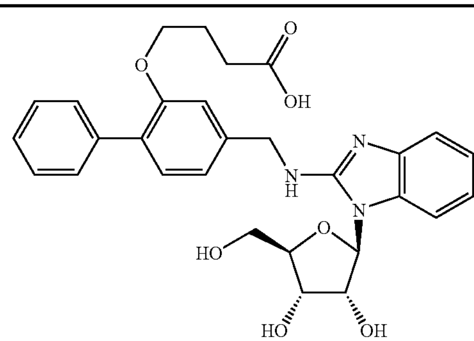 | (DMDO-$d_6$) 1.75-1.95 (2 H, m), 2.20-2.40 (2 H, m), 3.60-3.80 (2 H, m), 3.90-4.20 (4 H, m), 4.35-4.50 (1 H, m), 4.58 (2 H, d, J = 7.0 Hz), 5.83 (1 H, d, J = 7.5 Hz), 6.89 (1 H, t, J = 7.6 Hz), 6.95 (1 H, t, J = 7.6 Hz), 7.02 (1 H, d, J = 7.6 Hz), 7.12 (1 H, s), 7.17 (1 H, d, J = 7.6 Hz), 7.22 (1 H, d, J = 7.6 Hz), 7.26-7.58 (7 H, m), 11.70-12.40 (1 H, m) |

TABLE 13

| Example No. | Structure | ¹H-NMR δ ppm: |
|---|---|---|
| Example 52 | 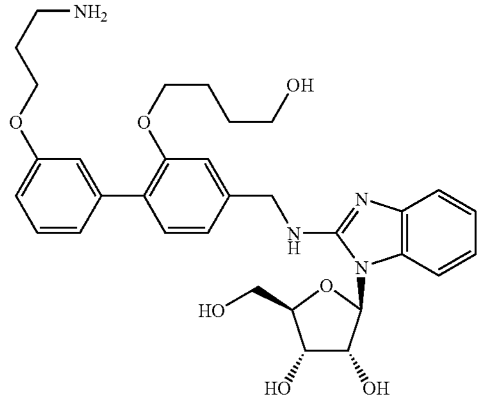 | (DMSO-$d_6$) 1.40-1.55 (2 H, m), 1.60-1.83 (4 H, m), 2.68 (2 H, t, J = 6.5 Hz), 3.38 (2 H, t, J = 6.5 Hz), 3.60-3.80 (2 H, m), 3.90-4.06 (5 H, m), 4.08-4.16 (1 H, m), 4.38-4.49 (1 H, m), 4.59 (2 H, d, J = 6.0 Hz), 5.22 (1 H, d, J = 3.9 Hz), 5.30 (1 H, d, J = 7.4 Hz), 5.63 (1 H, t, J = 4.0Hz), 5.83 (1 H, d, J = 7.5 Hz), 6.80-7.32 (11 H, m), 7.49 (1 H, t, J = 6.0 Hz) |
| Example 53 | 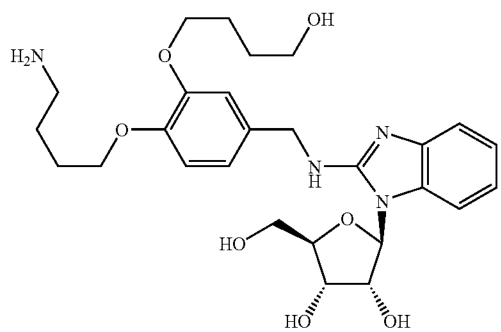 | (DMSO-$d_6$) 1.40-1.80 (8 H, m), 2.57 (2 H, t, 3.85-4.02 (5 H, m), 4.05-4.15 (1 H, m), 4.35-4.45 J = 6.5 Hz), 3.44 (2 H, t, J = 6.5 Hz), 3.60-3.75 (2 H, m), (1 H, m), 4.47 (2 H, d, J = 5.9 Hz), 5.19 (1 H, d, J = 4.3 Hz), 5.79 (1 H, d, J = 7.2 Hz), 6.80-7.05 (5 H, m), 7.16 (1 H, d, J = 7.9 Hz), 7.27 (1 H, d, J = 7.9 Hz), 7.34 (1 H, t, J = 5.9 Hz) |

EXAMPLE 54

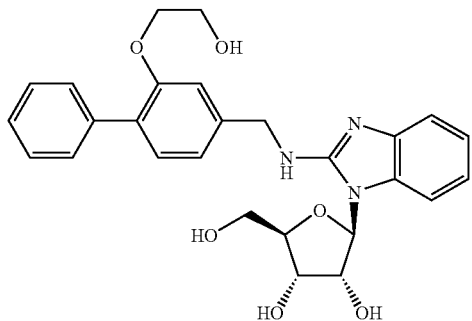

2-[3-(2-Hydroxyethyloxy)-4-phenylbenzylamino]-1-(β-D-ribofuranosyl)-1H-benzimidazole 2-(3-Ethoxycarbonylmethyloxy-4-phenylbenzylamino)-1-(β-D-ribofuranosyl)-1H-benzimidazole (53 mg) was dissolved in methanol (5 mL). To the mixture was added sodium tetrahydroborate (8 mg), and the mixture was stirred at room temperature for 1 hours. To the reaction mixture was added 1 mol/L hydrochloric acid (0.5 mL), and the solvent was removed under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (21 mg).

¹H-NMR (DMSO-$d_6$) δ ppm: 3.60-3.80 (4H, m), 3.93-4.20 (4H, m), 4.38-4.50 (1H, m), 4.59 (2H, d, J=5.8 Hz), 4.73 (1H, t, J=5.2 Hz), 5.21 (1H, d, J=4.4 Hz), 5.29 (1H, d, J=7.2 Hz), 5.63 (1H, t, J=3.8 Hz), 5.83 (1H, d, J=7.2 Hz), 6.89 (1H, t, J=7.6 Hz), 6.95 (1H, t, J=7.6 Hz), 7.02 (1H, d, J=7.6 Hz), 7.13 (1H, s), 7.18 (1H, d, J=7.6 Hz), 7.23 (1H, d, J=7.6 Hz), 7.25-7.60 (7H, m)

EXAMPLE 55

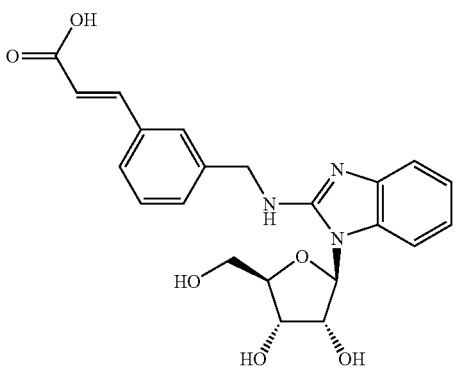

2-[3-(2-Carboxyvinyl)benzylamino]-1-(β-D-ribofuranosyl)-1H-benzimidazole 2-(3-Bromobenzylamino)-1-(β-D-ribofuranosyl)-1H-benzimidazole (200 mg), acrylic acid (112 mg), palladium acetate (10 mg) and tri-o-tolylphosphine (28 mg) were suspended in acetonitrile (2 mL). To the mixture was added triethylamine (0.3 mL), and the mixture was stirred at 100° C. for 10 hours. The insoluble material was removed by filtration, and the solvent was removed under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (52 mg).

$^1$H-NMR (CD$_3$OD) δ ppm: 3.75-3.90 (2H, m), 4.10-4.20 (1H, m), 4.26 (1H, dd, J=2.2 Hz, 5.7 Hz), 4.60 (1H, dd, J=5.7 Hz, 7.5 Hz), 4.64 (1H, d, J=15.9 Hz), 4.69 (1H, d, J=15.9 Hz), 5.99 (1H, d, J=7.5 Hz), 6.48 (1H, d, J=16.0 Hz), 6.99-7.12 (2H, m), 7.20-7.52 (5H, m), 7.60 (1H, d, J=16.0 Hz), 7.62 (1H, s)

EXAMPLE 56

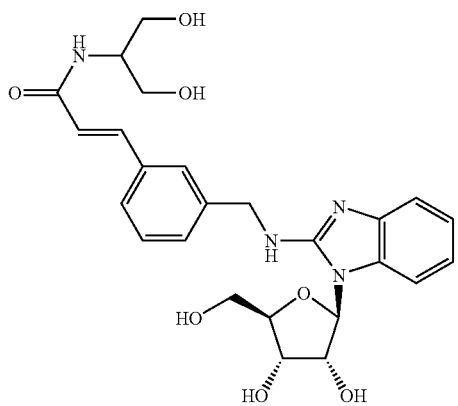

2-{3-[2-(2-Hydroxy-1-hydroxymethyethylcarbamoyl)vinyl]-benzylamino}-1-(β-D-ribofuranosyl)-1H-benzimidazole 2-[3-(2-Carboxyvinyl)benzylamino]-1-(β-D-ribofuranosyl)-1H-benzimidazole (50 mg), 2-amino-1,3-propanediol (21 mg), 1-hydroxybenzotriazole (36 mg) and triethylamine (41 μL) were suspended in tetrahydrofuran (2 mL). To the mixture was added 1-ethyl-3-(3-dimethylaminopropyl)carbodiimide hydrochloride (45 mg), and the mixture was stirred for 17 hours. The solvent was removed under reduced pressure, and the obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (52 mg)

$^1$H-NMR (CD$_3$OD) δ ppm: 3.66 (4H, d, J=5.4 Hz), 3.75-3.90 (2H, m), 3.99-4.16 (2H, m), 4.27 (1H, dd, J=2.6 Hz, 5.8 Hz), 4.60 (1H, dd, J=5.8 Hz, 7.4 Hz), 4.63 (1H, d, J=15.9 Hz), 4.69 (1H, d, J=15.9 Hz), 5.97 (1H, d, J=7.4 Hz), 6.65 (1H, d, J=15.7 Hz), 6.95-7.10 (2H, m), 7.20-7.47 (5H, m), 7.52 (1H, d, J=15.7 Hz), 7.59 (1H, s)

EXAMPLE 57

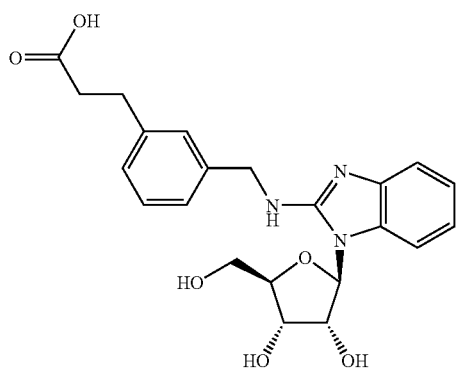

2-[3-(2-Carboxyethyl)benzylamino]-1-(β-D-ribofuranosyl)-1H-benzimidazole

2-[3-(2-Carboxyvinyl)benzylamino]-1-(β-D-ribofuranosyl)-1H-benzimidazole (30 mg) was dissolved in methanol (2 mL). To the solution was added a catalytic amount of 10% palladium-carbon powder, and the mixture was stirred at room temperature under a hydrogen atmosphere for 1 hour. The insoluble material was removed by filtration, and the solvent of the filtrate was removed under reduced pressure to give the title compound (25 mg).

$^1$H-NMR (CD$_3$OD) δ ppm: 2.54 (2H, t, J=7.6 Hz), 2.89 (2H, t, J=7.6 Hz), 3.70-3.90 (2H, m), 4.05-4.18 (1H, m), 4.25 (1H, dd, J=2.3 Hz, 5.7 Hz), 4.50-4.75 (3H, m), 5.97 (1H, d, J=7.3 Hz), 7.00-7.15 (3H, m), 7.16-7.40 (5H, m)

EXAMPLE 58

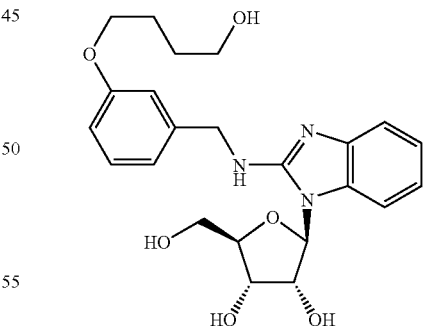

2-[3-(4-Hydroxybutyloxy)benzylamino]-1-(β-D-ribofuranosyl)-1H-benzimidazole

2-[3-(4-Benzyloxybutyloxy)benzylamino]-1-(β-D-ribofuranosyl)-1H-benzimidazole (24 mg) was dissolved in ethanol (2 mL). To the solution was added a catalytic amount of 10% palladium-carbon powder, and the mixture was stirred at 60° C. under a hydrogen atmosphere for 24 hour. The insoluble material was removed by filtration, and the solvent of the filtrate was removed under reduced pressure to give the title compound (20 mg).

$^1$H-NMR (CD$_3$OD) δ ppm: 1.60-1.90 (4H, m), 3.57 (2H, t, J=6.6 Hz), 3.75-3.90 (2H, m), 3.96 (2H, t, J=6.4 Hz), 4.05-4.10 (1H, m), 4.25 (1H, dd, J=2.6 Hz, 5.7 Hz), 4.50-4.70 (3H, m), 5.95 (1H, d, J=7.3 Hz), 6.75 (1H, dd, J=1.6 Hz, 8.3 Hz), 6.90-7.08 (4H, m), 7.13-7.35 (3H, m)

EXAMPLES 59-62

The compounds of Table 14 were prepared in a similar manner to that described in Example 58 using the corresponding materials.

TABLE 14

| Example No. | Structure | $^1$H-NMR δ ppm: |
|---|---|---|
| Example 59 | 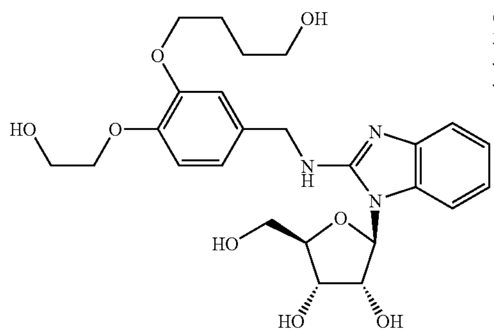 | (CD$_3$OD) 1.55-1.90 (4 H, m), 3.58 (2 H, t, J = 6.4 Hz), 3.74-3.90 (4 H, m), 3.95-4.18 (5 H, m), 4.24(1 H, dd, J = 2.3 Hz, 5.7 Hz), 4.45-4.70 (3 H, m), 5.95 (1 H, d, J = 7.7 Hz), 6.85-7.15 (5 H, m), 7.20-7.25 (2 H, m) |
| Example 60 | 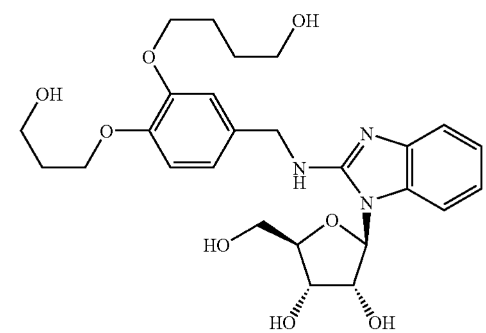 | (CD$_3$OD) 1.55-2.10 (6 H, m), 3.58 (2 H, t, J = 6.5 Hz), 3.60-3.90 (4 H, m), 3.95-4.20 (5 H, m), 4.24 (1 H, dd, J = 2.1 Hz, 5.7 Hz), 4.45-4.65 (3 H, m), 5.95 (1 H, d, J = 4.4 Hz), 6.80-7.15 (5 H, m), 7.20-7.35 (2 H, m) |
| Example 61 | 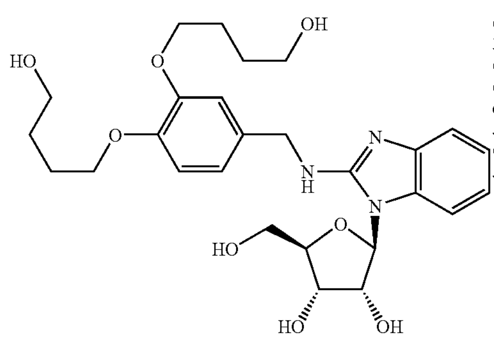 | (DMSO-d$_6$) 1.48-1.60 (4 H, m), 1.65-1.80 (4 H, m), 3.35-3.50 (4 H, m), 3.60-3.75 (2 H, m), 3.85-4.00 (5 H, m), 4.05-4.15 (1 H, m), 4.35-4.44 (3 H, m), 4.47 (2 H, d, J = 6.0 Hz), 5.19 (1 H, d, J = 3.9 Hz), 5.27 (1 H, d, J = 7.2 Hz), 5.57 (1 H, t, J = 4.3 Hz), 5.79 (1 H, d, J = 7.4 Hz), 6.82-6.90 (3 H, m), 6.95 (1 H, t, J = 7.6 Hz), 6.99 (1 H, s), 7.17 (1 H, d, J = 7.6 Hz), 7.27 (1 H, d, J = 7.6 Hz), 7.34 (1 H, t, J = 6.0 Hz) |

TABLE 14-continued

| Example No. | Structure | $^1$H-NMR δ ppm: |
|---|---|---|
| Example 62 | 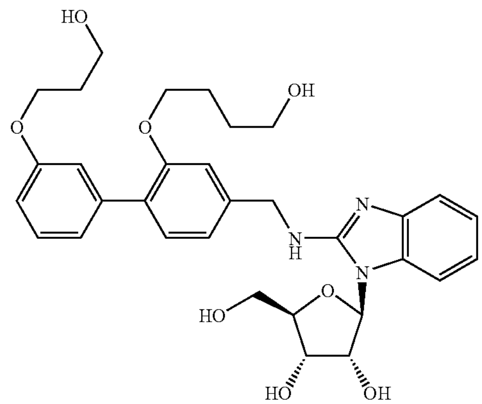 | (DMSO-$d_6$) 1.40-1.55 (2 H, m), 1.60-1.75 (2 H, m), 1.80-1.90 (2 H, m), 3.33-3.44 (2 H, m), 3.49-3.60 (2 H, m), 3.64-3.80 (2 H, m), 3.90-4.20 (6 H, m), 4.35-4.55 (3 H, m), 4.59 (2 H, d, J = 6.2 Hz), 5.22 (1 H, d, J = 3.9 Hz), 5.31 (1 H, d, J = 7.4 Hz), 5.63 (1 H, t, J = 4.0 Hz), 5.83 (1 H, d, J = 7.5 Hz), 6.78-7.35 (11 H, m), 7.49 (1 H, t, J = 6.2 Hz) |

EXAMPLE 63

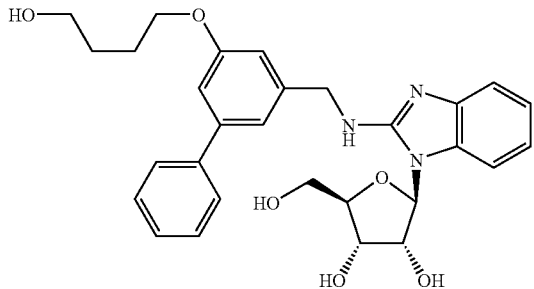

2-[3-(4-Hydroxybutoxy)-5-phenylbenzylamino]-1-(β-D-ribofuranosyl)-1H-benzimidazole 2-Amino-1-(2,3,5-tri-O-acetyl-β-D-ribofuranosyl)-1H-benzimidazole (0.20 g) and 3-(4-acetoxybutoxy)-5-phenyl-benzaldehyde (0.19 g) were suspended in tetrahydrofuran (3 mL), and the mixture was stirred at room temperature for 13 hours. To the reaction mixture was added sodium triacetoxyborohydride (0.21 g), and the mixture was stirred at room temperature for 24 hours. After adding water to the reaction mixture, the mixture was concentrated under reduced pressure. The obtained residue was dissolved in methanol (2 mL). To the reaction mixture was added 5 mol/L aqueous sodium hydroxide solution (0.5 mL), and the mixture was stirred at room temperature for 1 hour. To the reaction mixture was added acetic acid (1 mL), and the mixture was concentrated under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (0.08 g).
$^1$H-NMR (DMSO-$d_6$) δ ppm: 1.45-1.85 (4H, m), 3.60-3.78 (2H, m), 3.93-4.15 (4H, m), 4.34-4.45 (1H, m), 4.50-4.65 (2H, m), 5.87 (1H, d, J=7.6 Hz), 6.80-7.05 (4H, m), 7.10-7.50 (6H, m), 7.55-7.70 (3H, m)

EXAMPLES 64-70

The compounds of Table 15 were prepared in a similar manner to that described in Example 63 using the corresponding materials.

TABLE 15

| Example No. | Structure | $^1$H-NMR δ ppm |
|---|---|---|
| Example 64 | 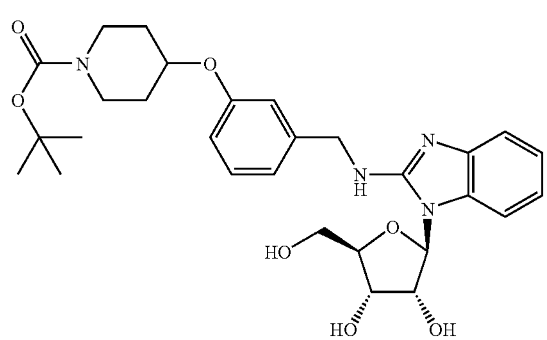 | (DMSO-$d_6$) 1.30-1.55 (11 H, m), 1.78-1.95 (2 H, m), 3.00-3.20 (2 H, m), 3.55-3.80 (4 H, m), 3.95-4.04 (1 H, m), 4.08-4.16 (1 H, m), 4.35-4.62 (4 H, m), 5.82 (1 H, d, J = 7.7 Hz), 6.75-7.02 (5 H, m), 7.10-7.55 (4 H, m) |

TABLE 15-continued

| Example No. | Structure | $^1$H-NMR δ ppm |
|---|---|---|
| Example 65 | 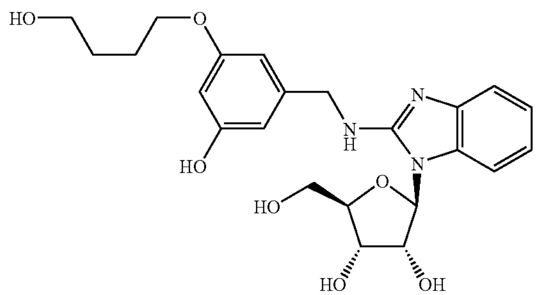 | (DMSO-$d_6$) 1.45-1.58 (2 H, m), 1.62-1.75 (2 H, m), 3.60-3.75 (2 H, m), 3.86 (2 H, t, J = 6.6 Hz), 3.95-4.03 (1 H. m) . 4.06-4.16 (1 H, m), 4.35-4.55 (3 H, m), 5.20-5.40 (2 H, m), 5.61 (1 H, t, J = 4.0 Hz), 5.81 (1 H, d, J = 7.5 Hz), 6.15 (1 H, s), 6.35 (2 H, s), 6.87 (1 H, t, J = 7.6 Hz), 6.95 (1 H, t, J = 7.6 Hz), 7.16 (1 H, d, J = 7.6 Hz), 7.28 (1 H, d J = 7.6 Hz), 7.41 (1 H, t, J =0 6.1 Hz), 9.32 (1 H, s) |
| Example 66 | 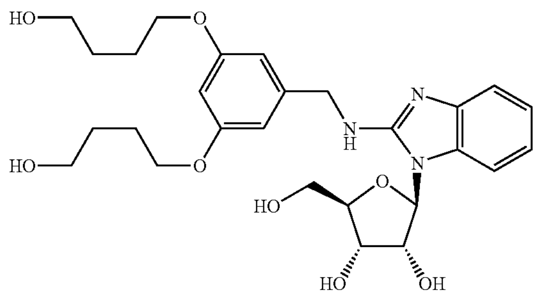 | (DMSO-$d_6$) 1.45-1.60 (4 H, m), 1.62-1.80 (4 H, m), 3.35-3.50 (4 H, m), 3.60-3.78 (4 H, m), 3.85-4.04 (5 H, m), 4.06-4.15 (1 H, m), 4.35-4.55 (5 H, m), 5.27 (1 H, d, J = 4.0 Hz), 5.34 (1 H, d, J = 7.1 Hz), 5.62 (1 H, t, J = 4.1 Hz), 5.81 (1 H, d, J = 7.5 Hz), 6.31 (1 H, t, J = 2.2 Hz), 6.86 (1 H, d, J = 2.2 Hz), 6.88 (1 H, d, J = 7.6 Hz), 6.95 (1 H, t, J = 7.6 Hz), 7.16 (1 H, d, J = 7.6 Hz), 7.28 (1 H, d, J = 7.6 Hz), 7.43 (1 H, t, J = 6.2 Hz) |
| Example 67 | 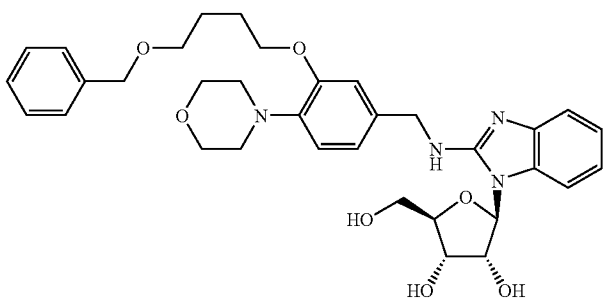 | (DMSO-$d_6$) 1.65-1.85 (4 H, m), 2.84-3.00 (4 H, m), 3.40-3.55 (2 H, m), 3.60-3.80 (6 H, m), 3.90-4.15 (4 H, m), 4.35-4.60 (5 H, m), 5.80 (2 H, d, J = 6.3 Hz), 6.75-7.05 (5 H, m), 7.10-7.50 (8 H, m) |
| Example 68 | 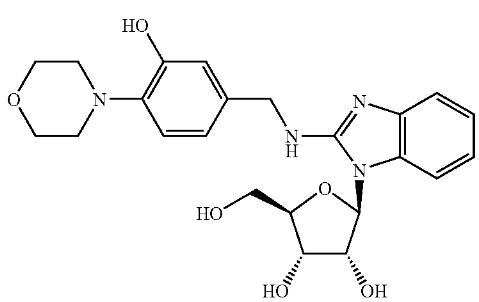 | (DMSO-$d_6$) 2.80-2.95 (4 H, m), 3.60-3.80 (6 H, m), 3.93-4.03 (1 H, m), 4.05-4.13 (1 H, m), 4.30-4.55 (3 H, m), 5.79 (1 H, d, J = 7.5 Hz), 6.70-7.00 (5 H, m), 7.16 (1 H, d, J = 7.8 Hz), 7.28 (1 H, d, J = 7.8 Hz), 7.36 (1 H, t, J = 6.1 Hz), 8.94 (1 H, s) |
| Example 69 | 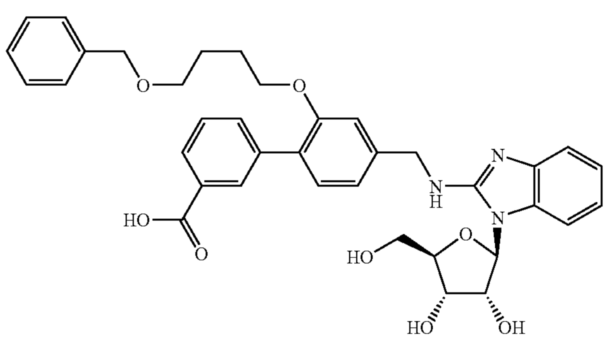 | (DMSO-$d_6$) 1.50-1.80 (4 H, m), 3.65-3.78 (2 H, m), 3.90-4.05 (3 H, m), 4.10-4.18 (1 H, m), 4.37 (2 H, s), 4.40-4.50 (1 H, m), 4.40-4.50 (1 H, m), 4.61 (2 H, d, J = 6.1 Hz), 5.84 (1 H, d, J = 7.5 Hz), 6.80-7.40 (12 H, m), 7.43-7.55 (2 H, m), 7.63-7.74 (1 H, m), 7.80-7.90 (1 H, m), 8.09 (1 H, s) |

TABLE 15-continued

| Example No. | Structure | $^1$H-NMR δ ppm |
|---|---|---|
| Example 70 | 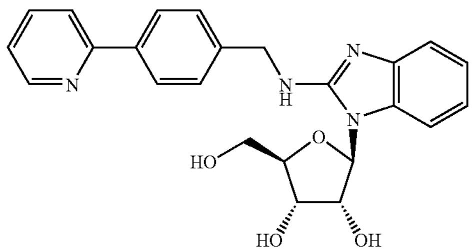 | (CD$_3$OD) 3.75-3.90 (2 H, m), 4.05-4.30 (2 H, m), 4.55-4.80 (3 H, m), 5.97 (1 H, d, J = 7.3 Hz), 6.90-7.10 (2 H, m), 7.20-7.40 (3 H, m), 7.45-7.60 (2 H, m), 7.75-8.00 (4 H, m), 8.50-8.65 (1 H, m) |

EXAMPLE 71

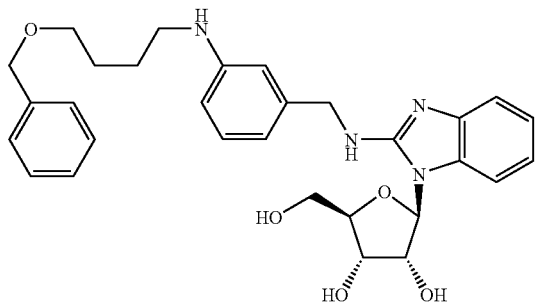

2-[3-(4-Benzyloxybutylamino)benzylamino]-1-(β-D-ribofuranosyl)-1H-benzimidazole

2-Chloro-1-(β-D-ribofuranosyl)-1H-benzimidazole (0.14 g) and 3-(4-benzyloxybutylamino)benzylamine (0.36 g) were suspended in isobutanol (5 mL). To the mixture was added triethylamine (0.56 mL), and the mixture was refluxed for 16 hours. The reaction mixture was concentrated under reduced pressure, and the obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (0.08 g).

$^1$H-NMR (DMSO-d$_6$) δ ppm: 1.50-1.70 (4H, m), 2.90-3.05 (2H, m), 3.43 (2H, t, J=6.1 Hz), 3.60-3.75 (2H, m), 3.95-4.02 (1H, m), 4.05-4.15 (1H, m), 4.35-4.55 (5H, m), 5.21 (1H, d, J=4.1 Hz), 5.27 (1H, d, J=7.5 Hz), 5.40-5.53 (1H, m), 5.57 (1H, t, J=4.4 Hz), 5.80 (1H, d, J=7.5 Hz), 6.38 (1H, d, J=7.7 Hz), 6.45-6.60 (2H, m), 6.80-7.02 (3H, m), 7.15 (1H, d, J=7.5 Hz), 7.20-7.40 (7H, m)

EXAMPLES 72-75

The compounds of Table 16 were prepared in a similar manner to that described in Example 71 using the corresponding materials.

TABLE 16

| Example No. | Structure | $^1$H-NMR δ ppm |
|---|---|---|
| Example 72 | 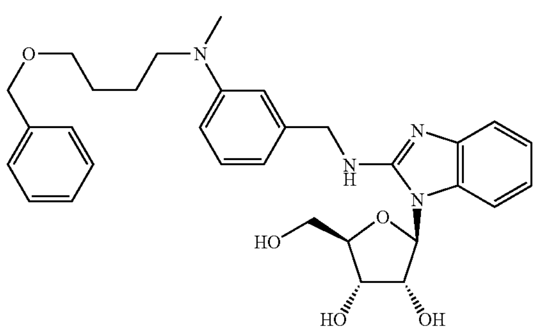 | (DMSO-d$_6$) 1.40-1.60 (4 H, m), 2.83 (3 H, s), 3.60-3.80 (2 H, m), 3.90-4.00 (1 H, m), 4.05-4.20 (1 H, m), 4.35-4.60 (5 H, m), 5.80 (1 H, d, J = 7.6 Hz), 6.45-6.75 (3 H, m), 6.80-7.50 (11 H, m) |

TABLE 16-continued

| Example No. | Structure | ¹H-NMR δ ppm |
|---|---|---|
| Example 73 | 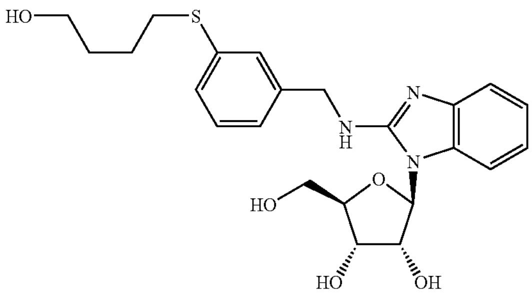 | (DMSO-d₆) 1.40-1.65 (4 H, m), 2.93 (2 H, t, J = 7.2 Hz), 3.30-3.43 (2 H, m), 3.60-3.77 (2 H, m), 3.95-4.03 (1 H, m), 4.08-4.15 (1 H, m), 4.35-4.47 (2 H, m), 4.54 (2 H, d, J = 6.2 Hz), 5.19 (1 H, d, J = 4.4 Hz), 5.28 (1 H, d, J = 7.5 Hz), 5.60 (1 H, t, J = 4.5 Hz), 5.81 (1 H, d, J = 7.4 Hz), 6.88 (1 H, d, J = 7.6 Hz), 6.95 (1 H, d, J = 7.6 Hz), 7.10-7.35 (6 H, m), 7.47 (1 H, t, J = 6.2 Hz) |
| Example 74 | 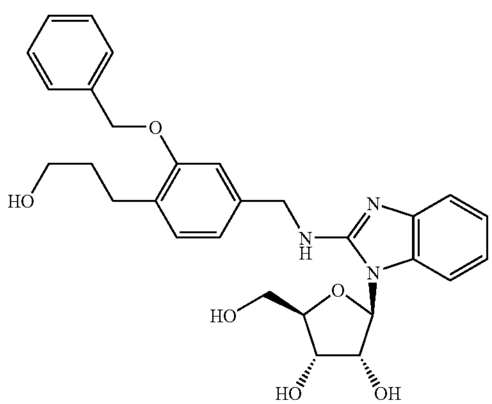 | (DMSO-d₆) 1.58-1.73 (2 H, m), 2.48-2.63 (2 H, m), 3.25-3.45 (2 H, m), 3.60-3.75 (2 H, m), 3.95-4.15 (2 H, m), 4.35-4.60 (4 H, m), 5.07 (2 H, s), 5.15-5.40 (2 H, m), 5.55-5.70 (1 H, m), 5.83 (1 H, d, J = 7.0 Hz), 6.80-7.50 (10 H, m) |
| Example 75 | 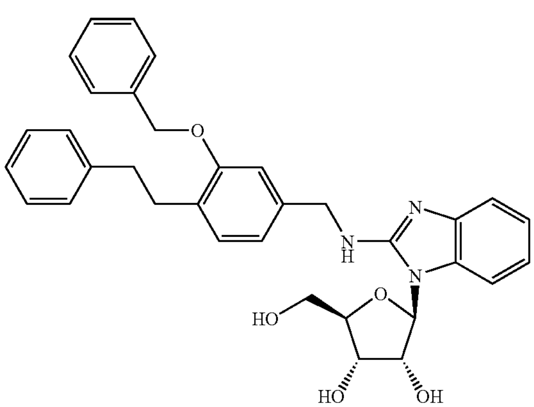 | (DMSO-d₆) 2.82 (2 H, t, J = 7.7 Hz), 3.40-3.75 (4 H, m), 3.90-4.00 (1 H, m), 4.03-4.14 (1 H, m), 4.30-4.45 (1 H, m), 5.08 (2 H, s), 5.09 (2 H, s), 5.17 (1 H, d, J = 4.7 Hz), 5.22 (1 H, d, J = 7.4 Hz), 5.57 (1 H, t, J = 4.4 Hz), 5.76 (1 H, d, J = 7.8 Hz), 6.70-7.05 (6 H, m), 7.15-7.50 (12 H, m) |

EXAMPLE 76

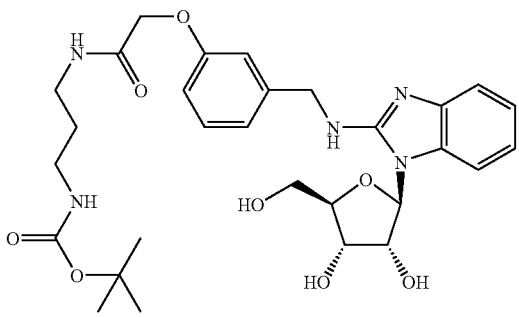

2-{3-[(3-t-Butoxycarbonylaminopropylcarbamoyl)methoxy]-benzylamino}-1-(β-D-ribofuranosyl)-1H-benzimidazole t-Butyl N-(3-aminopropyl)carbamate (0.37 g) and pyridine (0.51 mL) were dissolved in dichloromethane (5 mL). To the stirred mixture was added dropwise bromoacetylchloride (0.19 mL) under ice-cooling, and the mixture was stirred at room temperature for 3 hours. To the reaction mixture was added 1 mol/L hydrochloric acid, and the resulting mixture was extracted with ethyl acetate. The organic layer was washed with brine and dried over anhydrous magnesium sulfate. The filtrate was concentrated under reduced pressure, and the obtained residue was dissolved in N,N-dimethylformamide (2 mL). To the mixture were added 2-(3-hydroxybenzylamino)-1-(β-D-ribofuranosyl)-1H-benzimidazole (0.09 g) and potassium carbonate (0.14 g), and the mixture was stirred at 50° C. for 16 hours. After the insoluble material was removed by filtration, the reaction mixture was concentrated under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (0.02 g).

$^1$H-NMR (DMSO-d$_6$) δ ppm: 1.37 (9H, s), 1.45-1.60 (2H, m), 2.80-2.95 (2H, m), 3.03-3.15 (2H, m), 3.60-3.86 (2H, m), 3.95-4.03 (1H, m), 4.08-4.15 (1H, m), 4.38-4.47 (3H, m), 4.50-4.60 (2H, m), 5.22 (1H, d, J=4.6 Hz), 5.31 (1H, d, J=7.3 Hz), 5.60 (1H, t, J=4.5 Hz), 5.81 (1H, d, J=7.6 Hz), 6.70-7.00 (6H, m), 7.16 (1H, d, J=7.4 Hz), 7.23 (1H, dd, J=7.4 Hz, 8.1 Hz), 7.29 (1H, d, J=8.1 Hz), 7.40-7.50 (1H, m), 8.00-8.13 (1H, m)

EXAMPLE 77

The compound of Table 17 was prepared in a similar manner to that described in Example 76 using the corresponding materials.

TABLE 17

| Example No. | Structure | $^1$H-NMR δ ppm |
|---|---|---|
| Example 77 | 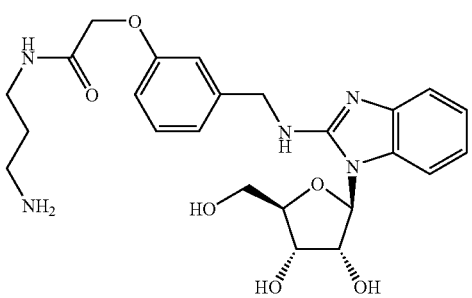 | (DMSO-d$_6$) 1.36 (9 H, s), 2.90-3.20 (4 H, m), 3.60-3.80 (2 H, m), 3.95-4.15 (2 H, m), 4.35-4.45 (3 H, m), 4.47-4.62 (2 H, m), 5.83 (1 H, d, J = 7.6 Hz), 6.70-7.05 (6 H, m), 7.10-7.60 (4 H, m), 8.00-8.13 (1 H, m) |

EXAMPLE 78

2-{3-[(3-Aminopropylcarbamoyl)methoxy]benzylamino}-1-(β-D-ribofuranosyl)-1H-benzimidazole 2-{3-[(3-t-Butoxycarbonylaminopropylcarbamoyl)methoxy]benzylamino}-1-(β-D-ribofuranosyl)-1H-benzimidazole (15 mg) was dissolved in 22% hydrochloride-ethanol solution, and the mixture was stirred at room temperature for 30 minutes. The reaction mixture was concentrated under reduced pressure, and the obtained residue was purified by preparative reverse phase column chromatography (Shiseido CAPSELL PAC C18UG80, 5 μm, 20×50 mm, flow rate 30 mL/minutes linear gradient, water/methanol=90/10-10/90) to give the title compound (9 mg).

$^1$H-NMR (DMSO-d$_6$) δ ppm:
1.40-1.55 (2H, m), 3.08-3.23 (2H, m), 3.60-3.75 (2H, m), 3.95-4.15 (2H, m), 4.35-4.45 (3H, m), 4.46-4.63 (2H, m), 5.81 (1H, d, J=7.6 Hz), 6.70-7.05 (5H, m), 7.10-7.35 (3H, m), 7.40-7.55 (1H, m), 8.05-8.20 (1H, m)

EXAMPLES 79-80

The compounds of Table 18 were prepared in a similar manner to that described in Example 78 using the corresponding materials.

2-[3-(4-Hydroxybutylamino)benzylamino]-1-(β-D-ribofuranosyl)-1H-benzimidazole

2-[3-(4-Benzyloxybutylamino)benzylamino]-1-(β-D-ribofuranosyl)-1H-benzimidazole (44 mg) was dissolved in ethanol (5 mL). To the solution was added a catalytic amount of 10% palladium-carbon powder, and the mixture was stirred at 60° C. under a hydrogen atmosphere for 24 hour. The insoluble material was removed by filtration, and the solvent of the filtrate was removed under reduced pressure to give the title compound (22 mg).

TABLE 18

| Example No. | Structure | $^1$H-NMR δ ppm |
|---|---|---|
| Example 79 | 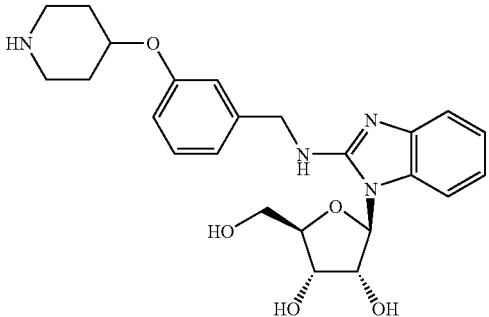 | (DMSO-d$_6$) 1.30-1.46 (2 H, m), 1.80-1.95 (2 H, m), 2.83-2.96 (2 H, m), 3.60-3.75 (2 H, m), 3.95-4.02 (1 H, m), 4.06-4.15 (1 H, m), 4.25-4.46 (3 H, m), 4.52 (2 H, d, J = 6.1 Hz), 5.20 (1 H, d, J = 4.3 Hz), 5.27 (1 H, d, J = 7.5 Hz), 5.60 (1 H, t, J = 4.4 Hz), 5.81 (1 H, d, J = 7.7 Hz), 6.76 (1 H, dd, J = 2.0 Hz, 8.0 Hz), 6.80-7.00 (4 H, m), 7.10-7.23 (2 H, m), 7.27 (1 H, d J = 7.8 Hz), 7.43 (1 H, t, J = 6.1 Hz) |
| Example 80 | 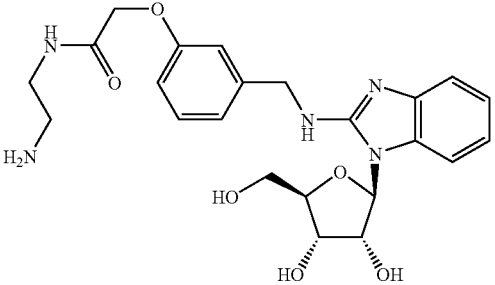 | (DMSO-d$_6$) 2.53-2.65 (2 H, m), 3.08-3.18 (2 H, m), 3.60-3.75 (2 H, m), 3.95-4.15 (2 H, m), 4.35-4.45 (3 H, m), 4.50-4.60 (2 H, m), 5.81 (1 H, d, J = 7.1 Hz), 6.75-7.05 (5 H, m), 7.10-7.35 (3 H, m), 7.40-7.50 (1 H, m), 7.95-8.05 (1 H, m) |

EXAMPLE 81

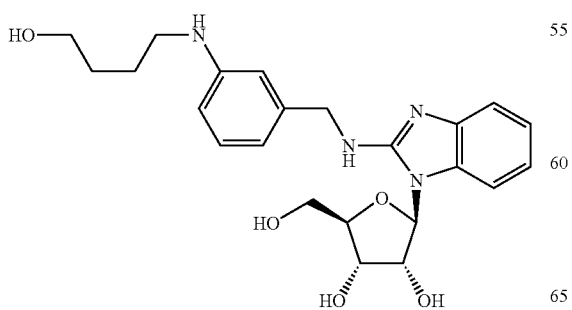

$^1$H-NMR (DMSO-d$_6$) δ ppm: 1.40-1.60 (4H, m), 2.90-3.02 (2H, m), 3.60-3.75 (2H, m), 3.94-4.02 (1H, m), 4.08-4.15 (1H, m), 4.30-4.55 (4H, m), 5.21 (1H, d, J=4.3 Hz), 5.28 (1H, d, J=7.8 Hz), 5.43-5.52 (1H, m), 5.57 (1H, t, J=4.5 Hz), 5.80 (1H, d, J=7.6 Hz), 6.39 (1H, d, J=7.8 Hz), 6.51 (1H, d, J=7.1 Hz), 6.55 (1H, s), 6.80-7.05 (3H, m), 7.15 (1H, d, J=7.7 Hz), 7.27 (1H, d J=7.7 Hz), 7.35 (1H, t, J=6.1 Hz)

EXAMPLES 82-84

The compounds of Table 19 were prepared in a similar manner to that described in Example 81 using the corresponding materials.

TABLE 19

| Example No. | Structure | $^1$H-NMR δ ppm |
|---|---|---|
| Example 82 | 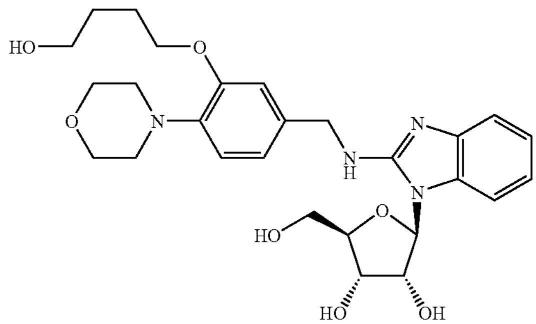 | (DMSO-$d_6$) 1.50-1.62 (2 H, m), 1.67-1.82 (2 H, m), 2.85-3.00 (4 H, m), 3.40-3.50 (2 H, m), 3.60-3.80 (6 H, m), 3.90-4.15 (5 H, m), 4.30-4.55 (4 H, m), 5.20 (1 H, d, J = 4.4 Hz), 5.30 (1 H, d, J = 7.4 Hz), 5.50-5.70 (1 H, m), 5.80 (1 H, d, J = 7.7 Hz), 6.75-7.05 (5 H, m), 7.10-7.50 (3 H, m) |
| Example 83 | 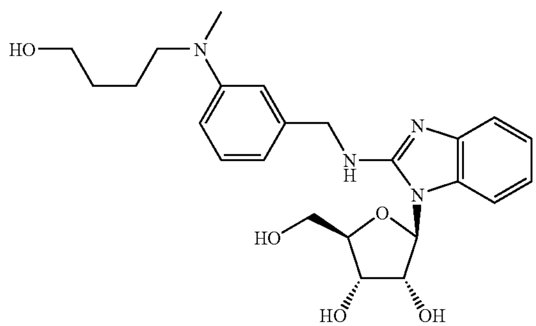 | (DMSO-$d_6$) 1.30-1.55 (4 H, m), 2.84 (3 H, s), 3.20-3.45 (4 H, m), 3.60-3.75 (2 H, m), 3.95-4.02 (1 H, m), 4.06-4.15 (1 H, m), 4.35-4.46 (1 H, m), 4.50 (2 H, d, J = 6.1 Hz), 5.82 (1 H, d, J = 8.1 Hz), 6.53 (1 H, d, J = 8.2 Hz), 6.60 (1 H, d, J = 7.4 Hz), 6.71 (1 H, s), 6.80-7.50 (6 H, m) |
| Example 84 | 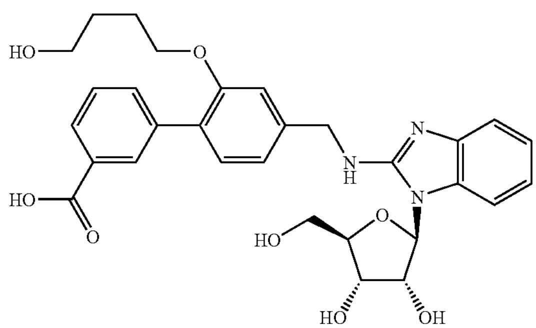 | (CD$_3$OD) 1.50-1.63 (2 H, m), 1.68-1.80 (2 H, m), 3.49 (2 H, t, J = 6.5 Hz), 3.80-3.90 (2 H, m), 4.01 (2 H, t, J = 6.1 Hz), 4.10-4.20 (1 H, m), 4.25-4.35 (1 H, m), 4.57-4.78 (3 H, m), 6.00 (1 H, d, J = 7.3 Hz), 7.00-7.17 (4 H, m), 7.24-7.35 (3 H, m), 7.43 (1 H, t, J = 7.7 Hz), 7.67 (1 H, d, J = 7.6 Hz), 7.92 (1 H, d, J = 7.6 Hz), 8.16 (1 H, s) |

EXAMPLE 85

2-{2-[3,4-Bis(4-aminobutoxy)phenyl]ethylamino}-1-(β-D-ribofuranosyl)-1H-benzimidazole

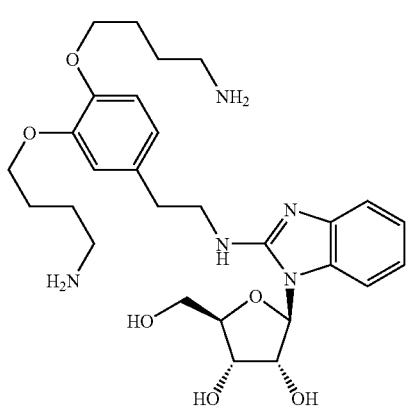

2-{2-[3,4-Bis(benzyloxy)phenyl]ethylamino}-1-(β-D-ribofuranosyl)-1H-benzimidazole (0.35 g) was dissolved in ethanol (5 mL). To the solution was added a catalytic amount of 10% palladium-carbon powder, and the mixture was stirred at 60° C. under a hydrogen atmosphere for 24 hour. The insoluble material was removed by filtration, and the obtained residue and potassium carbonate (0.30 g) were suspended in N,N-dimethylformamide (5 mL). To the reaction mixture was added N-(4-bromobutyl)phthalimide (0.60 g), and the mixture was stirred at 60° C. for 16 hours. The insoluble material was removed by filtration, and the reaction mixture was concentrated under reduced pressure. The obtained residue was dissolved in ethanol (5 mL). To the reaction mixture was added hydrazine monohydrate (0.5 mL), and the mixture was stirred at 90° C. for 6 hours. The reaction mixture was concentrated under reduced pressure, and the obtained residue was purified by preparative reverse phase column chromatog raphy (Shiseido CAPSELL PAC C18UG80, 5 μm, 20×50 mm, flow rate 30 mL/minutes linear gradient, water/methanol=70/30-10/90) to give the title compound (0.02 g).

$^1$H-NMR (CD$_3$OD) δ ppm: 1.55-1.90 (8H, m), 2.65-2.83 (4H, m), 2.89 (2H, t, J=7.2 Hz), 3.62 (2H, t, J=7.2 Hz), 3.70-3.83 (2H, m), 3.90-4.10 (5H, m), 4.19 (1H, dd, J=2.5 Hz, 6.1 Hz), 4.44 (1H, dd, J=6.1 Hz, 7.4 Hz), 5.87 (1H, d, J=7.4 Hz), 6.78 (1H, dd, J=1.7 Hz, 7.9 Hz), 6.85 (1H, d, J=7.9 Hz), 6.89 (1H, d, J=1.7 Hz), 6.98 (1H, t, J=7.6 Hz), 7.04 (1H, t, J=7.6 Hz), 7.23 (1H, d, J=7.6 Hz), 7.28 (1H, d, J=7.6 Hz)

$^1$H-NMR (DMSO-d$_6$) δ ppm: 1.55-1.73 (2H, m), 1.85-1.96 (2H, m), 2.20-2.35 (2H, m), 2.60-2.75 (2H, m), 2.84 (2H, s), 3.60-3.75 (2H, m), 3.95-4.02 (1H, m), 4.07-4.15 (1H, m), 4.25-4.45 (2H, m), 4.52 (2H, d, J=6.0 Hz), 5.20 (1H, d, J=4.5 Hz), 5.27 (1H, d, J=7.7 Hz), 5.59 (1H, t, J=4.2 Hz), 5.81 (1H, d, J=7.5 Hz), 6.77 (1H, dd, J=1.8 Hz, 8.4 Hz), 6.83-7.00 (4H, m), 7.04-7.23 (4H, m), 7.27 (1H, d J=7.8 Hz), 7.43 (1H, t, J=6.0 Hz)

EXAMPLE 87

The compound of Table 20 was prepared in a similar manner to that described in Example 86 using the corresponding materials.

TABLE 20

| Example No. | Structure | $^1$H-NMR δ ppm |
|---|---|---|
| Example 87 | 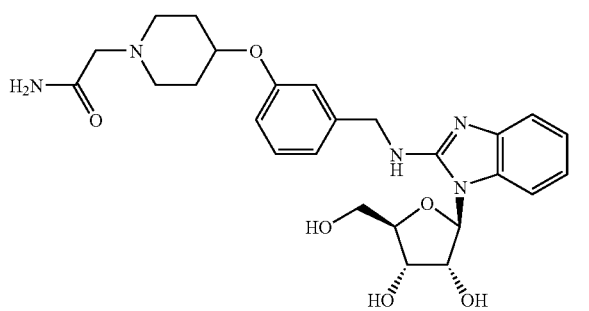 | (DMSO-d$_6$) 1.45-1.65 (2 H, m), 1.80-1.95 (2 H, m), 2.10-2.25 (2 H, m), 2.37 (2 H, t, J = 6.2 Hz), 2.60-2.75 (2 H, m), 3.40-3.53 (2 H, m), 3.60-3.80 (2 H, m), 3.95-4.03 (1 H, m), 4.05-4.14 (1 H, m), 4.23-4.45 (3 H, m), 4.52 (2 H, d, J = 6.1 Hz), 5.20 (1 H, d, J = 4.5 Hz), 5.27 (1 H, d, J = 7.5 Hz), 5.59 (1 H, t, J = 4.4 Hz), 5.81 (1 H, d, J = 7.5 Hz), 6.76 (1 H, dd, J = 2.1 Hz, 8.1 Hz), 6.83-7.00 (4 H, m), 7.10-7.23 (2 H, m), 7.28 (1 H, d J = 7.6 Hz), 7.43 (1 H, t, J = 6.1 Hz) |

EXAMPLE 86

2-[3-(N-Carbamoylmethylpiperidin-4-yloxy)benzylamino]-1-(β-D-ribofuranosyl)-1H-benzimidazole 2-[3-(Piperidin-4-yloxy)benzylamine]-1-(β-D-ribofuranosyl)-1H-benzimidazole (50 mg), bromoacetamide (20 mg) and potassium carbonate (23 mg) were suspended in N,N-dimethylformamide (5 mL), and the mixture was stirred at 60° C. for 16 hours. The insoluble material was removed by filtration, and the reaction mixture was concentrated under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=90/10-10/90) to give the title compound (30 mg).

EXAMPLE 88

2-[3-(N,N-Dimethylpiperidinium-4-yloxy)benzylamino]-1-(β-D-ribofuranosyl)-1H-benzimidazole iodide 2-[3-(Piperidin-4-yloxy)benzylamino]-1-(β-D-ribofuranosyl)-1H-benzimidazole (0.1 g) was dissolved in ethanol (5 mL). To the reaction mixture was added iodomethane (78 mg), and the mixture was stirred at 60° C. for 16 hours. The reaction mixture was concentrated under reduced pressure, and the obtained residue was purified by preparative reverse phase column chromatography (Shiseido CAPSELL PAC C18UG80, 5 μm, 20×50 mm, flow rate 30 mL/minutes linear gradient, water/methanol=90/10-10/90) to give the title compound (30 mg).

$^1$H-NMR (CD$_3$OD) δ ppm: 2.05-2.00 (2H, m), 2.25-2.40 (2H, m), 3.23 (3H, s), 3.30 (3H, s), 3.40-3.50 (2H, m), 3.55-3.70 (2H, m), 3.78-3.93 (2H, m), 4.20-4.32 (2H, m), 4.55-

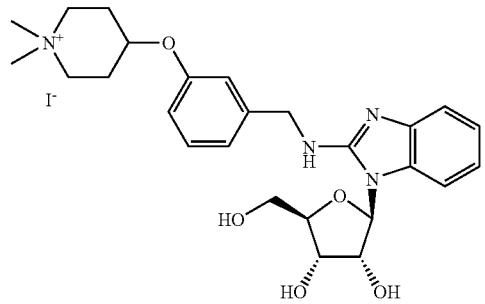

4.63 (1H, m), 4.67-4.78 (3H, m), 6.10 (1H, d, J=7.7 Hz) 6.90-7.15 (3H, m), 7.25-7.45 (4H, m), 7.50-7.60 (1H, m)

EXAMPLE 89

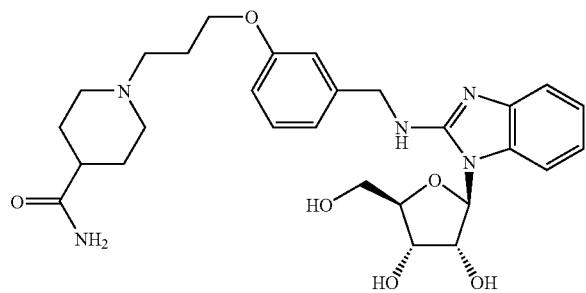

2-{3-[3-(4-Carbamoylpiperidin-1-yl)propoxy]benzylamino}-1-(β-D-ribofuranosyl)-1H-benzimidazole 2-[3-(3-Chloropropoxy)benzylamino]-1-(2,3,5-tri-O-acetyl-β-D-ribofuranosyl)-1H-benzimidazole (0.67 g) and sodium iodide (0.52 g) were suspended in acetone (15 mL), and the mixture was refluxed for 16 hours. The insoluble material was removed by filtration, and the filtrate was concentrated under reduced pressure. The obtained residue, isonipecotamide (0.30 g) and potassium carbonate (0.32 g) were suspended in acetonitrile (5 mL), and the mixture was stirred at 70° C. for 16 hours. The insoluble material was removed by filtration, and the filtrate was concentrated under reduced pressure. The obtained residue was dissolved in methanol (2 mL). To the reaction mixture was added 5 mol/L aqueous sodium hydroxide solution (0.5 mL), and the mixture was stirred at room temperature for 1 hour. To the reaction mixture was added acetic acid (1 mL), and the mixture was concentrated under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (0.38 g).

$^1$H-NMR (CD$_3$OD) δ ppm: 1.60-2.30 (9H, m), 2.40-2.65 (2H, m), 2.85-3.05 (2H, m), 3.75-3.90 (2H, m), 3.99 (2H, t, J=6.2 Hz), 4.10-4.15 (1H, m), 4.20-4.30 (1H, m), 4.50-4.70 (3H, m), 5.96 (1H, d, J=7.4 Hz), 6.70-6.80 (1H, m), 6.85-7.35 (7H, m)

EXAMPLES 90-103

The compounds of Table 21 were prepared in a similar manner to that described in Example 89 using the corresponding materials.

TABLE 21

| Example No. | Structure | $^1$H-NMR δ ppm |
|---|---|---|
| Example 90 | 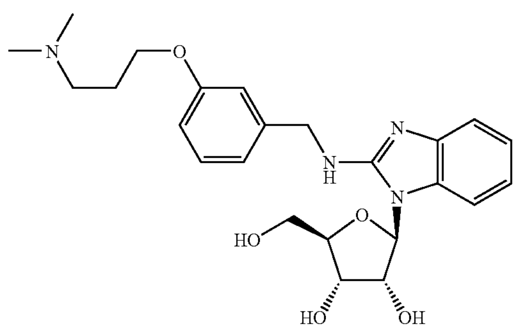 | (CD$_3$OD) 1.80-2.00 (2 H, m), 2.22 (6 H, s), 2.40-2.55 (2 H, m), 3.75-3.90 (2 H, m), 3.98 (2 H, t, J = 6.2 Hz), 4.10-4.15 (1 H, m), 4.20-4.30 (1 H, m), 4.50-4.70 (3 H, m), 5.96 (1 H, d, J = 7.7 Hz), 6.70-7.40 (8 H, m) |
| Example 91 | 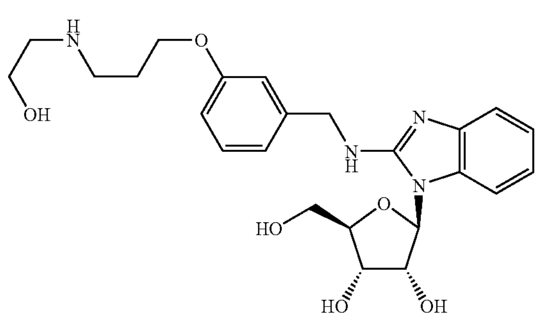 | (CD$_3$OD) 1.85-2.00 (2 H, m), 2.71 (2 H, t, J = 5.5 Hz), 2.78 (2 H, t, J = 7.1 Hz), 3.64 (2 H, t, J = 5.5 Hz), 3.75-3.85 (2 H, m), 4.03 (2 H, t, J = 6.3 Hz), 4.05-4.15 (1 H, m), 4.20-4.30 (1 H, m), 4.50-4.70 (3 H, m), 5.95 (1 H, d, J = 7.1 Hz), 6.70-6.85 (1 H, m), 6.90-7.35 (7 H, m) |

TABLE 21-continued
| Example No. | Structure | ¹H-NMR δ ppm |
|---|---|---|
| Example 92 | 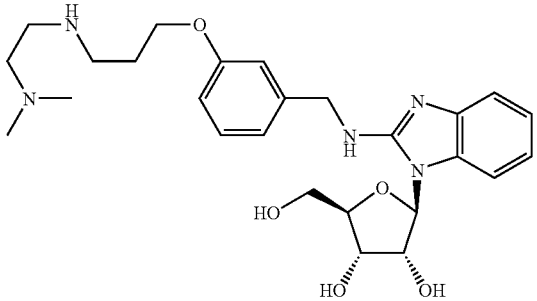 | (CD₃OD) 1.85-2.00 (2 H, m), 2.21 (6 H, s), 2.35-2.50 (2 H, m), 2.60-2.80 (4 H, m), 3.75-3.85 (2 H, m), 4.01 (2 H, t, J = 6.0 Hz), 4.10-4.15 (1 H, m), 4.20-4.30 (1 H, m), 4.50-4.70 (3 H, m), 5.95 (1 H, d, J = 7.4 Hz), 6.70-6.80 (1 H, m), 6.90-7.35 (7 H, m) |
| Example 93 | 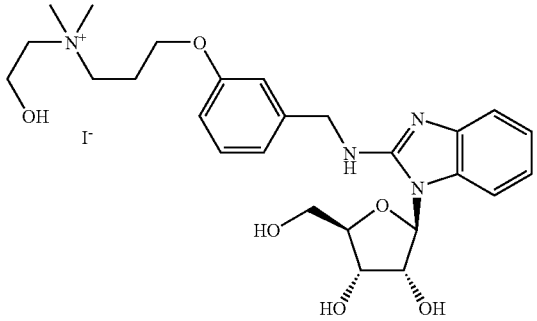 | (CD₃OD) 2.10-2.30 (2 H, m), 3.10 (6 H, s), 3.35-3.45 (2 H, m), 3.50-3.60 (2 H, m), 3.75-4.35 (8 H, m), 4.55-4.70 (3 H, m), 5.96 (1 H, d, J = 7.3 Hz), 6.75-6.85 (1 H, m), 6.90-7.10 (4 H, m), 7.15-7.35 (3 H, m) |
| Example 94 | 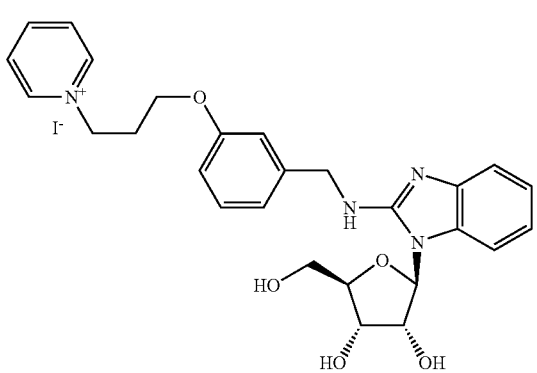 | (CD₃OD) 2.40-2.55 (2 H, m), 3.75-3.90 (2 H, m), 4.00-4.30 (4 H, m), 4.50-4.65 (3 H, m), 4.70-4.85 (2 H, m), 5.97 (1 H, d, J = 7.3 Hz), 6.55-6.75 (2 H, m), 6.80-7.45 (6 H, m), 7.75-7.95 (2 H, m), 8.10-8.25 (1 H, m), 8.85-8.95 (2 H, m) |
| Example 95 | 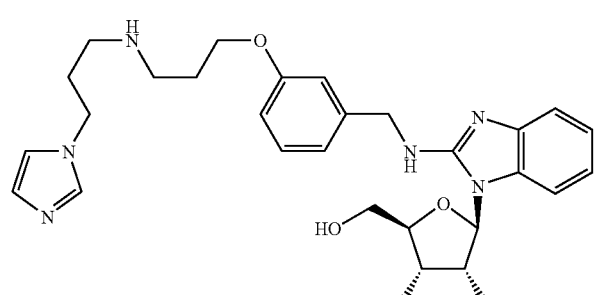 | (CD₃OD) 1.80-2.00 (4 H, m), 2.51 (2 H, t, J = 7.3 Hz), 2.70 (2 H, t, J = 7.1 Hz), 3.75-3.85 (2 H, m), 3.95-4.05 (4 H, m), 4.10-4.15 (1 H, m), 4.20-4.30 (1 H, m), 4.50-4.70 (3 H, m), 5.95 (1 H, d, J = 7.2 Hz), 6.70-6.80 (1 H, m), 6.85-7.35 (9 H, m), 7.60 (1 H, s) |

TABLE 21-continued

| Example No. | Structure | $^1$H-NMR δ ppm |
|---|---|---|
| Example 96 | 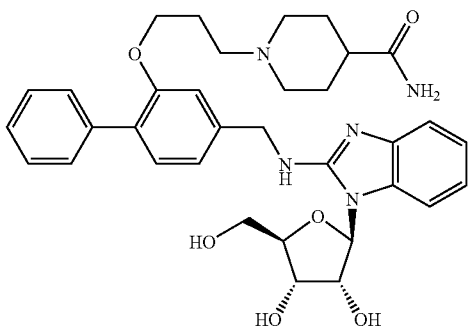 | (CD$_3$OD) 1.40-2.50 (11 H, m), 2.75-2.95 (2 H, m), 3.75-4.35 (6 H, m), 4.55-4.75 (3 H, m), 5.98 (1 H, d, J = 7.3 Hz), 6.90-7.55 (12 H, m) |
| Example 97 | 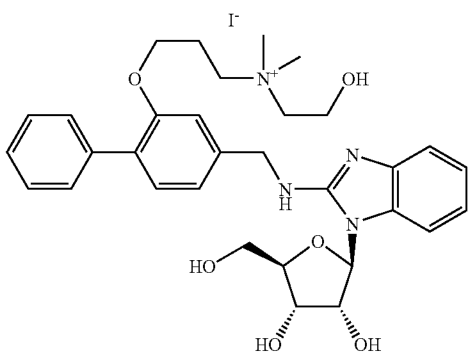 | (CD$_3$OD) 2.00-2.15 (2 H, m), 2.95 (6 H, s), 3.20-3.30 (2 H, m), 3.75-3.90 (4 H, m), 4.00-4.35 (4 H, m), 4.55-4.75 (3 H, m), 5.98 (1 H, d, J = 7.6 Hz), 6.95-7.55 (12 H, m) |
| Example 98 | 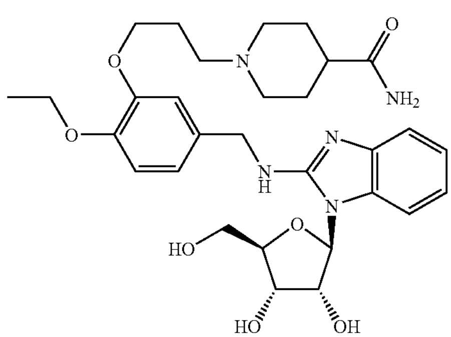 | (CD$_3$OD) 1.35 (3 H, t, J = 7.0 Hz), 1.60-2.30 (9 H, m), 2.45-2.55 (2 H, m), 2.85-3.00 (2 H, m), 3.75-3.90 (2 H, m), 3.95-4.15 (5 H, m), 4.20-4.30 (1 H, m), 4.45-4.65 (3 H, m), 5.94 (1 H, d, J = 7.6 Hz), 6.80-7.15 (5 H, m), 7.20-7.35 (2 H, m) |
| Example 99 | 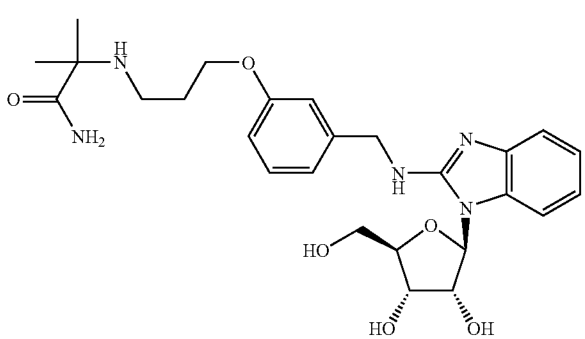 | (CD$_3$OD) 1.26 (6 H, s), 1.85-1.95 (2 H, m), 2.60-2.65 (2 H, m), 3.75-3.85 (2 H, m), 4.00-4.15 (3 H, m), 4.20-4.30 (1 H, m), 4.50-4.65 (3 H, m), 5.95 (1 H, d, J = 7.6 Hz), 6.75-6.80 (1 H, m), 6.90-7.05 (4 H, m), 7.15-7.30 (3 H, m) |

TABLE 21-continued

| Example No. | Structure | $^1$H-NMR δ ppm |
|---|---|---|
| Example 100 | 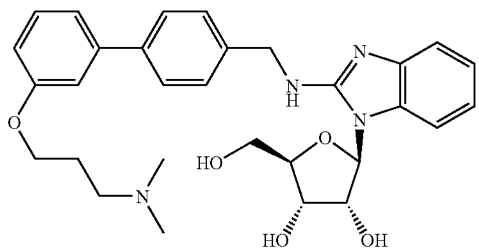 | (CD$_3$OD) 1.90-2.05 (2 H, m), 2.27 (6 H, s), 2.45-2.60 (2 H, m), 3.75-3.90 (2 H, m), 4.00-4.30 (4 H, m), 4.55-4.80 (3 H, m), 5.96 (1 H, d, J = 7.8 Hz), 6.80-7.60 (12 H, m) |
| Example 101 | 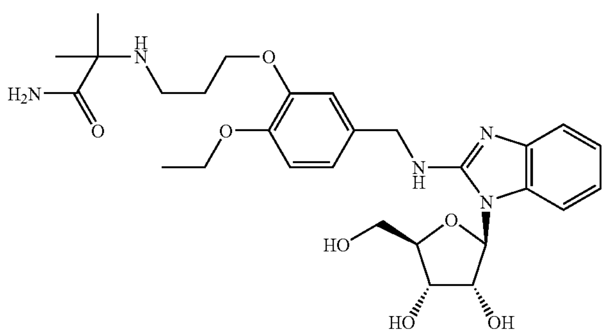 | (CD$_3$OD) 1.26 (6 H, s), 1.35 (3 H, t, J = 7.1 Hz), 1.85-1.95 (2 H, m), 2.60-2.70 (2 H, m), 3.75-3.85 (2 H, m), 3.95-4.15 (5 H, m), 4.20-4.30 (1 H, m), 4.45-4.60 (3 H, m), 5.94 (1 H, d, J = 7.3 Hz), 6.80-7.05 (5 H, m), 7.20-7.30 (2 H, m) |
| Example 102 | 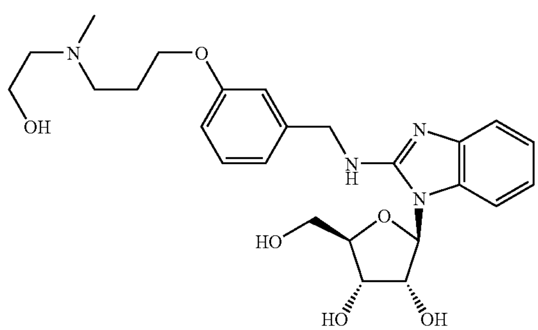 | (CD$_3$OD) 1.85-2.00 (2 H, m), 2.29 (3 H, s), 2.56 (2 H, t, J = 6.0 Hz), 2.61 (2 H, t, J = 7.6 Hz), 3.66 (2 H, t, J = 6.0 Hz), 3.75-3.90 (2 H, m), 4.00 (2 H, t, J = 6.3 Hz), 4.10-4.15 (1 H, m), 4.20-4.30 (1 H, m), 4.50-4.70 (3 H, m), 5.95 (1 H, d, J = 7.4 Hz), 6.70-6.80 (1 H, m), 6.90-7.35 (7 H, m) |
| Example 103 | 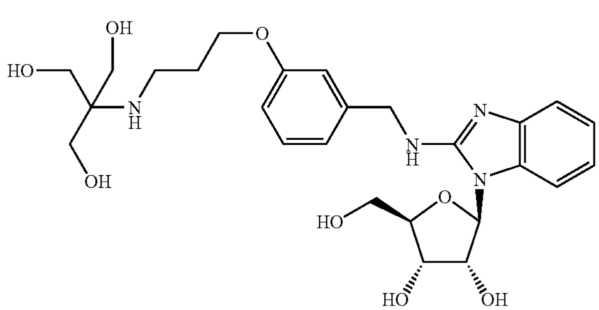 | (CD$_3$OD) 1.85-2.00 (2 H, m), 2.83 (2 H, t, J = 7.0 Hz), 3.55 (6 H, s), 3.75-3.90 (2 H, m), 4.05 (2 H, t, J = 6.2 Hz), 4.10-4.15 (1 H, m), 4.20-4.30 (1 H, m), 4.50-4.70 (3 H, m), 5.95 1 H), d, J = 7.4 Hz), 6.75-6.85 (1 H, m), 6.90-7.35 (7 H, m) |

EXAMPLE 104
The compounds of Table 22 can be prepared in a similar manner to that described in Example 89 using the corresponding materials.
TABLE 22
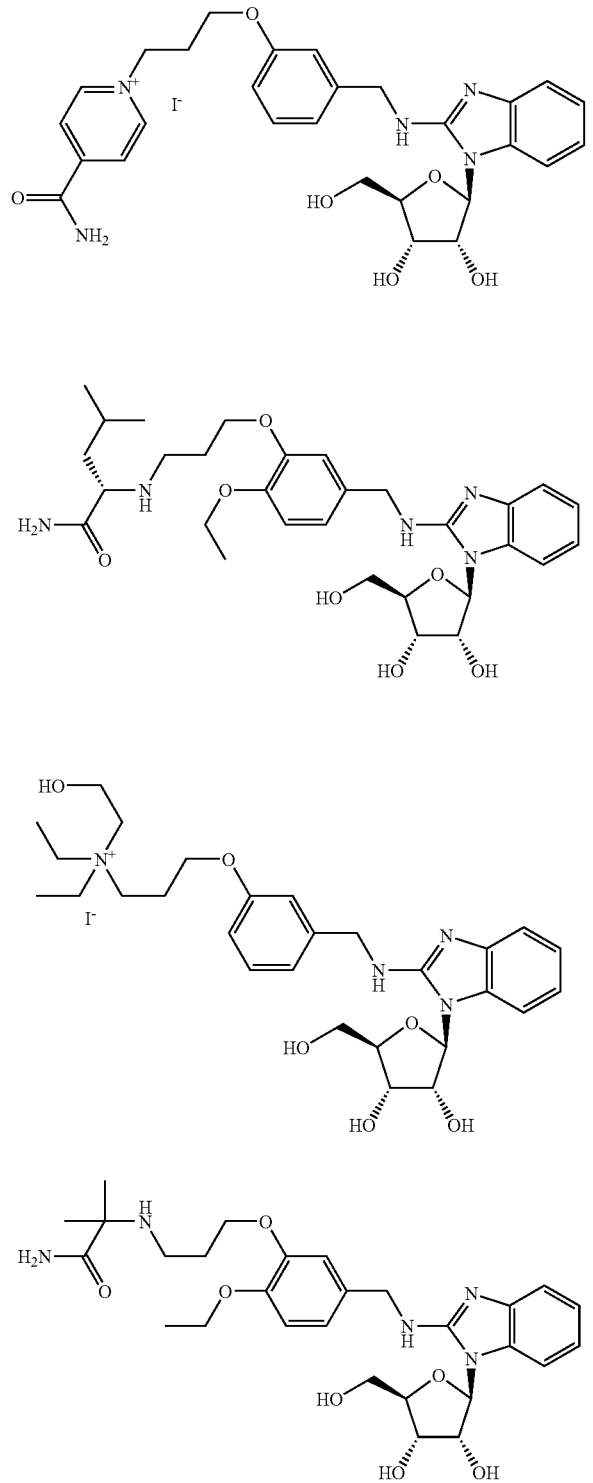
TABLE 22-continued
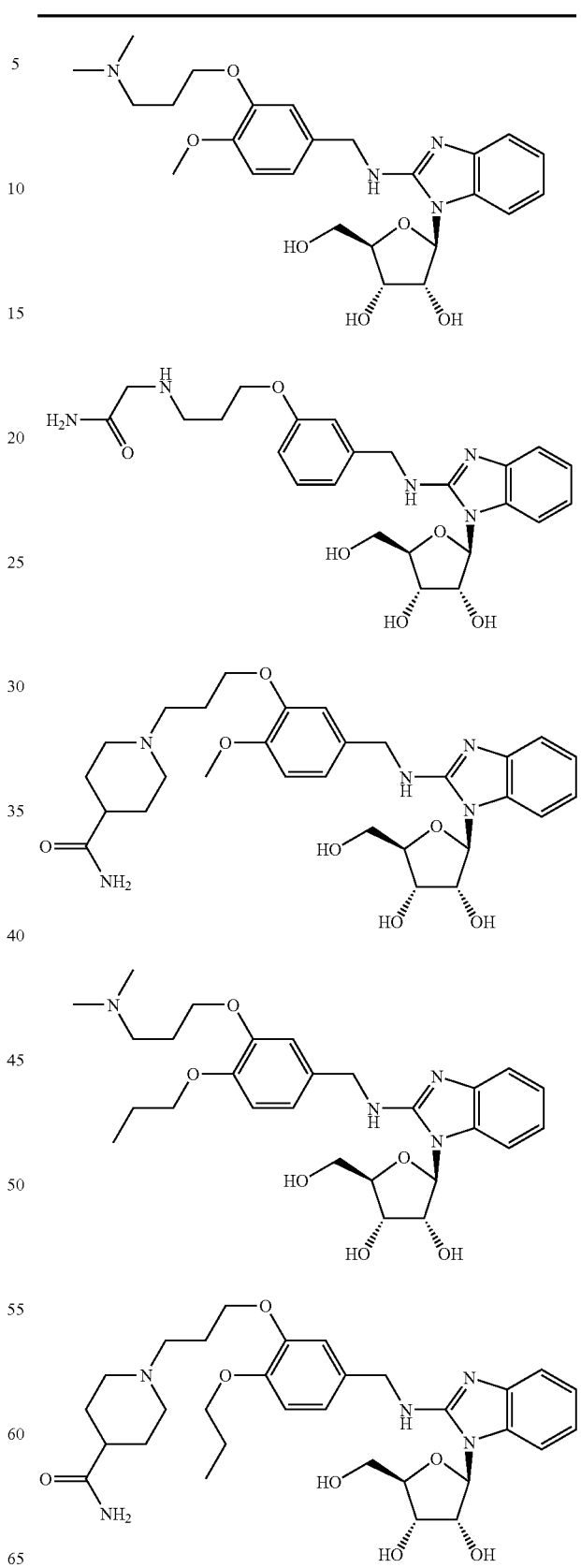

TABLE 22-continued
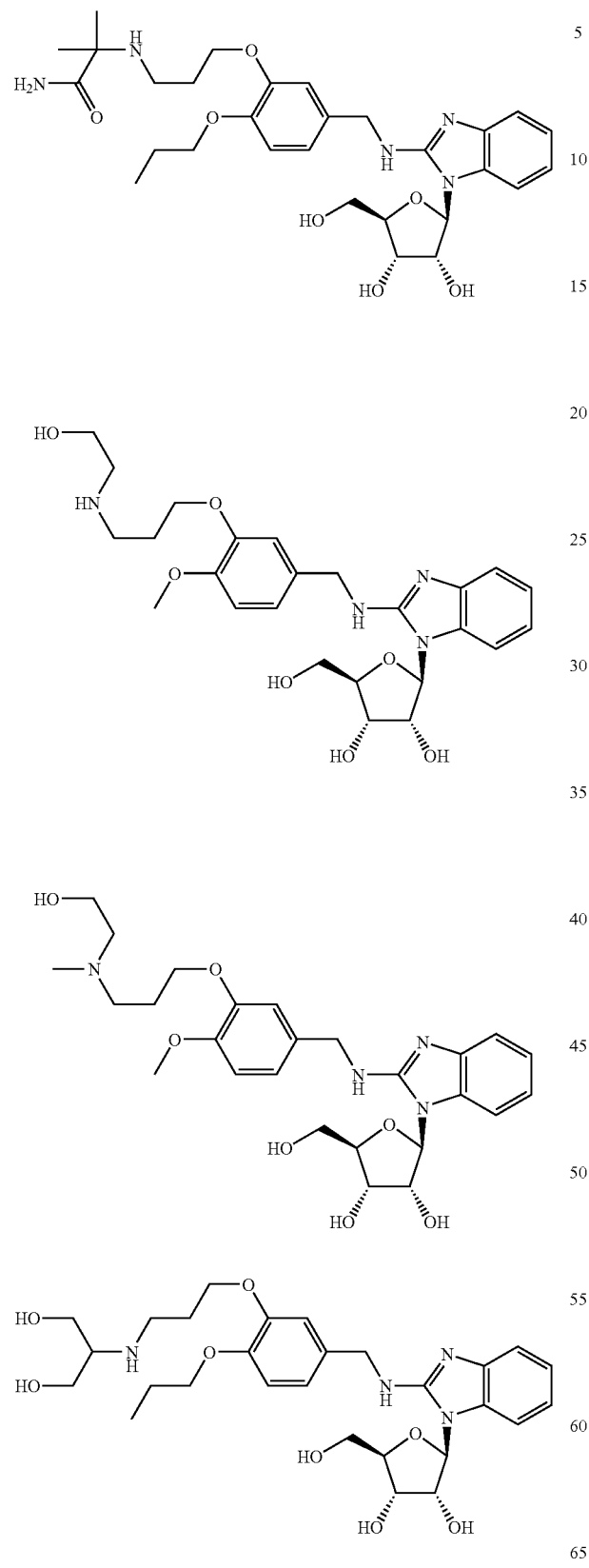
TABLE 22-continued
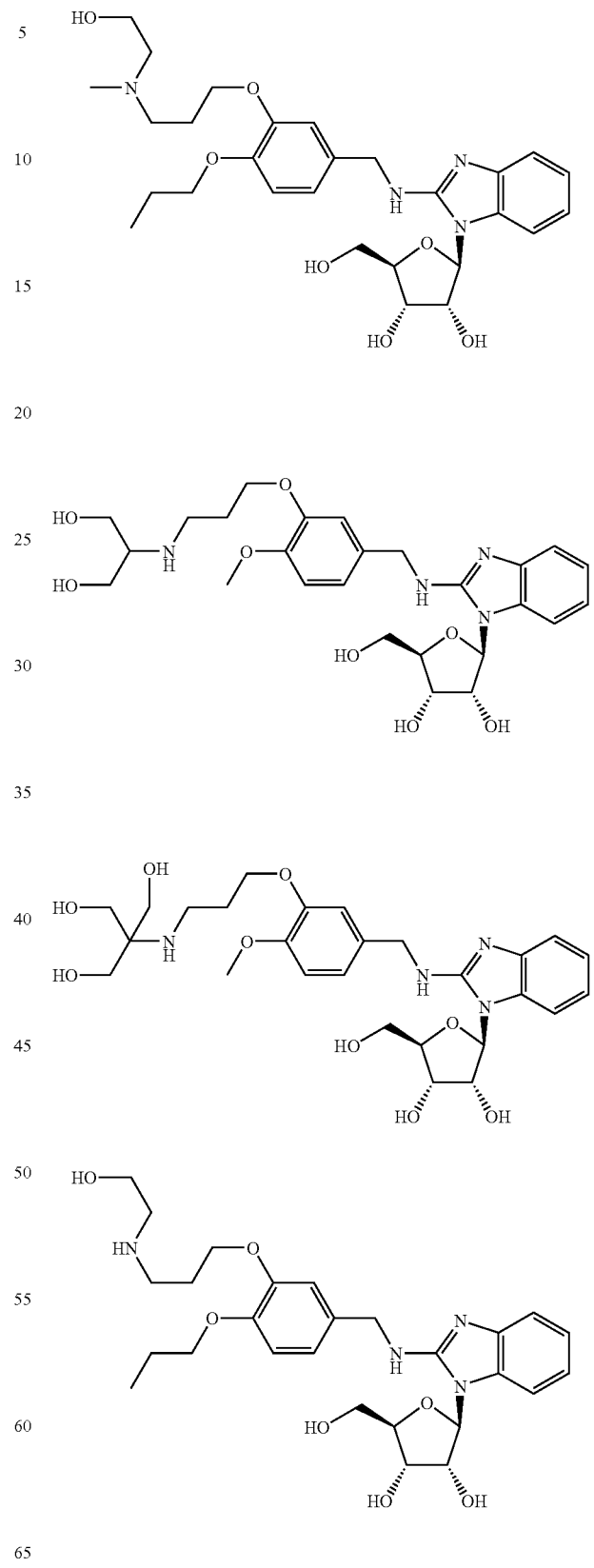

TABLE 22-continued
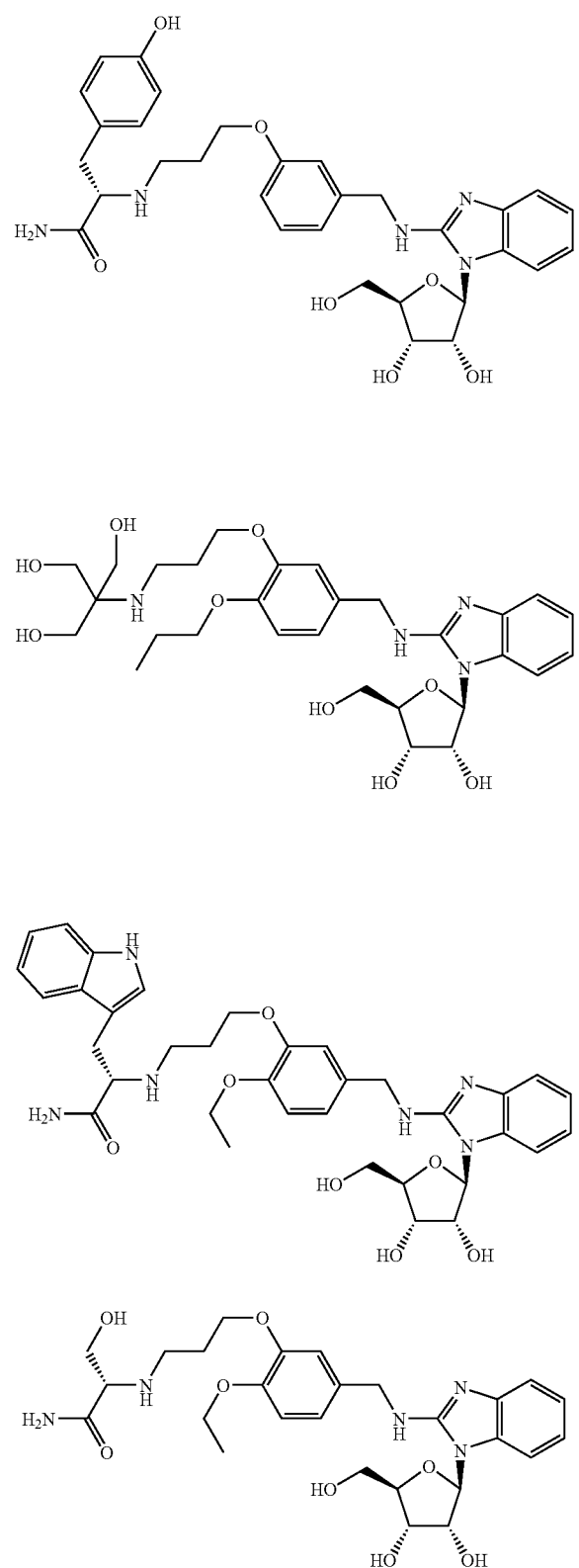
TABLE 22-continued
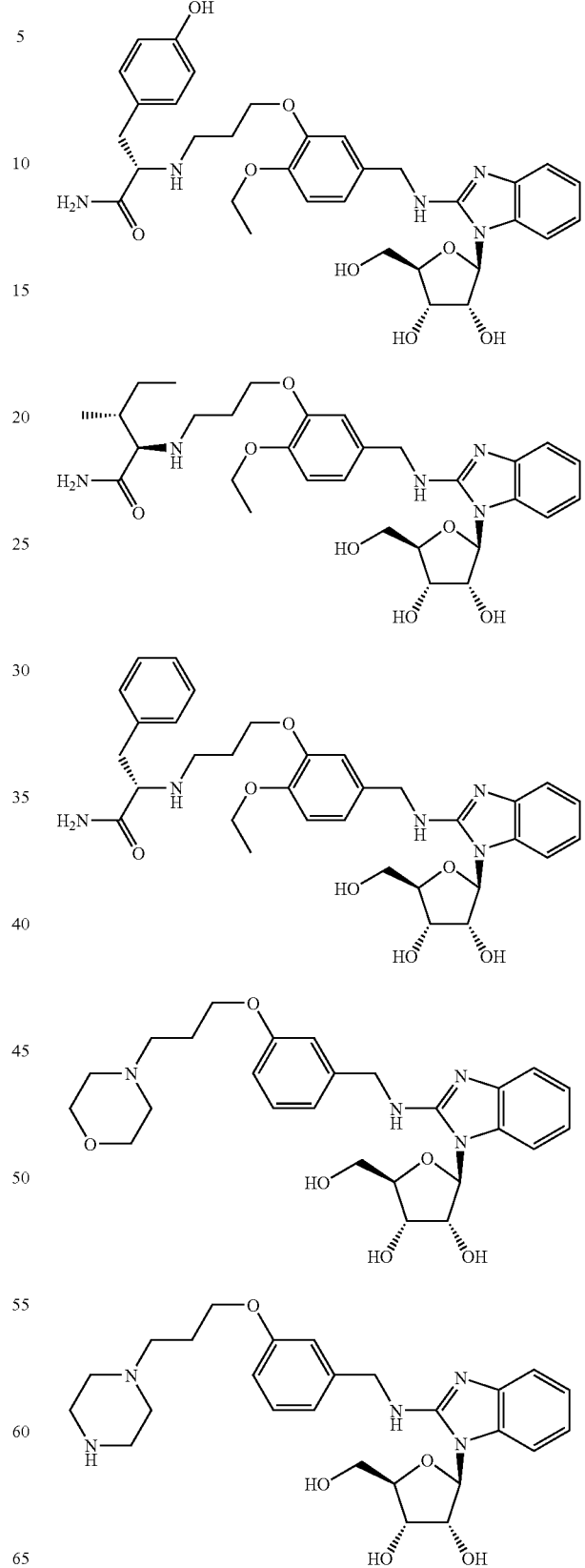

TABLE 22-continued

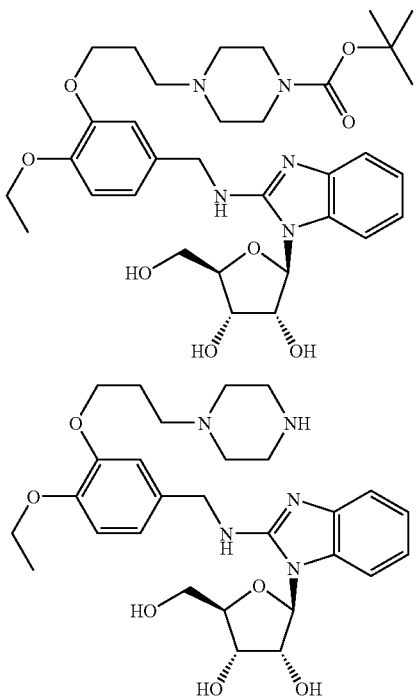

EXAMPLE 105

2-{3-(4-Hydroxybutoxy)-4-[3-(2-dimethylaminoeth-ylcarbamoyl)phenyl]benzylamino}-1-(β-D-ribofuranosyl)-1H-benzimidazole

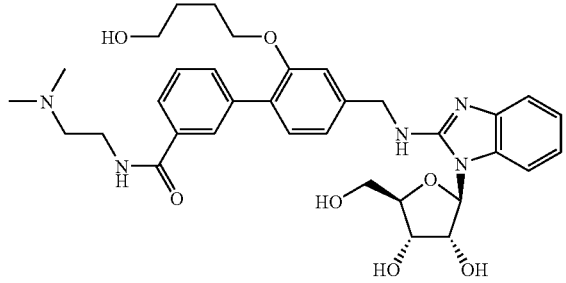

2-[3-(4-Hydroxybutoxy)-4-(3-carboxyphenyl)benzy-lamino]-1-(β-D-ribofuranosyl)-1H-benzimidazole (20 mg), N,N-dimethylethylenediamine (4 mg) and 1-hydroxybenzo-triazole (7 mg) were suspended in N,N-dimethylformamide (1 mL) at room temperature. To the mixture was added 1-ethyl-3-(3-dimethylaminopropyl)carbodiimide hydrochloride (10 mg), and the mixture was stirred at room temperature for 13 hours. The reaction mixture was concentrated under reduced pressure, and the obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (16 mg).

¹H-NMR (CD₃OD) δ ppm: 1.50-1.62 (2H, m), 1.65-1.78 (2H, m), 2.31 (6H, s), 2.58 (2H, t, J=6.8 Hz), 3.47 (2H, t, J=6.6 Hz), 3.52 (2H, t, J=6.8 Hz), 3.78-3.90 (2H, m), 3.99 (2H, t, J=6.3 Hz), 4.10-4.19 (1H, m), 4.28 (1H, dd, J=2.3 Hz, 5.8 Hz), 4.58-4.75 (3H, m), 5.97 (1H, d, J=7.4 Hz), 6.95-7.10 (3H, m), 7.14 (1H, s), 7.21-7.32 (3H, m), 7.44 (1H, t, J=7.8 Hz), 7.66 (1H, d, J=7.8 Hz), 7.73 (1H, d, J=7.8 Hz), 7.97 (1H, s)

EXAMPLE 106

The compounds of Table 23 can be prepared in a similar manner to that described in Example 105 using the corresponding materials.

TABLE 23

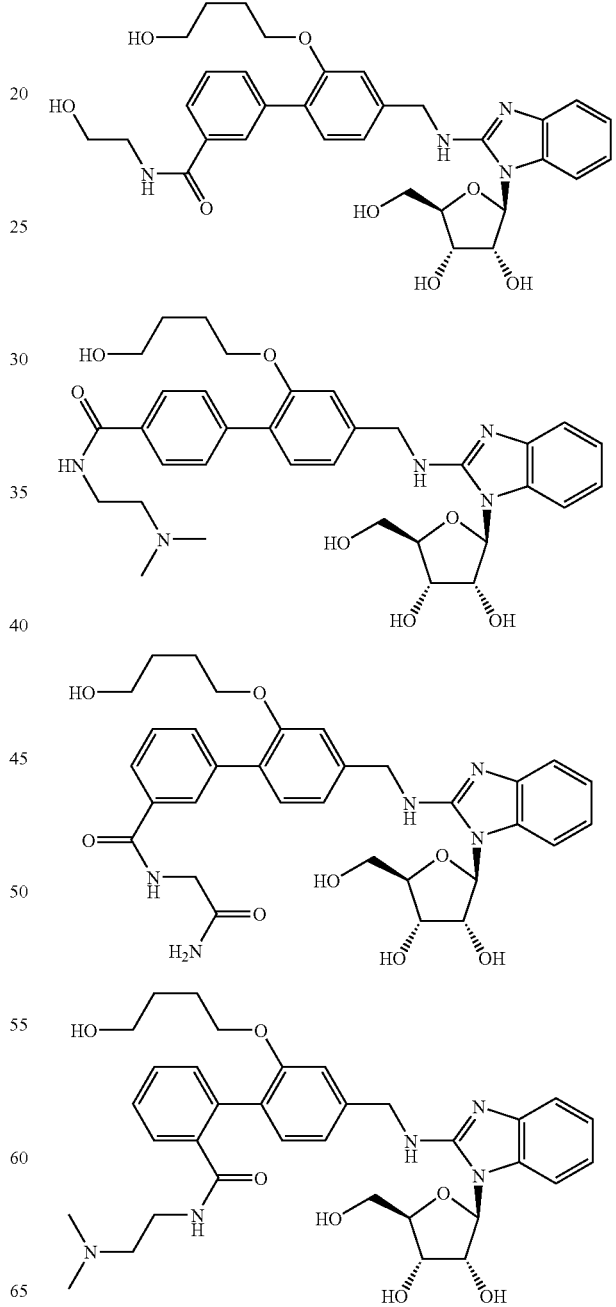

TABLE 23-continued

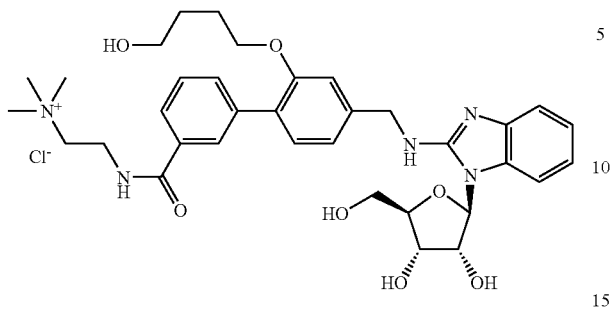

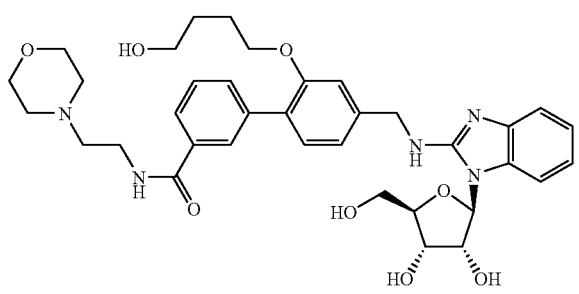

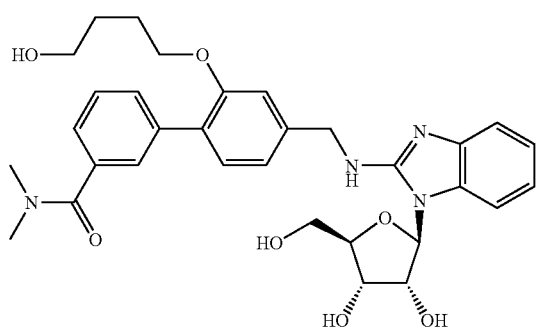

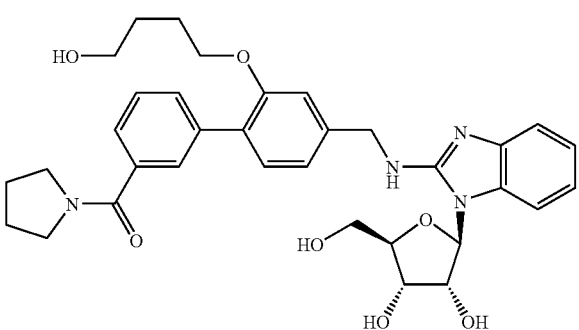

EXAMPLE 107

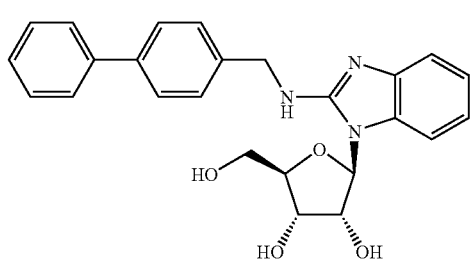

1-(β-D-Arabinofuranosyl)-2-(4-phenylbenzy-
lamino)-1H-benzimidazole

2-Chloro-1-(β-D-ribofuranosyl)-1H-benzimidazole (0.5 g) was suspended in pyridine (8.8 mL). To the stirred mixture was added dropwise 1,3-dichloro-1,1,3,3-tetraisopropyldisiloxane (0.59 mL) under ice-cooling, and the mixture was stirred at room temperature for 26 hours. To the reaction mixture was added methanol (2 mL), and the mixture was concentrated under reduced pressure. To the obtained residue was added water, and the resulting mixture was extracted with ethyl acetate. The organic layer was washed with 1 mol/L hydrochloric acid, a saturated aqueous sodium hydrogen carbonate solution and brine successively and dried over anhydrous magnesium sulfate. The filtrate was concentrated under reduced pressure, and the obtained residue was purified by column chromatography on silica gel (ethyl acetate/hexane=2/9) to give 2-chloro-1-[3,5-O,O-1,1,3,3-tetra-isopropyldisiloxanyl)-β-D-ribofuranosyl]-1H-benzimidazole (0.35 g). The obtained compound (0.34 g), triethylamine (0.12 mL) and 4-dimethylaminopyridine (0.08 g) were dissolved in dichloromethane (13 mL), and to the stirred mixture was added dropwise trifluoromethanesulfonylchloride (0.09 mL) under ice-cooling. The mixture was stirred at room temperature for 1 hour. To the reaction mixture was added a saturated aqueous sodium hydrogen carbonate solution (10 mL), and the resulting mixture was extracted with ethyl acetate. The organic layer was washed with brine and dried over anhydrous magnesium sulfate. The filtrate was concentrated under reduced pressure, and the obtained residue was dissolved in N,N-dimethylformamide (3 mL). To the mixture was cesium acetate (0.17 g), and the mixture was stirred at 30° C. for 15 hours. To the reaction mixture was added water (10 mL), and the resulting mixture was extracted with diethyl ether. The organic layer was washed with water and brine successively and dried over anhydrous magnesium sulfate. The filtrate was concentrated under reduced pressure, and the obtained residue was dissolved in tetrahydrofuran (3.9 mL). To the stirred mixture was added dropwise 1 mol/L tetrabutylammonium fluoride-tetrahydrofuran solution (1.47 mL) under ice-cooling. The mixture was stirred under ice-cooling for 1 hour. To the reaction mixture was added acetic acid (0.08 mL), and the mixture was concentrated under reduced pressure. The obtained residue was purified by column chromatography on silica gel (ethylacetate/hexane=4/1) to give 1-(2-O-acetyl-β-D-arabinofuranosyl)-2-chloro-1H-benzimidazole (0.12 g). The obtained compound (0.12 g), 4-phenylbenzylamine (0.26 g) and N,N-diisopropylethylamine (0.37 mL) were suspended in n-propanol (3.6 mL), and the mixture was refluxed for 43 hours. The reaction mixture was concentrated under reduced pressure, and the obtained residue was purified by column chromatography on aminopropylated silica gel (dichloromethane/methanol=12/1) to give the title compound (0.15 g).

¹H-NMR (DMSO-d₆) δ ppm: 3.63-3.85 (3H, m), 4.05-4.29 (2H, m), 4.48-4.72 (2H, m), 5.18-5.72 (3H, m), 6.16 (1H, d, J=5.4 Hz), 6.78-6.97 (2H, m), 7.06-7.72 (12H, m)

EXAMPLE 108

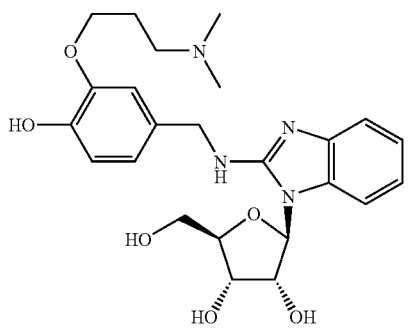

2-[4-Hydroxy-3-(3-dimethylaminopropoxy)benzylamino]-1-(β-D-ribofuranosyl)-1H-benzimidazole 2-[4-Benzyloxy-3-(3-chloropropoxy)benzylamino]-1-(2,3,5-tri-O-acetyl-β-D-ribofuranosyl)-1H-benzimidazole (0.05 g) and sodium iodide (0.01 g) were suspended in acetone (15 mL), and the mixture was refluxed for 16 hours. The insoluble material was removed by filtration, and the filtrate was concentrated under reduced pressure. The obtained residue and dimethylamine (0.03 g) were suspended in a mixed solvent of ethanol (1 mL) and acetonitrile (1 mL), and the mixture was stirred at 75° C. for 24 hours. The insoluble material was removed by filtration, and the filtrate was concentrated under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give 2-[4-benzyloxy-3-(3-dimethylaminopropoxy)benzylamino]-1-(β-D-ribofuranosyl)-1H-benzimidazole. The obtained compound was dissolved in methanol (2 mL). To the solution was added a catalytic amount of 10% palladium-carbon powder, and the mixture was stirred at 40° C. under a hydrogen atmosphere for 24 hour. The insoluble material was removed by filtration, and the filtrate was concentrated under reduced pressure to give the title compound (0.02 g).

¹H-NMR (DMSO-d₆) δ ppm: 1.75-1.90 (2H, m), 2.15 (6H, s), 2.40 (2H, t, J=6.7 Hz), 3.60-3.75 (2H, m), 3.85-4.15 (4H, m), 4.25-4.53 (3H, m), 5.78 (1H, d, J=7.7 Hz), 6.65-7.05 (5H, m), 7.10-7.35 (3H, m)

EXAMPLE 109

The compounds of Table 24 can be prepared in a similar manner to that described in Example 108 using the corresponding materials.

TABLE 24

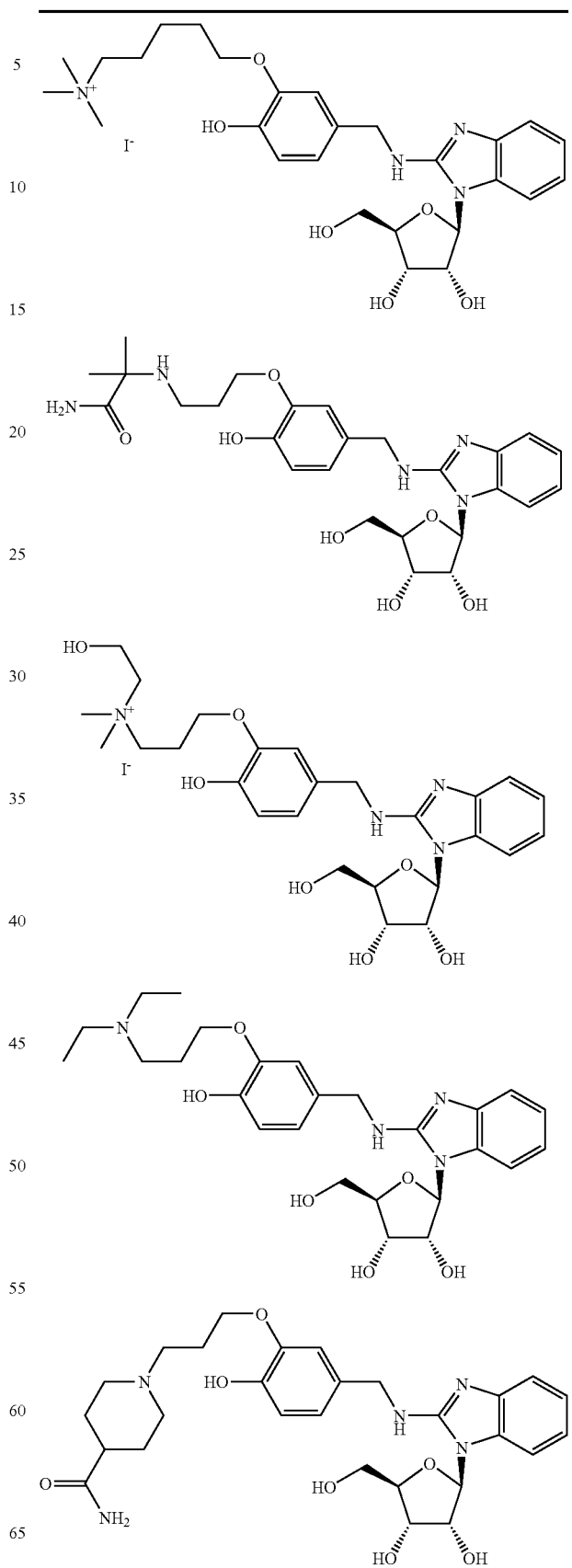

TABLE 24-continued

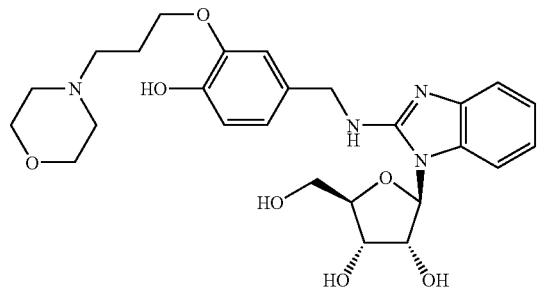

EXAMPLE 110

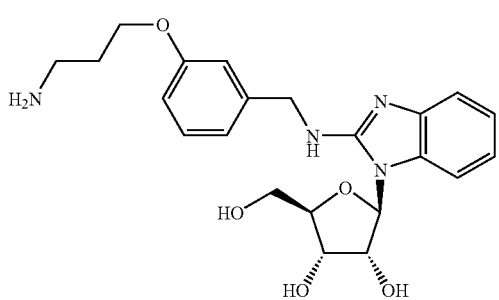

2-[3-(3-Aminopropoxy)benzylamino]-1-(β-D-ribofuranosyl)-1H-benzimidazole 2-(3-Hydroxybenzylamino)-1-(β-D-ribofuranosyl)-1H-benzimidazole (0.77 g) and potassium carbonate (0.43 g) were suspended in N,N-dimethylformamide (15 mL). To the mixture was added N-(3-bromopropy)phthalimide (0.84 g), and the mixture was stirred at 60° C. for 16 hours. The insoluble material was removed by filtration, and the reaction mixture was concentrated under reduced pressure. The obtained residue was purified by column chromatography on silica gel (ethyl acetate/ethanol=10/1) to give 2-[3-(3-phthalimidepropoxy)benzylamino]-1-(β-D-ribofuranosyl)-1H-benzimidazole (0.75 g). The obtained compound was dissolved in methanol (5 mL). To the reaction mixture was added hydrazine monohydrate (0.5 mL), and the mixture was stirred at 90° C. for 6 hours. The solvent was removed under reduced pressure, and the obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (0.50 g).

$^1$H-NMR (DMSO-$d_6$) δ ppm: 1.65-1.90 (2H, m), 2.69 (2H, t, J=6.7 Hz), 3.60-3.76 (2H, m), 3.85-4.20 (4H, m), 4.33-4.46 (1H, m), 4.53 (2H, d, J=5.8 Hz), 5.83 (1H, d, J=7.7 Hz), 6.70-7.55 (9H, m)

EXAMPLE 111

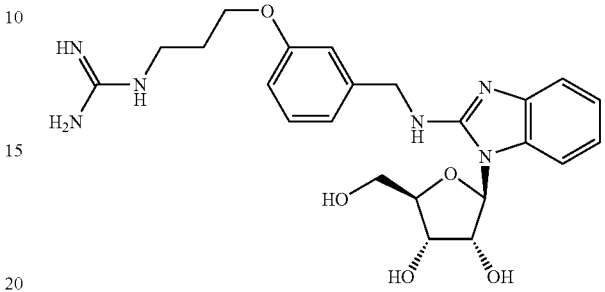

2-[3-(3-Guanidinopropoxy)benzylamino]-1-(β-D-ribofuranosyl)-1H-benzimidazole

2-[3-(3-Aminopropoxy)benzylamino]-1-(β-D-ribofuranosyl)-1H-benzimidazole (0.2 g) and N-(benzyloxycarbonyl)-1H-pyrazol-1-carboxamidine (0.55 g) were suspended in tetrahydrofuran (2.5 mL), and the mixture was stirred at 60° C. for 24 hours. The reaction mixture was concentrated under reduced pressure, and the obtained residue was dissolved in methanol (4 mL). To the solution was added a catalytic amount of 10% palladium-carbon powder, and the mixture was stirred at 40° C. under a hydrogen atmosphere for 2 hour. The insoluble material was removed by filtration, and the filtrate was concentrated under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (0.01 g).

$^1$H-NMR (CD$_3$OD) δ ppm: 1.95-2.05 (2H, m), 3.80-3.85 (2H, m), 4.00-4.30 (4H, m), 4.55-4.65 (3H, m), 5.45-5.55 (2H, m), 5.95 (1H, d, J=7.4 Hz), 6.75-6.85 (1H, m), 6.90-7.10 (4H, m), 7.15-7.30 (3H, m)

EXAMPLE 112

The compounds of Table 25 can be prepared in a similar manner to that described in Example 111 using the corresponding materials.

TABLE 25

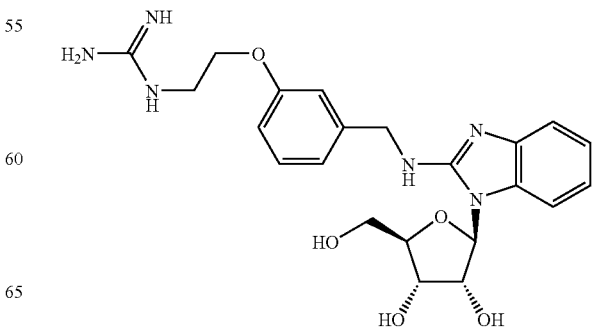

TABLE 25-continued

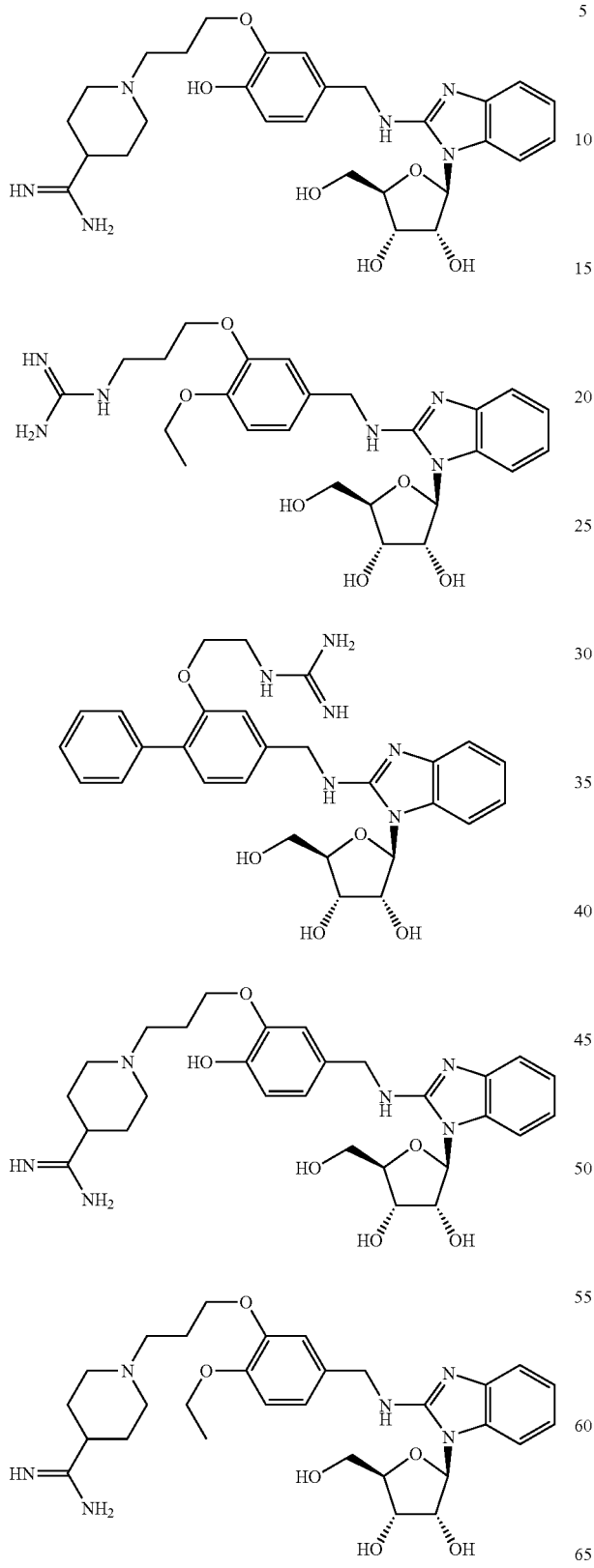

EXAMPLE 113

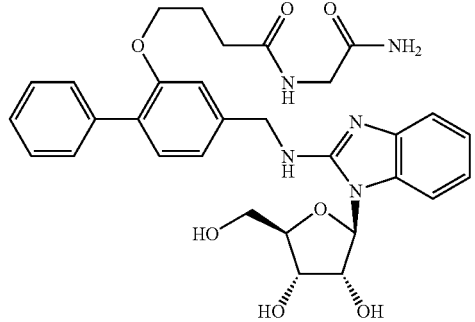

2-{3-[3-(Carbamoylmethylcarbamoyl)propoxy]-4-phenylbenzylamino}-1-(β-D-ribofuranosyl)-1H-benzimidazole 2-[3-(3-Carboxypropoxy)-4-phenylbenzylamino]-1-(β-D-ribofuranosyl)-1H-benzimidazole (50 mg), glycinamide hydrochloride (17 mg), 1-hydroxybenzotriazole (29 mg) and triethylamine (47 mg) were suspended in N,N-dimethylformamide (2 mL) at room temperature. To the mixture was added 1-ethyl-3-(3-dimethylaminopropyl)carbodiimide hydrochloride (36 mg), and the mixture was stirred at room temperature for 17 hours. The reaction mixture was concentrated under reduced pressure, and the obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (23 mg).

$^1$H-NMR (CD$_3$OD) δ ppm: 1.90-2.05 (2H, m), 2.25-2.40 (2H, m), 3.75 (2H, s), 3.80-3.90 (2H, m), 3.95-4.05 (2H, m), 4.10-4.35 (2H, m), 5.97 (1H, d, J=7.2 Hz), 6.90-7.55 (12H, m)

EXAMPLES 114-115

The compounds of Table 26 were prepared in a similar manner to that described in Example 113 using the corresponding materials.

TABLE 26

| Example No. | Structure | $^1$H-NMR δ ppm |
|---|---|---|
| Example 114 | 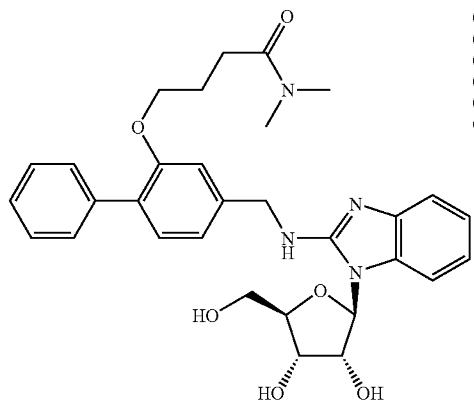 | (CD$_3$OD) 1.85-2.05 (2 H, m), 2.25-2.40 (2 H, m), 2.80 (3 H, s), 2.82 (3 H, s), 3.75-3.90 (2 H, m), 3.95-4.05 (2 H, m), 4.10-4.20 (1 H, m), 4.25-4.35 (1 H, m), 4.50-4.80 (3 H, m), 5.98 (1 H, d, J = 7.4 Hz), 6.95-7.55 (12 H, m) |
| Example 115 | 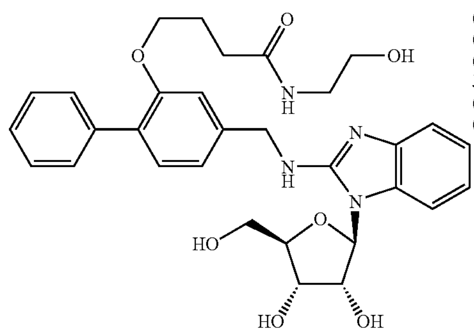 | (CD$_3$OD) 1.85-2.05 (2 H, m), 2.20-2.30 (2 H, m), 3.15-3.25 (2 H, m), 3.45-3.60 (2 H, m), 3.75-3.90 (2 H, m), 3.98 (2 H, t, J = 6.2 Hz), 4.10-4.35 (2 H, m), 4.55-4.75 (3 H, m), 5.98 (1 H, d, J = 7.6 Hz), 6.85-7.55 (12 H, m) |

EXAMPLE 116

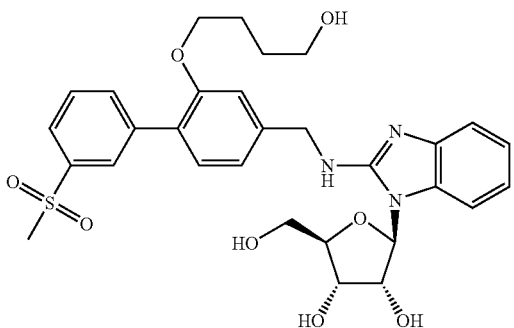

2-[3-(4-Hydroxybutoxy)-4-(3-methanesulfonylphenyl)benzylamino]-1-(β-D-ribofuranosyl)-1H-benzimidazole 2-Amino-1-(2,3,5-tri-O-acetyl-β-D-ribofuranosyl)-1H-benzimidazole (0.11 g) and 3-(4-benzyloxybutoxy)-4-(3-methanesulfonylphenyl)benzaldehyde (0.24 g) were suspended in tetrahydrofuran (5 mL). To the reaction mixture was added sodium triacetoxyborohydride (0.12 g), and the mixture was stirred at room temperature for 24 hours. After adding water to the reaction mixture, the mixture was concentrated under reduced pressure. The obtained residue was dissolved in methanol (2 mL). To the mixture was added 5 mol/L aqueous sodium hydroxide solution (0.5 mL), and the mixture was stirred at room temperature for 1 hour. To the reaction mixture was added acetic acid (1 mL), and the mixture was concentrated under reduced pressure. The obtained residue was purified by preparative reverse phase column chromatography (Shiseido CAPSELL PAC C18UG80, 5 μm, 20×50 mm, flow rate 30 mL/minutes linear gradient, water/methanol=70/30-10/90) to give 2-[3-(4-benzyloxybutoxy)-4-(3-methanesulfonylphenyl)benzylamino]-1-(β-D-ribofuranosyl)-1H-benzimidazole (0.16 g). The obtained compound was dissolved in methanol (2 mL). To the solution was added a catalytic amount of 10% palladium-carbon powder, and the mixture was stirred at 40° C. under a hydrogen atmosphere for 24 hour. The insoluble material was removed by filtration, and the filtrate was concentrated under reduced pressure to give the title compound (0.04 g).

$^1$H-NMR (CD$_3$OD) δ ppm: 1.50-1.85 (4H, m), 3.12 (3H, s), 3.50 (2H, t, J=6.5 Hz), 3.77-3.90 (2H, m), 4.04 (2H, t, J=6.1 Hz), 4.10-4.35 (2H, m), 4.55-4.80 (3H, m), 5.98 (1H, d, J=7.7 Hz), 6.94-7.40 (7H, m), 7.55-7.70 (1H, m), 7.75-7.95 (1H, m), 8.13 (1H, s)

TEST EXAMPLE 1

Human CNT1 cDNA Cloning

Human CNT1 cDNA was obtained by PCR amplification of human kidney cDNA (Origene). PCR reaction solution contained 1 μL cDNA, 2 units Platinum taq DNA polymerase high fidelity (Invitrogen), 1 μM primers (Forward: 5'-TGC ACT GCA TGG TTG CTG CT-3', Reverse: 5'-GTC TAA GTC CTG TGG CTT CC-3'). Amplifications for 1 cycle at 94° C. for 2 minutes and 32 cycles at 94° C. for 30 seconds, 58° C. for 30 seconds and 68° C. for 3 minutes were performed and PCR products were ligated into PCR-II-TOPO vector (Invitrogen). The amino acid sequence of cloned human CNT1 was substituted at G34E (codon, GGA to GAA), Q462R (codon, CAG to CGG) and R511C (codon, CGC to TGC) compared to a reported amino acid sequence for human CNT1 (NCBI Accession No. AAB53837.1).

TEST EXAMPLE 2

Human CNT2 cDNA Cloning and Construction of Expression Plasmid

Human CNT2 cDNA was obtained by PCR amplification of human kidney cDNA (CLONTECH). PCR reaction solution contained 1 μL cDNA, 2 units Platinum taq DNA polymerase high fidelity (Invitrogen), 1 μM primers (Forward: 5'-AGG AGC CAG AGG GAA TCA AT-3', Reverse: 5'-ACA TCT TGG TGA GTG AGT TG-3'). Amplifications for 1 cycle at 94° C. for 2 minutes, 32 cycles at 94° C. for 30 seconds, 58° C. for 30 seconds and 68° C. for 3 minutes were performed and PCR products were ligated into PCR-II-TOPO vector (Invitrogen). PCR reaction was performed with primers containing restriction enzyme sites and the constructed plasmid as a template. PCR reaction solution contained 100 ng plasmid, 2 units Pyrobest DNA polymerase (Takara), 330 nM primers (Forward: 5'-CCG CTC GAG AGG AGC CAG AGG GAA TCA AT-3', Reverse: 5'-CGT CTA GAA CAT CTT GGT GAG TGA GTT G-3'). Amplifications for 1 cycle at 95° C. for 3 minutes, 15 cycles at 98° C. for 10 seconds, 60° C. for 30 seconds and 72° C. for 1 minute and 1 cycle at 72° C. for 7 minutes were performed, and the PCR products were ligated into PCI-neo mammalian expression vector (Promega). The amino acid sequence of cloned human CNT2 was substituted at P22L (codon, CCG to CTG), S45C (codon, AGC to TGC) and I160M (codon, ATA to ATG) compared to a reported amino acid sequence for human CNT2 (NCBI Accession No. AAC51930).

TEST EXAMPLE 3

Human CNT3 cDNA Cloning

Human CNT3 cDNA was obtained by PCR amplification of human small intestine cDNA (CLONTECH). PCR reaction solution contained 0.2 μL cDNA, Expand long template PCR system (Roche), 0.5 μM primers (Forward: 5'-GCC AGC CAG CAG CAA AAA-3', Reverse: 5'-TGG AGA AGT GGC TGA CCT-3'). Amplifications for 1 cycle at 94° C. for 2 minutes and 33 cycles at 94° C. for 10 seconds, 58° C. for 30 seconds and 68° C. for 2 minutes were performed, and PCR products were ligated into PCR-II-TOPO vector (Invitrogen). Nucleotide sequence of cloned human CNT3 was identical to a reported nucleotide sequence for human CNT3 (NCBI Accession No. NM022127) from position 1130 to 1215.

TEST EXAMPLE 4

Distribution Pattern of Human CNTs in Human Tissues

1) Synthesis of cDNA

Total RNAs derived from human liver, colon, testis, pancreas, lung, small intestine, stomach, placenta and muscle were purchased from Sawady Technology, and total RNAs of trachea, brain, kidney and heart were purchased from CLONTECH. Total RNA concentration was determined by RiboGreen RNA quantification reagent and kit (Molecular Probe). cDNAs were synthesized (reverse transcription). A reaction solution (16.5 μL) contained 1.5 μg total RNA and 1.5 μL random hexamer at 500 ng/μL (Invitrogen). The reaction solution was incubated at 70° C. for 5 minutes, then at room temperature for 5 minutes. A reaction solution (13.5 μL) containing 6 μL 5×BRL 1st strand buffer (Invitrogen), 3.25 μL distilled water (Nippongene), 1.5 μL of 10 mM dNTP mix (Invitrogen), 0.75 μL RNase inhibitor (Invitrogen) and 2 μL Superscript II (Invitrogen) was added to the reaction solution described above. Another reaction solution containing distilled water (Nippongene) instead of Superscript II was also added to the solution described above. After all mixtures were incubated at room temperature for 10 minutes and 42° C. for 1 hour. To inactivate Superscript II, and the resulting solutions were incubated at 95° C. for 10 minutes and transferred to ice immediately. Next, 1.5 μL of RNase H (Invitrogen) was added and the solutions were incubated at 37° C. for 30 minutes. At the end of the reaction, 170 μL of distilled water was added. The synthesized cDNAs were extracted with 200 μL of a mixture (phenol:chloroform:isoamylalcohol=25:24:1) (Invitrogen) and furthermore extracted with 200 μL of a mixture (chloroform:isoamylalcohol=24:1). After ethanol precipitation, cDNAs were dissolved in distilled water (Nippongene).

2) Determination of Human CNTs Gene Expression by Quantitative Real-Time PCR

For human CNT1 in quantitative real-time PCR, forward: 5'-ATT TAC CAG TGC TGC CGT GAG-3' and reverse: 5'-AAA CCG ACA GCA GTT GTC CAG-3' as primers and 5'-AGA GCG TCA ATC CAG AGT TCA GCC CA-3' as a probe were used. For human CNT2, forward: 5'-GGC AGC TTG CAT CTT GAA TTT C-3' and reverse: 5'-CAA AAA CGA GTC AAC CAG GAC A-3' as primers and 5'-CCT TGT TTG TCA TCA CCT GCT TGG TGA TCT-3' as a probe were used. Probes were labeled with fluorescence dye, FAM at 5' terminal and TAMRA at 3' terminal. A reaction solution (25 μL) contained 2.5 ng cDNA synthesized above, 1×Taqman Universal master mix (Applied Biosystems), 500 nM forward and reverse primers and 200 nM probe. PCR protocol was as follows. One cycle at 50° C. for 2 minutes, 1 cycle at 95° C. for 10 minutes and 40 cycles at 95° C. for 15 seconds and at 60° C. for 1 minute. Assays were performed using GeneAmp 5500 Sequence detection system (Applied Biosystems), MicroAmp optical 96-well reaction plates (Applied Biosystems) and MicroAmp optical caps (Applied Biosystems) Signals were detected according to manufacturer's instruction (See Genome Research, 1996, vol. 6, pp. 986-994). Samples were analyzed with serially (1:10) diluted plasmid DNAs as standard curve. As shown in FIG. 1, human CNT1 was expressed in kidney and liver abundantly, on the other hand, human CNT2 was expressed in small intestine and stomach abundantly.

TEST EXAMPLE 5

Distribution Pattern of Human CNTs in Stomach and Intestine

Determination of Human CNTs Gene Expression by Quantitative Real-Time PCR

Figure 2:
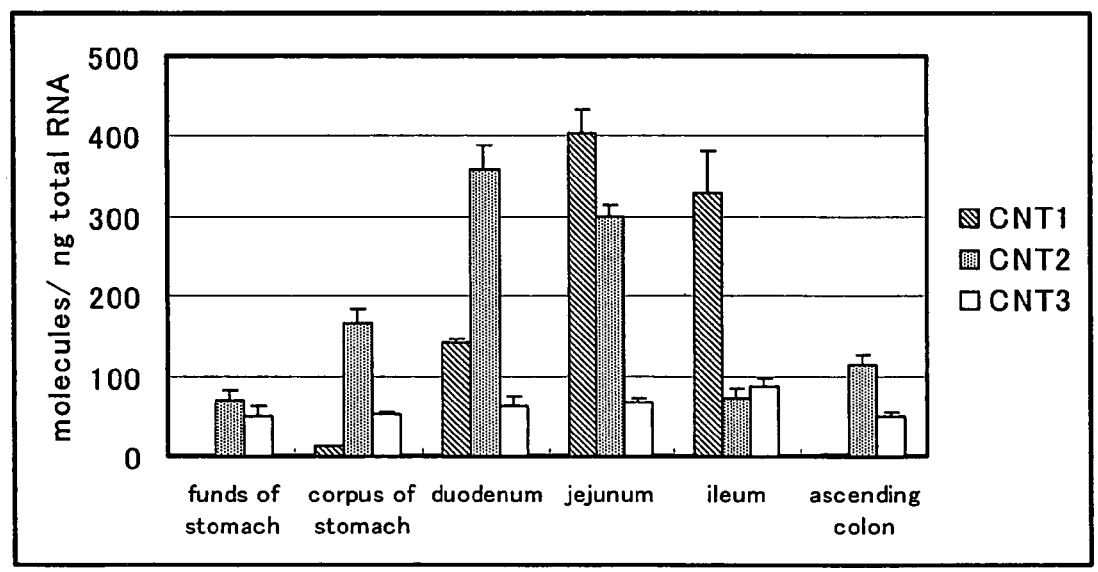

Total RNAs derived from funds of stomach, corpus of stomach, duodenum, jejunum, ileum and ascending colon were purchased from BIOCHAIN. Total RNA concentration was determined by RiboGreen RNA quantification reagent and kit (Molecular Probe). Primers and probes for human CNT1, 2 were the same in Test Example 4. For human CNT3, forward: 5'-GCT GGT CCG ACC ATA TTT ACC TTA C-3' and reverse: 5'-CGC TTC CAG CAA TGG TAG AGA-3' as primers and 5'-TCA CCA AGT CTG AAC TCC ACG CCA TC-3' as a probe were used. Probe was labeled with fluorescence dye, FAM at 5' terminal and TAMRA at 3' terminal. Reaction solution (25 µL) contained Taqman EZ RT-PCR kit (Applied Biosystems), 500 nM forward and reverse primer and 200 nM probe. PCR protocol was as follows. One cycle at 50° C. for 2 minutes, 1 cycle at 60° C. for 30 minutes, 1 cycle at 95° C. for 5 minutes and 40 cycles at 94° C. for 20 seconds and at 62° C. for 1 minute. Assays were performed using DNA Engine Opticon (MJ Japan) and 96 well low multiple plates (MJ Japan). Signals were detected according to manufacturer's instruction (See Genome Research, 1996, vol. 6, pp. 986-994). Samples were analyzed with serially (1:10) diluted plasmid DNAs as standard curve. As shown in FIG. 2, human CNT1 was expressed in jejunum and ileum strongly. On the other hand, human CNT2 was expressed in duodenum and jejunum strongly, and CNT2 was also expressed in stomach and colon weakly. Human CNT3 was expressed weakly in all tissues.

TEST EXAMPLE 6

Preparation of Cells Transiently Expressing Human CNT2

Expression plasmid of human CNT2 was transfected into COS-7 cells (RIKEN CELL BANK RCB0539) by lipofection method. LIPOFECTAMINE 2000 (Invitrogen) was used as a lipofection reagent. COS-7 cells were diluted in D-MEM (Invitrogen) containing 10% fetal calf serum (Sanko Junyaku) at $5 \times 10^5$/1 mL, and seeded into collagen-coated 96-well plates (IWAKI) at 100 µL/well and cultured at 37° C. for 2 hours with 5% $CO_2$ condition. For each well, 0.6 µL of LIPOFECTAMINE 2000 (Invitrogen) was diluted in 25 µL of OPTI-MEM (Invitrogen), and incubated for 7 minutes at room temperature (hereinafter referred to as Lipo 2000-OPTI). For each well, 0.3 µg of plasmid was diluted in 25 µL of OPTI-MEM (Invitrogen), and the solution was added to the Lipo 2000-OPTI and mixed gently and incubated for 30 minutes at room temperature, and was transferred 50 µL for each well to culture medium. The cells were incubated at 37° C. with 5% $CO_2$ condition for 2 days, and used for the uptake assays.

TEST EXAMPLE 7

Measurement of Inhibitory Activity Against Uptake of Adenosine Through Human CNT2

An Uptake buffer was prepared by addition of a mixture of non-radioisotope labeled (Sigma) and $^{14}C$-labeled (Amersham Biosciences) adenosine at the final concentration of 10 µM into a buffer, pH 7.4, containing 140 mM sodium chloride, 2 mM potassium chloride, 1 mM calcium chloride, 1 mM magnesium chloride, 10 mM HEPES 2-[4-(2-hydroxyethyl)-1-piperazinyl]ethane sulfonic acid, 5 mM tris(hydroxymethyl)aminomethane and 5 mM glucose. For measurement of basal uptake, Basal uptake measurement buffer, which contained 140 mM choline chloride instead of sodium chloride was prepared. In uptake assays, NBMPR was added to Uptake buffer and Basal uptake measurement buffer at the final concentration of 10 µM. In the case of measurement of inhibitory activity of test compounds, test compounds were dissolved in dimethyl sulfoxide, and then appropriately diluted with Uptake buffer as to prepare Measurement buffers. After removing culture medium of human CNT2 transiently expressing cells, Pretreatment buffer (Basal uptake measurement buffer without adenosine and glucose) was added to wells at 200 µL/well and incubated at 37° C. for 10 minutes. After repeating the same step again, Pretreatment buffer was removed and Measurement buffers and Basal uptake measurement buffer were added at 75 µL/well and incubated at 37° C. After incubation for 30 minutes, Measurement buffers and Basal uptake measurement buffer were removed, and the cells were washed with Washing buffer (Basal uptake measurement buffer with non-radioisotope labeled adenosine at 10 µM) at 200 µL/well twice. The cells were solubilized with 0.2 mol/L sodium hydroxide at 75 µL/well, and the cell lysates were transferred into PicoPlates (Perkin Elmer). After mixing with 150 µL of MicroScint-40 (Perkin Elmer), radioactivity was measured by means of scintillation counter (Perkin Elmer). One hundred % was set to the difference between the uptake in the control group and the basal uptake, and the uptake of adenosine at each test compound concentration was calculated. The test compound concentration inhibiting 50% uptake of adenosine ($IC_{50}$ value) was calculated using logit plot. The results are shown in Table 27.

TABLE 27

| Test compound | $IC_{50}$ (nM) |
| --- | --- |
| Example 28 | 46 |
| Example 34 | 104 |
| Example 51 | 9 |
| Example 36 | 150 |
| Example 37 | 213 |
| Example 89 | 55 |
| Example 90 | 184 |
| Example 93 | 172 |

TEST EXAMPLE 8

Effects of CNT2 Inhibitors on Plasma Uric Acid Level

Male SD-IGS rats (5 weeks old) which were fasted overnight, were subcutaneously treated with oxonic acid (Aldrich; 100 mg/kg), and after 1 hour, purine mix (Adenosine:Inosine:Guanosine=1:1:1 (Adenosine (Sigma), Inosine (WAKO), Guanosine (ICN); 50 mg/kg) and test compounds (10 mg/kg) were orally administered simultaneously. A control group was treated with oxonic acid and the purine mix, and a group administrated only oxonic acid represented endogenous plasma uric acid value. After 1 hour, blood was collected from the abdominal aorta under ether anesthesia, and the plasma was collected with Venoject II vacuum blood collecting tube (Terumo, VP-FH052). According to the method described in Journal of Chromatography B, Vol. 744 (2000), pp. 129-138, plasma uric acid level in a compound of Example 28 was measured by using HPLC method mentioned below. Plasma uric acid levels in compounds of Examples 89 and 90 were measured by phosphotungstic acid method. Uric acid-Test Wako (WAKO) was used as a measurement reagent. As there is no difference of uric acid values between the HPLC method and the phosphotungstic acid method, uric acid value can be measured by either of both methods (for example, see the above Management guideline, pp. 18-19). The difference between plasma uric acid value in each study group and endogenous plasma uric acid value was calculated on the basis of 100% in the control group. The results are shown in Table 28.

TABLE 28

| Test compound | Percentage of increment of plasma uric acid level (%) |
|---|---|
| Example 28 | 15.2% ($p < 0.01$) |
| Example 89 | 24.9% ($p < 0.01$) |
| Example 90 | 45.6% ($p < 0.05$) |

Determination of Plasma Uric Acid Level by High-Performance Liquid Chromatography (HPLC)

Theophylline (10 μg) as an internal standard substance was added to 0.1 mL of plasma collected with the above method, and then the samples were deproteinized with 1 mL of methanol. After the samples were centrifuged, the methanol layers were evaporated to dryness under a stream of nitrogen. The residues were dissolved in 300 μL of mobile phase, and 40 μL of the portion was injected into HPLC. Plasma uric acid concentration was determined by HPLC method according to the condition described below. Calibration curves were constructed by addition of theophylline as an internal standard substance and several concentrations of uric acid to 0.1 mL of distilled water appropriately.

HPLC Analytical Condition
    Column: Inertsil ODS-2 (4.6×250 mm)
    Mobile phase
        A solution: acetonitrile
        B solution: 10 mM phosphate buffer (pH 3.0)
    A linear gradient elution method: A solution 2% to A solution 22% (25 minutes)
    Column temperature: 40° C.
    Flow rate: 0.5 mL/minute
    Detection absorbance: 284 nm

INDUSTRIAL APPLICABILITY

The benzimidazole derivatives represented by the above general formula (I) of the present invention or pharmaceutically acceptable salt thereof, or a prodrug thereof exert an excellent CNT2 inhibitory activity and can markedly inhibit the elevation of plasma uric acid level. Therefore, they are useful as agents for the prevention or treatment of diseases associated with an abnormality of plasma uric acid level.

[Sequence Listing Free Text]
Sequence Number 1: Synthetic DNA primer
Sequence Number 2: Synthetic DNA primer
Sequence Number 3: Synthetic DNA primer
Sequence Number 4: Synthetic DNA primer
Sequence Number 5: Synthetic DNA primer
Sequence Number 6: Synthetic DNA primer
Sequence Number 7: Synthetic DNA primer
Sequence Number 8: Synthetic DNA primer
Sequence Number 9: Synthetic DNA primer
Sequence Number 10: Synthetic DNA primer
Sequence Number 11: Synthetic DNA probe
Sequence Number 12: Synthetic DNA primer
Sequence Number 13: Synthetic DNA primer
Sequence Number 14: Synthetic DNA probe
Sequence Number 15: Synthetic DNA primer
Sequence Number 16: Synthetic DNA primer
Sequence Number 17: Synthetic DNA probe

What is claimed is:

1. A benzimidazole derivative represented by the general formula:

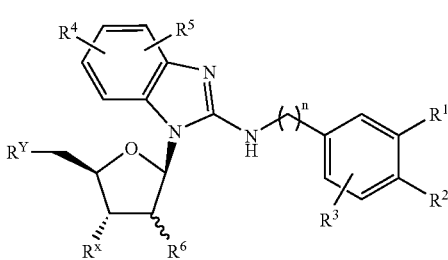

wherein n represents 1 or 2;

$R^1$ and $R^2$ independently represents a hydrogen atom, a halogen atom, a cyano group, any of the following substituents (A) to (C) which may have the same or different 1 to 3 groups selected from a substituent group α, any of the following substituents (D) to (G) which may have the same or different 1 to 3 groups selected from a substituent groups α and β, or any of the following substituents (H) to (M);

$R^3$ represents a hydrogen atom, a halogen atom, any of the following substituents (A) to (C) which may have the same or different 1 to 3 groups selected from a substituent group α, or any of the following substituents (H) to (M);

(A) a $C_{1-6}$ alkyl group;
(B) a $C_{2-6}$ alkenyl group;
(C) a $C_{2-6}$ alkynyl group;
(D) a $C_{3-8}$ cycloalkyl group;
(E) a 3 to 10-membered cyclic heterocycloalkyl group;
(F) a $C_{6-10}$ aryl group;
(G) a 5 to 10-membered cyclic heteroaryl group;
(H) $OR^7$;
(I) $SR^8$;
(J) $NR^9R^{10}$;
(K) $COOR^{11}$;
(L) $CONR^{12}R^{13}$;
(M) $NHCOR^{14}$ in which $R^7$ to $R^{14}$ independently represents a hydrogen atom, or any of the following substituents (N) to (P) which may have the same or different 1 to 3 groups selected from a substituent group α, or any of the following substituents (Q) to (V) which may have the same or different 1 to 3 groups selected from substituent groups α and β

(N) a $C_{1-6}$ alkyl group;
(O) a $C_{2-6}$ alkenyl group;
(P) a $C_{2-6}$ alkynyl group;
(Q) a $C_{3-8}$ cycloalkyl group;
(R) a 3 to 10-membered cyclic heterocycloalkyl group;
(S) a quaternary salt of a 3 to 10-membered cyclic nitrogen-containing heterocycloalkyl group;
(T) a $C_{6-10}$ aryl group;
(U) a 5 to 10-membered cyclic heteroaryl group;
(V) a quaternary salt of a 5 to 10-membered cyclic nitrogen-containing heteroaryl group;

$R^4$ and $R^5$ independently represent a hydrogen atom, a hydroxy group, a $C_{1-6}$ alkyl group or $C_{1-6}$ alkoxy group;

$R^6$ and $R^x$ independently represent a hydrogen atom or a hydroxy group;

$R^Y$ represents a fluorine atom or a hydroxy group, and with the proviso that at least one of $R^1$, $R^2$ and $R^3$ does not represent a group selected from a hydrogen atom, a halogen atom, a hydroxy group, a $C_{1-6}$ alkoxy group, $NH_2$ and COOH wherein Substituent group α is:
wherein Substituent group α is:

(a) a halogen atom;
(b) a cyano group;

any of the following substituents (c) to (h) which may have the same or different 1 to 3 groups selected from a substituent group γ, or any of the following substituents (i) to (v):

(c) a $C_{3-8}$ cycloalkyl group;
(d) a 3 to 10-membered cyclic heterocycloalkyl group;
(e) a quaternary salt of a 3 to 10-membered cyclic nitrogen-containing heterocycloalkyl group;
(f) a $C_{6-10}$ aryl group;
(g) a 5 to 10-membered cyclic heteroaryl group;
(h) a quaternary salt of a 5 to 10-membered cyclic nitrogen-containing heteroaryl group;
(i) $OR^{15}$;
(j) $SR^{16}$;
(k) $NR^{17}R^{18}$;
(l) $N^+R^DR^ER^F$;
(m) $COOR^{19}$;
(o) $NHCOR^{20}$;
(p) $NHC(=NH)-NH_2$;
(q) $C(=NH)-NH_2$ (which is bound to a nitrogen atom of a nitrogen-containing heterocycloalkyl group);
(r) $NR^{21}CONR^{22}R^{23}$;
(s) $NR^GSO_2R^H$;
(t) $SO_2R^1$ ($R^1$ represents a $C_{1-6}$ alkyl group, a $C_{2-6}$ alkenylene group or a hydroxyl ($C_{1-6}$ alkyl) group);
(u) $CONR^{24}R^{25}$;
(v) $SO_2NR^{26}R^{27}$ in which $R^{D-F}$ independently represent any of the following substituents (y1) to (y11) which may have the same or different 1 to 3 groups selected from a substituent group γ;

$R^{15}$, $R^{16}$, $R^{19-21}$ and $R^{G-H}$ independently represent a hydrogen atom, or any of the following substituents (y1) to (y11) which may have the same or different 1 to 3 groups selected from a substituent group γ; $R^{17}$, $R^{18}$ and $R^{22}$ to $R^{27}$ independently represent a hydrogen atom, or any of the following substituents (y1) to (y11) which may have the same or different 1 to 3 groups selected from a substituent group γ; or $R^{17}$ and $R^{18}$, $R^{22}$ and $R^{23}$, $R^{24}$ and $R^{25}$, and $R^{26}$ and $R^{27}$ independently may bind together with the neighboring nitrogen atom to form a 3 to 8-membered aliphatic cyclic amino group (y1) a $C_{1-6}$ alkyl group;
(y2) a $C_{2-6}$ alkenyl group;
(y3) a $C_{2-6}$ alkynyl group;
(y4) a $C_{3-8}$ cycloalkyl group;
(y5) a 3 to 10-membered cyclic heterocycloalkyl group;
(y6) a $C_{6-10}$ aryl group;
(y7) a 5 to 10-membered cyclic heteroaryl group;
(y8) a $C_{3-8}$ cycloalkyl-$C_{1-6}$ alkyl group;
(y9) a 3 to 10-membered cyclic heterocycloalkyl-$C_{1-6}$ alkyl group;
(y10) a $C_{6-10}$ aryl-$C_{1-6}$ alkyl group;
(y11) a 5 to 10-membered cyclic heteroaryl-$C_{1-6}$ alkyl group wherein Substituent group β is:
any of the following substituents (z1) to (z3) which may have the same or different 1 to 3 groups selected from a substituent group γ; substituent group γ:
(z1) a $C_{1-6}$ alkyl group;
(z2) a $C_{2-6}$ alkenyl group;
(z3) a $C_{2-6}$ alkynyl group wherein Substituent group γ is:
(1) a halogen atom;
(2) a nitro group;
(3) a cyano group;
(4) $OR^{28}$;
(5) $SR^{29}$;
(6) $NR^{30}R^{J}$ wherein $R^{30}$ and $R^{J}$ independently represent a hydrogen atom, a $C_{1-6}$ alkyl group, a $C_{2-6}$ alkenyl group, a hydroxy($C_{1-6}$ alkyl) group, a $C_{6-10}$ aryl-$C_{1-6}$ alkyl group or a $C_{6-10}$ aryl group;
(7) $N^{+}R^{K}R^{L}R^{M}$ wherein $R^{K-M}$ independently represent a $C_{1-6}$ alkyl group, a $C_{2-6}$ alkenyl group, a hydroxy($C_{1-6}$ alkyl) group, a $C_{6-10}$ aryl-$C_{1-6}$ alkyl group or a $C_{6-10}$ aryl group);
(8) $COR^{31}$;
(9) $COOR^{32}$;
(10) $OCOR^{33}$;
(11) $NHCOR^{34}$;
(12) NHC(=NH)—$NH_2$;
(13) C(=NH)—$NH_2$ which is bound to a nitrogen atom of a heterocycloalkyl group
(14) $NR^{35}CONR^{36}R^{37}$;
(15) $NR^{N}COOR^{O}$;
(16) $CONR^{38}R^{39}$;
(17) $SO_2NR^{40}R^{41}$;
(18) a hydroxy($C_{2-6}$ alkyl) group;
(19) a 5 to 10-membered cyclic nitrogen-containing heteroaryl group wherein $R^{28}$, $R^{29}$, $R^{31-35}$, $R^{N}$ and $R^{O}$ independently represent a hydrogen atom, a $C_{1-6}$ alkyl group or a $C_{6-10}$ aryl-$C_{1-6}$ alkyl group; $R^{36}$ to $R^{41}$ independently represent a hydrogen atom, or a $C_{1-6}$ alkyl group, or $R^{36}$ and $R^{37}$, $R^{38}$ and $R^{39}$, and $R^{40}$ and $R^{41}$ independently may bind together with the neighboring nitrogen atom to form a 3 to 8-membered aliphatic cyclic amino group, or a pharmaceutically acceptable salt thereof, or a prodrug thereof.

2. A benzimidazole derivative as claimed in claim 1 wherein n represents 1, or a pharmaceutically acceptable salt thereof, or a prodrug thereof.

3. A benzimidazole derivative as claimed in claim 1 or 2 wherein $R^{Y}$ represents a hydroxy group, or a pharmaceutically acceptable salt thereof, or a prodrug thereof.

4. A benzimidazole derivative as claimed in claim 1 wherein $R^{1}$ and $R^{3}$ independently represent a hydrogen atom, a halogen atom, any of the substituents (A) to (C) which may have the same or different 1 to 3 groups selected from the substituent group α, or any of the substituents (H) to (M), $R^{2}$ independently represents a hydrogen atom, a halogen atom, a cyano group, any of the substituents (A) to (C) which may have the same or different 1 to 3 groups selected from the substituent group α, any of the substituents (D) to (G) which may have the same or different 1 to 3 groups selected from the substituent groups α and β, or any of the substituents (H) to (M), or a pharmaceutically acceptable salt thereof, or a prodrug thereof.

5. A benzimidazole derivative as claimed in claims 1, 2 or 4 wherein the substituent:

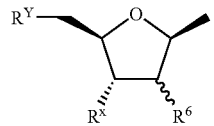

represents a D-ribosyl group, or a pharmaceutically acceptable salt thereof, or a prodrug thereof.

6. A benzimidazole derivative as claimed in claim 3 wherein n represents 1 and both of $R^{X}$ and $R^{Y}$ represent a hydroxy group, or a pharmaceutically acceptable salt thereof, or a prodrug thereof.

7. A benzimidazole derivative as claimed in claim 6 wherein $R^{1}$ represents $OR^{7}$ with the proviso that $R^{7}$ represents a $C_{1-6}$ alkyl group which has a hydroxy group, $NR^{17}R^{18}$ or $N^{+}R^{D}R^{E}R^{F}$ wherein $R^{17}$, $R^{18}$ and $R^{D-F}$ have the same meanings as defined in claim 1 or a hydroxy group; $R^{2}$ represents $OR^{7}$ with the proviso that $R^{7}$ represents a $C_{1-6}$ alkyl group which has a hydroxy group, $NR^{17}R^{18}$ or $N^{30}R^{D}R^{E}R^{F}$ wherein $R^{17}$, $R^{18}$ and $R^{D-F}$ have the same meanings as defined in claim 1, a hydroxy group, or a $C_{6-10}$ aryl group which may have a hydroxy group or $OR^{15}$, wherein $R^{15}$ has the same meaning as defined in claim 1, $R^{3}$, $R^{4}$ and $R^{5}$ represent a hydrogen atom, or a pharmaceutically acceptable salt thereof, or a prodrug thereof.

8. A pharmaceutical composition comprising as an active ingredient a benzimidazole derivative as claimed in claim 1 or a pharmaceutically acceptable salt thereof, or a prodrug thereof.

9. A method for the treatment of a disease associated with an abnormality of plasma uric acid level comprising administering a pharmaceutical composition as claimed in claim 8 to a person having said disease.

10. The method as claimed in claim 9 wherein the disease associated with an abnormality of plasma uric acid level is a disease selected from gout, hyperuricemia, urinary lithiasis, hyperuricemic nephropathy and acute uric acid nephropathy.

11. The method as claimed in claim 9 wherein the disease associated with an abnormality of plasma uric acid level is gout.

12. The method as claimed in claim 9 wherein the disease associated with an abnormality of plasma uric acid level is hyperuricemia.

13. A pharmaceutical composition as claimed in claim 8 comprising in combination as an active ingredient at least one agent selected from the group consisting of colchicine, a nonsteroidal anti-inflammatory agent, an adrenocortical steroid, a uric acid synthesis inhibitor, a uricosuric drug, a urinary alkalinizer and a uric acid oxidase.

14. A pharmaceutical composition as claimed in claim 13 wherein the nonsteroidal anti-inflammatory agent is indometacin, naproxen, fenbufen, pranoprofen, oxaprozin, ketoprofen, etoricoxib or tenoxicam; the uric acid synthesis inhibitor is allopurmnol, oxypurinol, febuxostat or Y-700; the uricosuric drug is probenecid, bucolome or benzbromarone; the urinary alkalinizer is sodium hydrogen carbonate, potassium citrate or sodium citrate; the uric acid oxidase is rasburicase, uricase PEG-20, a recombinant uric acid oxidase (uricase).

* * * * *

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 1
tgcactgcat ggttgctgct                                          20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 2
gtctaagtcc tgtggcttcc                                          20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 3
```
aggagccaga gggaatcaat                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
acatcttggt gagtgagttg                                              20

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 5
ccgctcgaga ggagccagag ggaatcaat                                    29

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 6
cgtctagaac atcttggtga gtgagttg                                     28

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 7
gccagccagc agcaaaaa                                                18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 8
tggagaagtg gctgacct                                                18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 9
atttaccagt gctgccgtga g                                            21

<210> SEQ ID NO 10
<211> LENGTH: 21
<212> TYPE: DNA

```
<213> ORGANISM: Artificial Sequence
<220> FEATURE:
<223> OTHER INFORMATION: Description of Artificial Sequence: primer

<400> SEQUENCE: 10
aaaccgacag cagttgtcca g                                              21

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 11
agagcgtcaa tccagagttc agccca                                         26

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 12
ggcagcttgc atcttgaatt tc                                             22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 13
caaaaacgag tgaaccagga ca                                             22

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 14
ccttgtttgt catcacctgc ttggtgatct                                     30

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 15
gctggtccga ccatatttac cttac                                          25

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 16
cgcttccagc aatggtagag a                                              21
```

```
<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 17
tcaccaagtc tgaactccac gccatc    26
```